United States Patent
Schellin et al.

(10) Patent No.: US 10,499,918 B2
(45) Date of Patent: Dec. 10, 2019

(54) SURGICAL STAPLER BUTTRESS ASSEMBLY WITH FEATURES TO INTERACT WITH MOVABLE END EFFECTOR COMPONENTS

(71) Applicant: Ethicon Endo-Surgery, LLC, Guaynabo, PR (US)

(72) Inventors: Emily A. Schellin, Cincinnati, OH (US); Trevor J. Barton, Cincinnati, OH (US); Prudence A. Turner, Independence, KY (US); Michael J. Vendely, Lebanon, OH (US); Mark S. Zeiner, Mason, OH (US); Charles J. Scheib, Loveland, OH (US); Jason L. Harris, Lebanon, OH (US); Frederick E. Shelton, IV, Hillsboro, OH (US)

(73) Assignee: Ethicon LLC, Guaynabo, PR (US)

( * ) Notice: Subject to any disclaimer, the term of this patent is extended or adjusted under 35 U.S.C. 154(b) by 621 days.

(21) Appl. No.: 14/926,072

(22) Filed: Oct. 29, 2015

(65) Prior Publication Data
US 2017/0119390 A1    May 4, 2017

(51) Int. Cl.
*A61B 17/10* (2006.01)
*A61B 17/072* (2006.01)
(Continued)

(52) U.S. Cl.
CPC .......... *A61B 17/105* (2013.01); *A61B 17/068* (2013.01); *A61B 17/07207* (2013.01);
(Continued)

(58) Field of Classification Search
CPC ............ A61B 17/068; A61B 17/07207; A61B 17/06166; A61B 17/07292; A61B 17/105;
(Continued)

(56) References Cited

U.S. PATENT DOCUMENTS

| 4,805,823 A | 2/1989 | Rothfuss |
| 5,415,334 A | 5/1995 | Williamson et al. |

(Continued)

FOREIGN PATENT DOCUMENTS

| EP | 1 064 883 A1 | 1/2001 |
| EP | 2 005 894 A2 | 12/2008 |

(Continued)

OTHER PUBLICATIONS

U.S. Appl. No. 62/209,041, filed Aug. 24, 2015.
(Continued)

*Primary Examiner* — Robert F Long
(74) *Attorney, Agent, or Firm* — Frost Brown Todd LLC

(57) ABSTRACT

A staple cartridge includes a plurality of staples and a deck defining a plurality of openings. Each opening of the plurality of openings is associated with a corresponding staple of the plurality of staples, such that each staple is configured to pass through a corresponding opening of the plurality of openings. The deck further includes a first mechanical coupling feature and a buttress assembly. The buttress assembly includes a buttress body and a second mechanical coupling feature. The second mechanical coupling feature is configured to engage the first mechanical coupling feature to releasably couple the buttress body to the deck.

15 Claims, 38 Drawing Sheets

(51) Int. Cl.
*A61B 17/068* (2006.01)
*A61B 17/32* (2006.01)
*A61B 17/00* (2006.01)
*A61B 17/29* (2006.01)

(52) U.S. Cl.
CPC ........ *A61B 17/07292* (2013.01); *A61B 17/32* (2013.01); *A61B 2017/00004* (2013.01); *A61B 2017/00398* (2013.01); *A61B 2017/00477* (2013.01); *A61B 2017/00734* (2013.01); *A61B 2017/00884* (2013.01); *A61B 2017/00951* (2013.01); *A61B 2017/07271* (2013.01); *A61B 2017/2936* (2013.01)

(58) Field of Classification Search
CPC ............ A61B 17/32; A61B 2017/2936; A61B 2017/07271; A61B 2017/00951; A61B 2017/00884; A61B 2017/00734; A61B 2017/00398; A61B 2017/00004; A61B 2017/00477
USPC .......................................... 227/175.1–182.1
See application file for complete search history.

(56) References Cited

U.S. PATENT DOCUMENTS

| | | | | |
|---|---|---|---|---|
| 5,465,895 | A | 11/1995 | Knodel et al. | |
| 5,597,107 | A | 1/1997 | Knodel et al. | |
| 5,632,432 | A | 5/1997 | Schulze et al. | |
| 5,673,840 | A | 10/1997 | Schulze et al. | |
| 5,704,534 | A | 1/1998 | Huitema et al. | |
| 5,752,965 | A * | 5/1998 | Francis | A61B 17/07207 227/178.1 |
| 5,792,135 | A | 8/1998 | Madhani et al. | |
| 5,814,055 | A | 9/1998 | Knodel et al. | |
| 5,817,084 | A | 10/1998 | Jensen | |
| 5,878,193 | A | 3/1999 | Wang et al. | |
| 6,019,791 | A * | 2/2000 | Wood | A61F 2/2445 623/2.11 |
| 6,231,565 | B1 | 5/2001 | Tovey et al. | |
| 6,273,897 | B1 * | 8/2001 | Dalessandro | A61B 17/07207 606/139 |
| 6,325,810 | B1 * | 12/2001 | Hamilton | A61B 17/07207 227/175.1 |
| 6,364,888 | B1 | 4/2002 | Niemeyer et al. | |
| 6,503,257 | B2 * | 1/2003 | Grant | A61B 17/07207 606/148 |
| 6,592,597 | B2 * | 7/2003 | Grant | A61B 17/072 227/175.1 |
| 6,783,524 | B2 | 8/2004 | Anderson et al. | |
| 6,978,921 | B2 | 12/2005 | Shelton, IV et al. | |
| 7,000,818 | B2 | 2/2006 | Shelton, IV et al. | |
| 7,143,923 | B2 | 12/2006 | Shelton, IV et al. | |
| 7,303,108 | B2 | 12/2007 | Shelton, IV | |
| 7,367,485 | B2 | 5/2008 | Shelton, IV et al. | |
| 7,380,695 | B2 | 6/2008 | Doll et al. | |
| 7,380,696 | B2 | 6/2008 | Shelton, IV et al. | |
| 7,404,508 | B2 | 7/2008 | Smith et al. | |
| 7,434,715 | B2 | 10/2008 | Shelton, IV et al. | |
| 7,524,320 | B2 | 4/2009 | Tierney | |
| 7,691,098 | B2 | 4/2010 | Wallace | |
| 7,721,930 | B2 | 5/2010 | McKenna et al. | |
| 7,806,891 | B2 | 10/2010 | Nowlin et al. | |
| 7,950,561 | B2 | 5/2011 | Aranyi | |
| 7,988,027 | B2 * | 8/2011 | Olson | A61B 17/07207 227/175.1 |
| 8,141,762 | B2 | 3/2012 | Bedi et al. | |
| 8,210,411 | B2 | 7/2012 | Yates et al. | |
| 8,231,043 | B2 * | 7/2012 | Tarinelli | A61B 17/07207 227/180.1 |
| 8,371,491 | B2 * | 2/2013 | Huitema | A61B 17/07207 227/176.1 |
| 8,408,439 | B2 | 4/2013 | Huang et al. | |
| 8,453,914 | B2 | 6/2013 | Laurent et al. | |
| 8,464,925 | B2 * | 6/2013 | Hull | A61B 17/00491 227/179.1 |
| 8,479,969 | B2 | 7/2013 | Shelton, IV | |
| 8,540,131 | B2 * | 9/2013 | Swayze | A61B 17/07207 227/176.1 |
| 8,573,461 | B2 | 11/2013 | Shelton, IV et al. | |
| 8,573,465 | B2 | 11/2013 | Shelton, IV | |
| 8,602,288 | B2 | 12/2013 | Shelton, IV et al. | |
| 8,616,430 | B2 * | 12/2013 | (Prommersberger) Stopek | A61B 17/07207 227/176.1 |
| 8,616,431 | B2 | 12/2013 | Timm et al. | |
| 8,668,129 | B2 * | 3/2014 | Olson | A61B 17/072 227/175.1 |
| 8,783,541 | B2 | 7/2014 | Shelton, IV et al. | |
| 8,800,838 | B2 | 8/2014 | Shelton, IV | |
| 8,801,735 | B2 | 8/2014 | Shelton, IV et al. | |
| 8,814,025 | B2 * | 8/2014 | Miller | A61B 17/00491 227/180.1 |
| 8,820,605 | B2 | 9/2014 | Shelton, IV | |
| 8,844,789 | B2 | 9/2014 | Shelton, IV et al. | |
| 8,899,464 | B2 | 12/2014 | Hueil et al. | |
| 8,998,060 | B2 | 4/2015 | Bruewer et al. | |
| 9,101,359 | B2 | 8/2015 | Smith et al. | |
| 9,186,142 | B2 | 11/2015 | Fanelli et al. | |
| 9,192,384 | B2 * | 11/2015 | Bettuchi | A61B 17/07292 |
| 9,198,644 | B2 * | 12/2015 | Balek | A61B 17/00491 |
| 9,211,120 | B2 | 12/2015 | Scheib et al. | |
| 9,237,892 | B2 * | 1/2016 | Hodgkinson | A61B 17/07207 |
| 9,301,759 | B2 | 4/2016 | Spivey et al. | |
| 9,307,989 | B2 | 4/2016 | Shelton, IV et al. | |
| 9,393,018 | B2 | 7/2016 | Wang et al. | |
| 9,398,911 | B2 | 7/2016 | Auld | |
| 9,433,420 | B2 * | 9/2016 | Hodgkinson | A61B 17/07207 |
| 9,492,170 | B2 | 11/2016 | Bear et al. | |
| 9,517,065 | B2 | 12/2016 | Simms et al. | |
| 9,572,576 | B2 * | 2/2017 | Hodgkinson | A61B 17/07207 |
| 9,585,657 | B2 * | 3/2017 | Shelton, IV | A61B 17/07207 |
| 9,610,080 | B2 * | 4/2017 | Whitfield | A61B 17/07292 |
| 9,615,826 | B2 * | 4/2017 | Shelton, IV | A61B 17/068 |
| 9,788,835 | B2 | 10/2017 | Morgan et al. | |
| 10,172,617 | B2 * | 1/2019 | Shelton, IV | A61B 17/07292 |
| 2005/0070929 | A1 * | 3/2005 | Dalessandro | A61B 17/07207 606/151 |
| 2006/0025816 | A1 * | 2/2006 | Shelton, IV | A61B 17/07207 606/215 |
| 2006/0135992 | A1 * | 6/2006 | Bettuchi | A61B 17/072 606/219 |
| 2006/0271104 | A1 * | 11/2006 | Viola | A61B 17/00491 606/214 |
| 2008/0110958 | A1 * | 5/2008 | McKenna | A61B 17/00491 227/176.1 |
| 2008/0169328 | A1 | 7/2008 | Shelton, IV | |
| 2009/0001122 | A1 * | 1/2009 | Prommersberger | A61B 17/07207 227/176.1 |
| 2009/0092651 | A1 * | 4/2009 | Shah | A61L 27/34 424/422 |
| 2009/0218384 | A1 * | 9/2009 | Aranyi | A61B 17/07207 227/176.1 |
| 2010/0147922 | A1 * | 6/2010 | Olson | A61B 17/072 227/176.1 |
| 2011/0282382 | A1 * | 11/2011 | McAlister | A61B 17/00491 606/213 |
| 2012/0160721 | A1 * | 6/2012 | Shelton, IV | A61B 17/00491 206/339 |
| 2012/0187179 | A1 * | 7/2012 | Gleiman | A61B 17/072 227/176.1 |
| 2012/0241493 | A1 | 9/2012 | Baxter, III et al. | |
| 2013/0062391 | A1 * | 3/2013 | Boudreaux | A61B 17/00491 227/175.1 |
| 2013/0068816 | A1 * | 3/2013 | Mandakolathur Vasudevan | A61B 17/07292 227/175.1 |
| 2013/0075446 | A1 * | 3/2013 | Wang | A61B 17/068 227/176.1 |

(56) References Cited

U.S. PATENT DOCUMENTS

| | | | |
|---|---|---|---|
| 2013/0075447 A1 | 3/2013 | Weisenburgh, II et al. | |
| 2013/0082086 A1* | 4/2013 | Hueil | A61B 17/07207 227/177.1 |
| 2013/0112731 A1* | 5/2013 | Hodgkinson | A61B 17/0682 227/176.1 |
| 2013/0146643 A1* | 6/2013 | Schmid | A61B 17/0682 227/180.1 |
| 2013/0153640 A1* | 6/2013 | Hodgkinson | A61B 17/07207 227/180.1 |
| 2013/0206813 A1 | 8/2013 | Nalagatla | |
| 2013/0214030 A1* | 8/2013 | Aronhalt | A61B 17/0682 227/176.1 |
| 2013/0256373 A1* | 10/2013 | Schmid | A61B 17/07207 227/176.1 |
| 2014/0061280 A1* | 3/2014 | Ingmanson | A61B 17/07292 227/176.1 |
| 2014/0130330 A1* | 5/2014 | Olson | A61B 17/07207 29/428 |
| 2014/0138423 A1* | 5/2014 | Whitfield | A61B 17/07292 227/176.1 |
| 2014/0224686 A1* | 8/2014 | Aronhalt | A61B 17/068 206/339 |
| 2014/0239036 A1 | 8/2014 | Zerkle et al. | |
| 2014/0239037 A1 | 8/2014 | Boudreaux et al. | |
| 2014/0239038 A1 | 8/2014 | Leimbach et al. | |
| 2014/0239040 A1 | 8/2014 | Fanelli et al. | |
| 2014/0239041 A1 | 8/2014 | Zerkle et al. | |
| 2014/0239043 A1 | 8/2014 | Simms et al. | |
| 2014/0239044 A1 | 8/2014 | Hoffman | |
| 2014/0263563 A1 | 9/2014 | Stokes et al. | |
| 2015/0196299 A1* | 7/2015 | Swayze | A61B 17/068 227/176.1 |
| 2015/0209045 A1* | 7/2015 | Hodgkinson | A61B 17/07207 227/176.1 |
| 2015/0238185 A1* | 8/2015 | Schellin | A61B 17/07207 227/175.1 |
| 2015/0272575 A1 | 10/2015 | Leimbach et al. | |
| 2015/0351754 A1 | 12/2015 | Harris et al. | |
| 2015/0351758 A1 | 12/2015 | Shelton, IV et al. | |
| 2015/0351763 A1* | 12/2015 | Shelton, IV | A61B 17/00491 227/176.1 |
| 2015/0374360 A1 | 12/2015 | Scheib et al. | |
| 2015/0374373 A1 | 12/2015 | Rector et al. | |
| 2016/0089146 A1 | 3/2016 | Harris et al. | |
| 2016/0278774 A1* | 9/2016 | Shelton, IV | A61B 17/068 |
| 2016/0278778 A1* | 9/2016 | Shelton, IV | A61B 17/068 |
| 2017/0042540 A1* | 2/2017 | Olson | A61B 17/07207 |
| 2017/0119389 A1* | 5/2017 | Turner | A61B 17/068 |
| 2018/0235623 A1* | 8/2018 | Vendely | A61B 17/07207 |

FOREIGN PATENT DOCUMENTS

| | | |
|---|---|---|
| EP | 2 090 244 A2 | 8/2009 |
| EP | 2 910 198 A2 | 8/2015 |
| EP | 2 954 853 A1 | 12/2015 |
| EP | 3 072 458 A2 | 9/2016 |

OTHER PUBLICATIONS

U.S. Appl. No. 14/810,786, filed Jul. 28, 2015.
U.S. Appl. No. 14/811,087, filed Jul. 28, 2015.
U.S. Appl. No. 14/811,154, filed Jul. 28, 2015.
U.S. Appl. No. 14/827,856, filed Aug. 17, 2015.
U.S. Appl. No. 14/840,613, filed Aug. 31, 2015.
U.S. Appl. No. 14/871,071, filed Sep. 30, 2015.
U.S. Appl. No. 14/871,131, filed Sep. 30, 2015.
European Search Report, Partial, dated Mar. 27, 2017 for Application No. EP 16196344.2, 10 pgs.
European Search Report, Extended, and Written Opinion dated Jul. 4, 2017 for Application No. EP 16196344.2, 14 pgs.
International Search Report and Written Opinion dated May 19, 2017 for Application No. PCT/US2016/058392, 24 pgs.

* cited by examiner

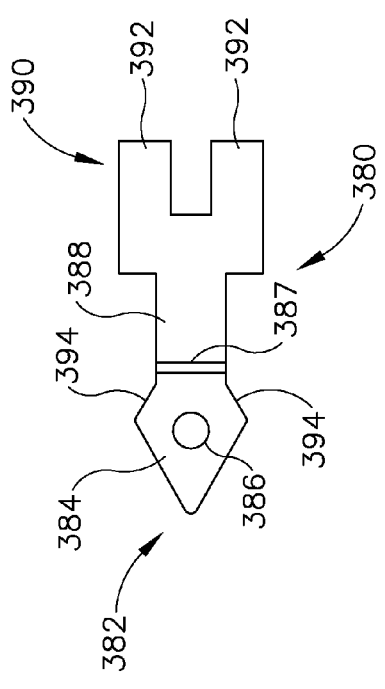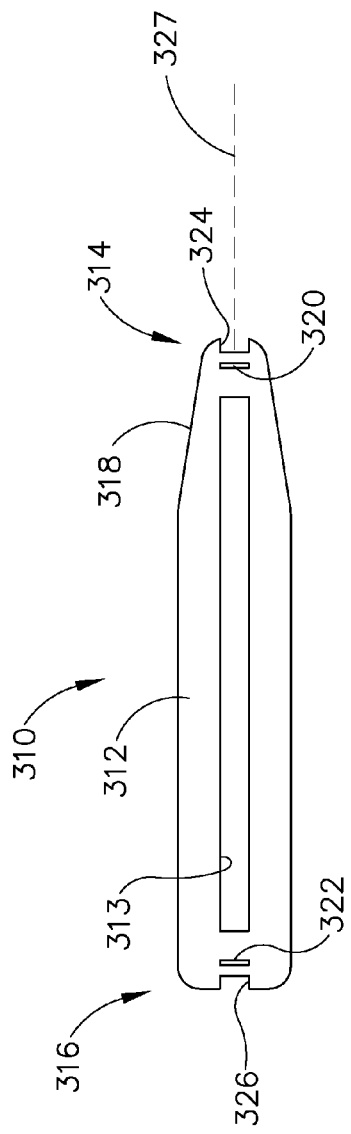
Fig.10
Fig.11

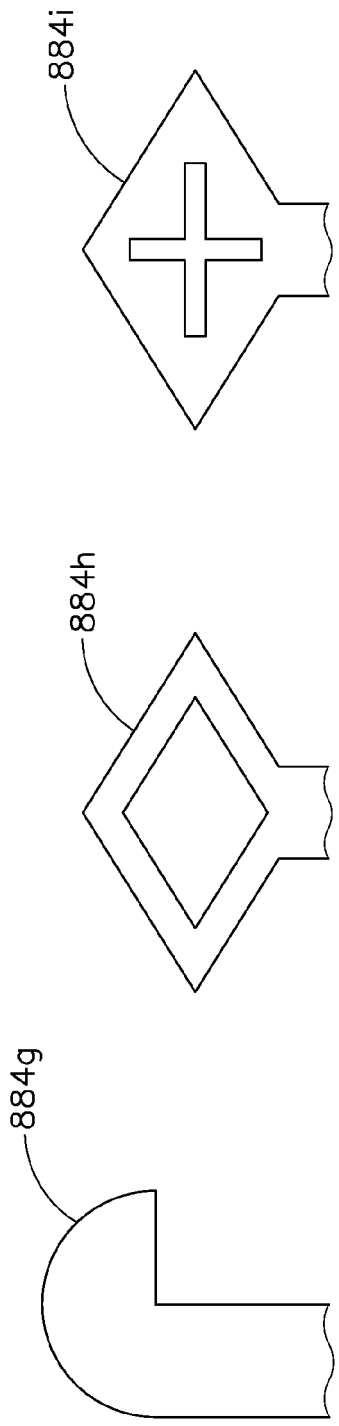
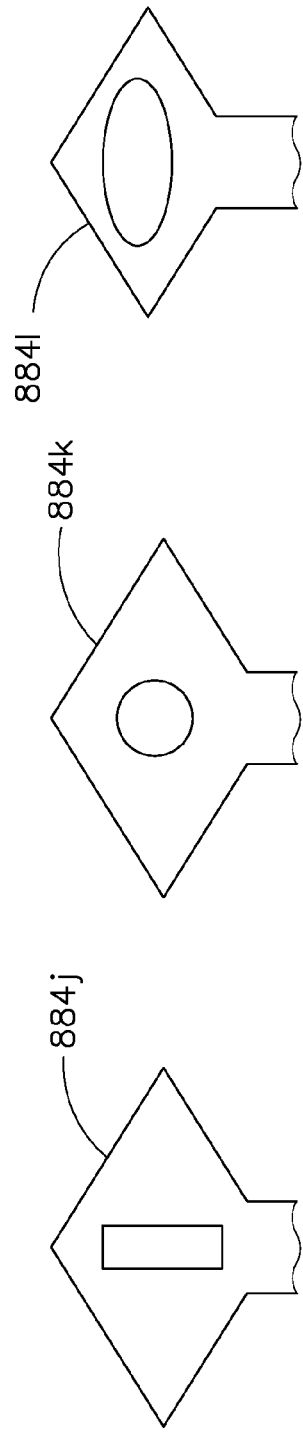
Fig. 25
Fig. 26
Fig. 27
Fig. 28
Fig. 29
Fig. 30

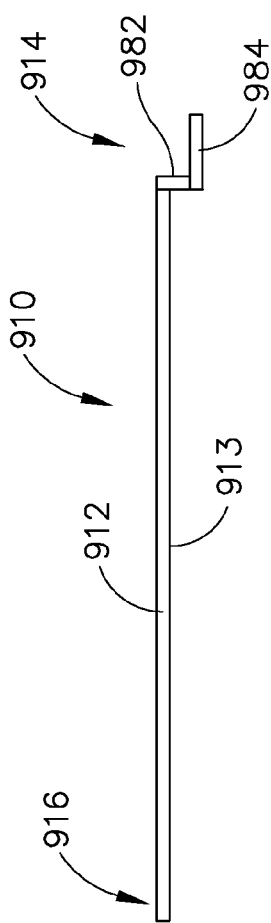
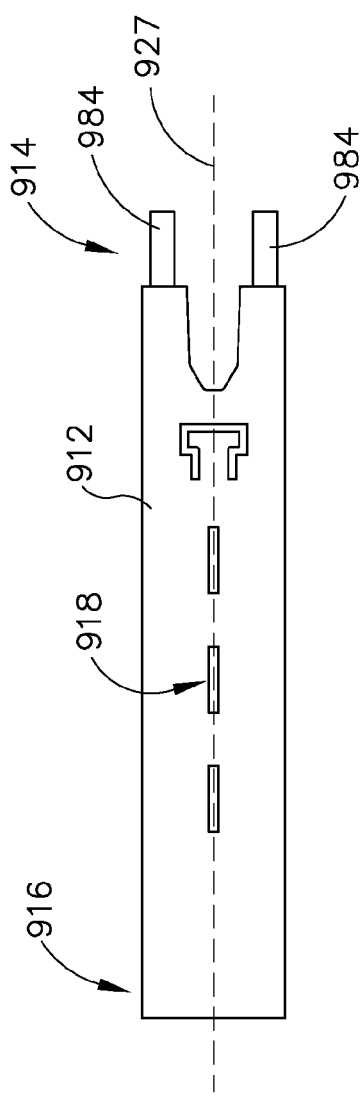
Fig. 32
Fig. 33

SURGICAL STAPLER BUTTRESS ASSEMBLY WITH FEATURES TO INTERACT WITH MOVABLE END EFFECTOR COMPONENTS

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasonic vibration, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy, and thereby between a patient's ribs, to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

Examples of surgical staplers that may be particularly suited for use through a thoracotomy are disclosed in U.S. Patent Pub. No. 2014/0243801, entitled "Surgical Instrument End Effector Articulation Drive with Pinion and Opposing Racks," published Aug. 28, 2014, issued as U.S. Pat. No. 9,186,142 on Nov. 17, 2015; U.S. Patent Pub. No. 2014/0239041, entitled "Lockout Feature for Movable Cutting Member of Surgical Instrument," published Aug. 28, 2014, issued as U.S. Pat. No. 9,717,497 on Aug. 1, 2017; U.S. Patent Pub. No. 2014/0239042, entitled "Integrated Tissue Positioning and Jaw Alignment Features for Surgical Stapler," published August 28, 2014, issued as U.S. Pat. No. 9,517,065 on Dec. 13, 2016; U.S. Patent Pub. No. 2014/0239036, entitled "Jaw Closure Feature for End Effector of Surgical Instrument," published Aug. 28, 2014, issued as U.S. Pat. No. 9,839,421 on Dec. 12, 2017; U.S. Patent Pub. No. 2014/0239040, entitled "Surgical Instrument with Articulation Lock having a Detenting Binary Spring," published Aug. 28, 2014, issued as U.S. Pat. No. 9,867,615 on Jan. 16, 2018; U.S. Patent Pub. No. 2014/0239043, entitled "Distal Tip Features for End Effector of Surgical Instrument," published Aug. 28, 2014, issued as U.S. Pat. No. 9,622,746 on Apr. 18, 2017; U.S. Patent Pub. No. 2014/0239037, entitled "Staple Forming Features for Surgical Stapling Instrument," published Aug. 28, 2014, issued as U.S. Pat. No. 10,092,292 on Oct. 9, 2018; U.S. Patent Pub. No. 2014/0239038, entitled "Surgical Instrument with Multi-Diameter Shaft," published Aug. 28, 2014, issued as U.S. Pat. No. 9,795,379 on Oct. 24, 2017; and U.S. Patent Pub. No. 2014/0239044, entitled "Installation Features for Surgical Instrument End Effector Cartridge," published Aug. 28, 2014, issued as U.S. Pat. No. 9,808,248 on Nov. 7, 2017. The disclosure of each of the above-cited U.S. Patent Publications is incorporated by reference herein.

Additional surgical stapling instruments are disclosed in U.S. Pat. No. 8,801,735, entitled "Surgical Circular Stapler with Tissue Retention Arrangements," issued Aug. 12, 2014; U.S. Pat. No. 8,141,762, entitled "Surgical Stapler Comprising a Staple Pocket," issued Mar. 27, 2012; U.S. Pat. No. 8,371,491, entitled "Surgical End Effector Having Buttress Retention Features," issued February 12, 2013; U.S. Pub. No. 2014/0263563, entitled "Method and Apparatus for Sealing End-to-End Anastomosis" published Sep. 18, 2014, issued as U.S. Pat. No. 9,597,082 on Mar. 21, 2017; U.S. Pub. No. 2014/0246473, entitled "Rotary Powered Surgical Instruments with Multiple Degrees of Freedom," published Sep. 4, 2014, issued as U.S. Pat. No. 9,398,911 on Jul. 26, 2016; U.S. Pub, No. 2013/0206813, entitled "Linear Stapler," published Aug. 15, 2013, now abandoned; U.S. Pub. No. 2008/0169328, entitled "Buttress Material for Use with a Surgical Stapler," published Jul. 17, 2008, now abandoned; U.S. Pat. App. No. 14/300,804, entitled "Woven and Fibrous Materials for Reinforcing a Staple Line," filed Jun. 10, 2014, issued as U.S, Pat. No. 9,848,871 on Dec. 26, 2017; U.S. Pat. App. No. 14/300,811, entitled "Devices and Methods for Sealing Staples in Tissue", issued as U.S. Pat. No. 9,936,954 on Apr. 10, 2018; and U.S. patent application Ser. No. 14/498,070, entitled "Radically Expandable Staple Line" filed Sep. 26, 2014, issued as U.S. Pat. No. 10,426,479 on Oct. 1, 2019. The disclosure of each of the above-cited U.S. Patents, U.S. Patent Publications, and U.S. Patent Applications is incorporated by reference herein.

In some instances, it may be desirable to equip a surgical stapling instrument with a buttress material to reinforce the mechanical fastening of tissue provided by staples. Such a buttress may prevent the applied staples from pulling through tissue and may otherwise reduce a risk of tissue tearing at or near the site of applied staples.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 10 depicts a top plan view of a connector portion suitable for coupling a buttress assembly to a staple cartridge;

FIG. 11 depicts a top plan view of an exemplary alternative buttress assembly;

FIG. 25 depicts a top plan view of another exemplary alternative head portion suitable for incorporation into any of the connector portions shown in FIGS. 10 and 12-18;

FIG. 26 depicts a top plan view of another exemplary alternative head portion suitable for incorporation into any of the connector portions shown in FIGS. 10 and 12-18;

FIG. 27 depicts a top plan view of another exemplary alternative head portion suitable for incorporation into any of the connector portions shown in FIGS. 10 and 12-18;

FIG. 28 depicts a top plan view of another exemplary alternative head portion suitable for incorporation into any of the connector portions shown in FIGS. 10 and 12-18;

FIG. 29 depicts a top plan view of another exemplary alternative head portion suitable for incorporation into any of the connector portions shown in FIGS. 10 and 12-18;

FIG. 30 depicts a top plan view of another exemplary alternative head portion suitable for incorporation into any of the connector portions shown in FIGS. 10 and 12-18;

FIG. 32 depicts a side elevational view of another exemplary alternative buttress assembly;

FIG. 33 depicts a top plan view of the buttress assembly of FIG. 32;

Figure 1:
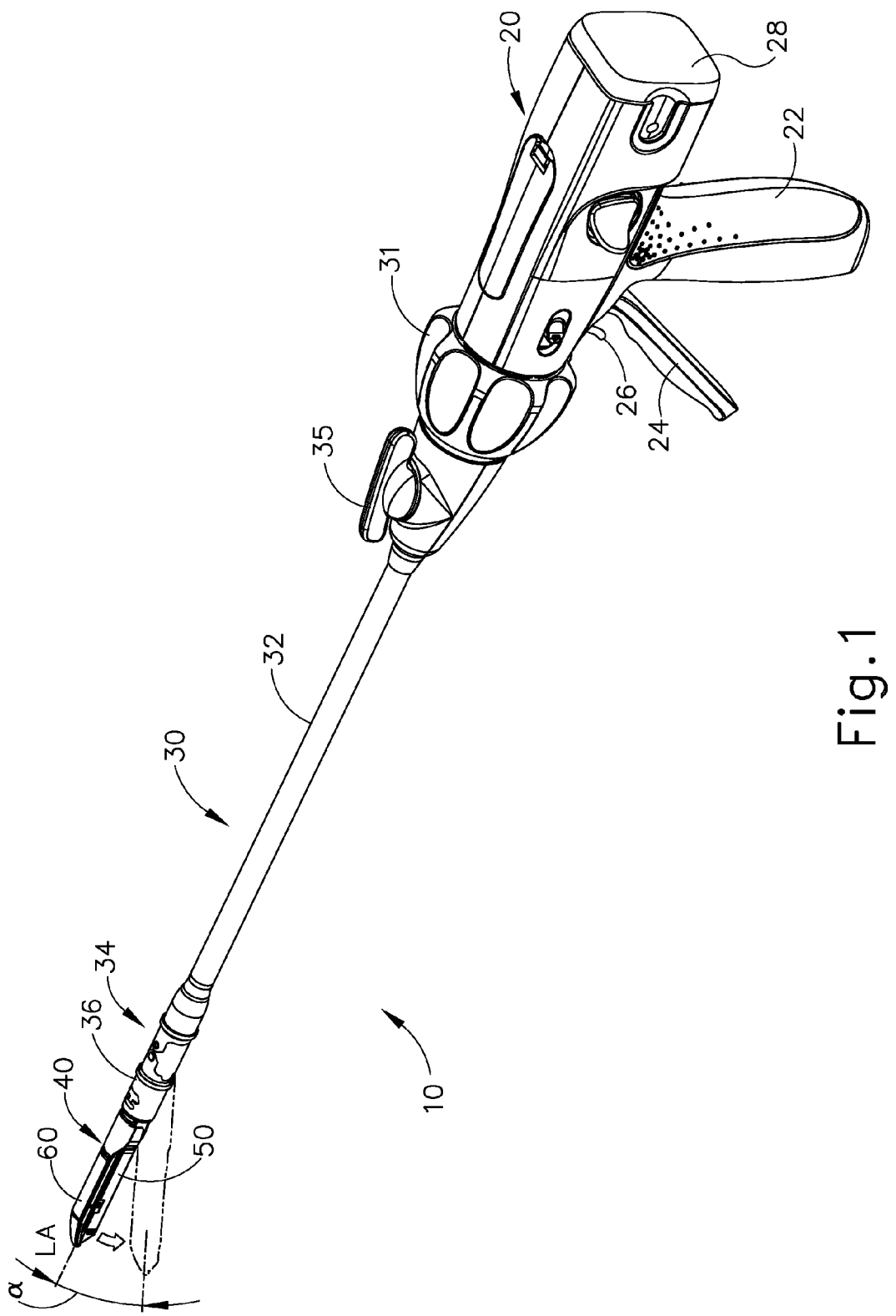
FIG. 1 depicts a perspective view of an exemplary articulating surgical stapling instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Stapler

FIG. 1 depicts an exemplary surgical stapling and severing instrument (10) that includes a handle assembly (20), a shaft assembly (30), and an end effector (40). End effector (40) and the distal portion of shaft assembly (30) are sized for insertion, in a nonarticulated state as depicted in FIG. 1, through a trocar cannula to a surgical site in a patient for performing a surgical procedure. By way of example only, such a trocar may be inserted in a patient's abdomen, between two of the patient's ribs, or elsewhere. In some settings, instrument (10) is used without a trocar. For instance, end effector (40) and the distal portion of shaft assembly (30) may be inserted directly through a thoracotomy or other type of incision. It should be understood that terms such as "proximal" and "distal" are used herein with reference to a clinician gripping handle assembly (20) of instrument (10). Thus, end effector (40) is distal with respect to the more proximal handle assembly (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

A. Exemplary Handle Assembly and Shaft Assembly

As shown in FIG. 1, handle assembly (20) of the present example comprises pistol grip (22), a closure trigger (24), and a firing trigger (26). Each trigger (24, 26) is selectively pivotable toward and away from pistol grip (22) as will be described in greater detail below. Handle assembly (20) further includes a removable battery pack (28). These components will also be described in greater detail below. Of course, handle assembly (20) may have a variety of other components, features, and operabilities, in addition to or in lieu of any of those noted above. Other suitable configurations for handle assembly (20) will be apparent to those of ordinary skill in the art in view of the teachings herein.

Figure 2:
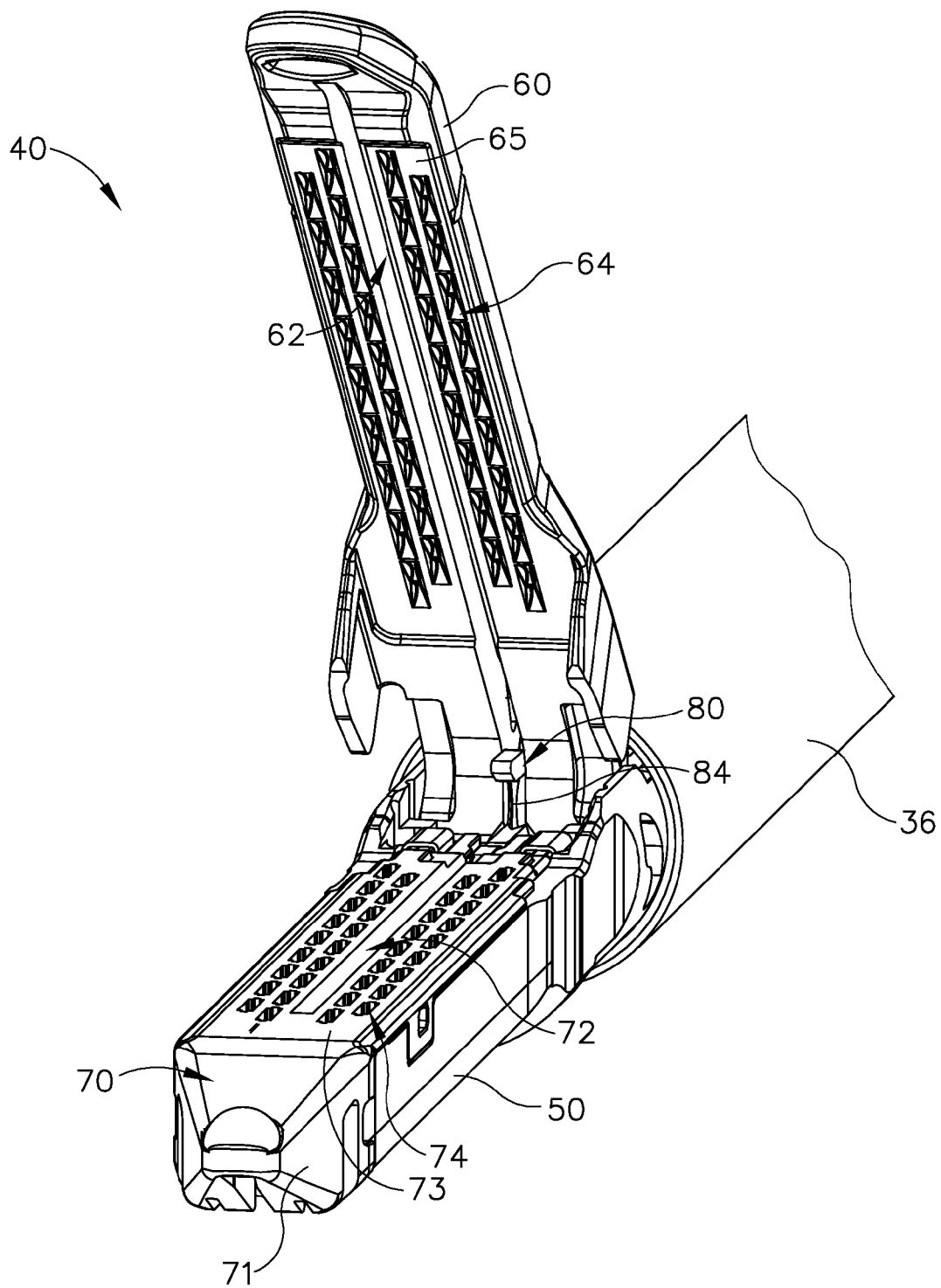
FIG. 2 depicts a perspective view of an end effector of the instrument of FIG. 1, with the end effector in an open configuration.

As shown in FIGS. 1-2, shaft assembly (30) of the present example comprises an outer closure tube (32), an articulation section (34), and a closure ring (36), which is further coupled with end effector (40). Closure tube (32) extends along the length of shaft assembly (30). Closure ring (36) is positioned distal to articulation section (34). Closure tube (32) and closure ring (36) are configured to translate longitudinally relative to handle assembly (20). Longitudinal translation of closure tube (32) is communicated to closure ring (36) via articulation section (34). Exemplary features that may be used to provide longitudinal translation of closure tube (32) and closure ring (36) will be described in greater detail below.

Articulation section (34) is operable to laterally deflect closure ring (36) and end effector (40) laterally away from the longitudinal axis (LA) of shaft assembly (30) at a desired angle (μ). In the present example, articulation is controlled through an articulation control knob (35) which is located at the proximal end of shaft assembly (30). Closure ring (36) and end effector (40) pivot about an axis that is perpendicular to the longitudinal axis (LA) of shaft assembly (30) in response to rotation of knob (35). Articulation section (34) is configured to communicate longitudinal translation of closure tube (32) to closure ring (36), regardless of whether articulation section (34) is in a straight configuration or an articulated configuration. By way of example only, articulation section (34) and/or articulation control knob (35) may be constructed and operable in accordance with at least some of the teachings of U.S. Pub. No. 2014/0243801, entitled "Surgical Instrument End Effector Articulation Drive with Pinion and Opposing Racks," published Aug. 28, 2014, issued as U.S. Pat. No. 9,186,142 on Nov. 1, 2015, the disclosure of which is incorporated by reference herein; and/or U.S. paten application Ser. No. 14/314,125, entitled "Articulation Drive Features for Surgical Stapler," filed Jun. 25, 2014, issued as U.S. Pat. No. 10,292,701 on May 21, 2019. the disclosure of which is incorporated by reference herein; and/or in accordance with the various teachings below. Other suitable forms that articulation section (34) and articulation knob (35) may take will be apparent to those of ordinary skill in the art in view of the teachings herein.

As shown in FIG. 1, shaft assembly (30) of the present example further includes a rotation knob (31). Rotation knob (31) is operable to rotate the entire shaft assembly (30) and end effector (40) relative to handle assembly (20) about the longitudinal axis (LA) of shaft assembly (30). Of course, shaft assembly (30) may have a variety of other components, features, and operabilities, in addition to or in lieu of any of those noted above. By way of example only, at least part of shaft assembly (30) is constructed in accordance with at least some of the teachings of U.S. Pub. No. 2014/0239038, entitled "Surgical Instrument with Multi-Diameter Shaft," published Aug. 28, 2014, issued as U.S. Pat. No. 9,795,379 on Oct. 24, 2017, the disclosure of which is incorporated by reference herein. Other suitable configurations for shaft assembly (30) will be apparent to those of ordinary skill in the art in view of the teachings herein.

B. Exemplary End Effector

Figure 3:
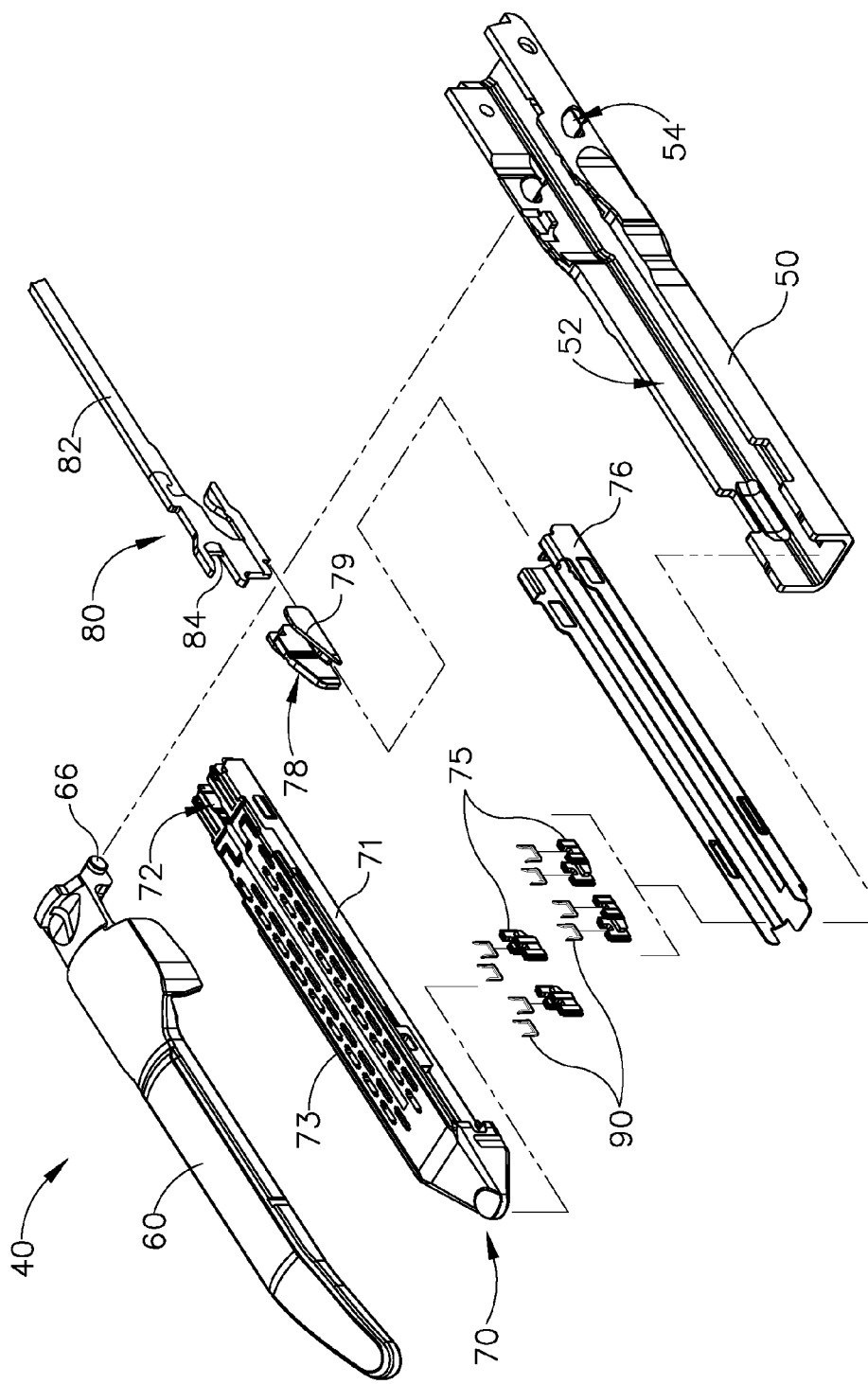
FIG. 3 depicts an exploded perspective view of the end effector of FIG. 2.

As also shown in FIGS. 1-3, end effector (40) of the present example includes a lower jaw (50) and a pivotable anvil (60). Anvil (60) includes a pair of integral, outwardly extending pins (66) that are disposed in corresponding curved slots (54) of lower jaw (50). Anvil (60) is pivotable toward and away from lower jaw (50) between an open position (shown in FIG. 2) and a closed position (shown in FIG. 1). Use of the term "pivotable" (and similar terms with "pivot" as a base) should not be read as necessarily requiring pivotal movement about a fixed axis. For instance, in the present example, anvil (60) pivots about an axis that is defined by pins (66), which slide along curved slots (54) of lower jaw (50) as anvil (60) moves toward lower jaw (50). In such versions, the pivot axis translates along the path defined by slots (54) while anvil (60) simultaneously pivots about that axis. In addition or in the alternative, the pivot axis may slide along slots (54) first, with anvil (60) then pivoting about the pivot axis after the pivot axis has slid a certain distance along the slots (54). It should be understood that such sliding/translating pivotal movement is encompassed within terms such as "pivot," "pivots," "pivotal," "pivotable," "pivoting," and the like. Of course, some versions may provide pivotal movement of anvil (60) about an axis that remains fixed and does not translate within a slot or channel, etc.

As best seen in FIG. 3, lower jaw (50) of the present example defines a channel (52) that is configured to receive a staple cartridge (70). Staple cartridge (70) may be inserted into channel (52), end effector (40) may be actuated, and then staple cartridge (70) may be removed and replaced with another staple cartridge (70), Lower jaw (50) thus releasably retains staple cartridge (70) in alignment with anvil (60) for actuation of end effector (40). In some versions, lower jaw (50) is constructed in accordance with at least some of the teachings of U.S. Pub. No. 2014/0239044, entitled "Installation Features for Surgical Instrument End Effector Cartridge," published Aug. 28, 2014, issued as U.S. Pat. No. 9,808,248 on Nov. 7, 2017, the disclosure of which is incorporated by reference herein. Other suitable forms that lower jaw (50) may take will be apparent to those of ordinary skill in the art in view of the teachings herein.

As best seen in FIGS. 2-3, staple cartridge (70) of the present example comprises a cartridge body (71) and a tray (76) secured to the underside of cartridge body (71). The upper side of cartridge body (71) presents a deck (73), against which tissue may be compressed when anvil (60) is in a closed position. Cartridge body (71) further defines a longitudinally extending channel (72) and a plurality of staple pockets (74). A staple (90) is positioned in each staple pocket (74). A staple driver (75) is also positioned in each staple pocket (74), underneath a corresponding staple (90), and above tray (76). As will be described in greater detail below, staple drivers (75) are operable to translate upwardly in staple pockets (74) to thereby drive staples (90) upwardly through staple pockets (74) and into engagement with anvil (60). Staple drivers (75) are driven upwardly by a wedge sled (78), which is captured between cartridge body (71) and tray (76), and which translates longitudinally through cartridge body (71).

Wedge sled (78) includes a pair of obliquely angled cam surfaces (79), which are configured to engage staple drivers (75) and thereby drive staple drivers (75) upwardly as wedge sled (78) translates longitudinally through cartridge (70). For instance, when wedge sled (78) is in a proximal position, staple drivers (75) are in downward positions and staples (90) are located in staple pockets (74). As wedge sled (78) is driven to the distal position by a translating knife member (80), wedge sled (78) drives staple drivers (75) upwardly, thereby driving staples (90) out of staple pockets (74) and into staple forming pockets (64) that are formed in the underside (65) of anvil (60). Thus, staple drivers (75) translate along a vertical dimension as wedge sled (78) translates along a horizontal dimension.

In some versions, staple cartridge (70) is constructed and operable in accordance with at least some of the teachings of U. U.S. Pub. No. 2014/0239042, entitled "Integrated Tissue Positioning and Jaw Alignment Features for Surgical Stapler," published Aug. 28, 2014, issued as U.S. Pat. No. 9,517,065 on Dec. 13, 2016, the disclosure of which is incorporated by reference herein. In addition or in the alternative, staple cartridge (70) may be constructed and operable in accordance with at least some of the teachings of U.S. Pub. No. 2014/0239044, entitled "Installation Features for Surgical Instrument End Effector Cartridge," published Aug. 28, 2014, issued as U.S. Pat. No. 9,808,248 on Nov. 7, 2017, the disclosure of which is incorporated by reference herein. Other suitable forms that staple cartridge (70) may take will be apparent to those of ordinary skil in the art in view of the teachings herein.

As best seen in FIG. 2, anvil (60) of the present example comprises a longitudinally extending channel (62) and a plurality of staple forming pockets (64). Channel (62) is configured to align with channel (72) of staple cartridge (70) when anvil (60) is in a closed position. Each staple forming pocket (64) is positioned to lie over a corresponding staple pocket (74) of staple cartridge (70) when anvil (60) is in a closed position. Staple forming pockets (64) are configured to deform the legs of staples (90) when staples (90) are driven through tissue and into anvil (60). In particular, staple forming pockets (64) are configured to bend the legs of staples (90) to secure the formed staples (90) in the tissue. Anvil (60) may be constructed in accordance with at least some of the teachings of U.S. Pub. No. 2014/0239042, entitled "Integrated Tissue Positioning and Jaw Alignment Features for Surgical Stapler," published Aug. 28, 2014, issued as U.S. Pat. No. 9,517,065 on Dec. 13, 2016; at least some of the teachings of U.S. Pub. No. 2014/0239036, entitled "Jaw Closure Feature for End Effector of Surgical Instrument," published Aug. 28, 2014, issued as U.S. Pat. No. 9,839,421 on Dec. 12, 2017; and/or at least some of the teachings of U.S. Pub. No. 2014/0239037, entitled "Staple Forming Features for Surgical Stapling instrument," published Aug. 28, 2014, issued as U.S. Pat. No. 10,092,292 on Oct. 9, 2018, the disclosure of which is incorporated by reference herein. Other suitable forms that anvil (60) may take will be apparent to those of ordinary skill in the art in view of the teachings herein.

In the present example, a knife member (80) is configured to translate through end effector (40). As best seen in FIG. 3, knife member (80) is secured to the distal end of a firing beam (82), which extends through a portion of shaft assembly (30). As best seen in FIG. 2, knife member (80) is positioned in channels (62, 72) of anvil (60) and staple cartridge (70). Knife member (80) includes a distally presented cutting edge (84) that is configured to sever tissue that is compressed between anvil (60) and deck (73) of staple cartridge (70) as knife member (80) translates distally through end effector (40). As noted above, knife member (80) also drives wedge sled (78) distally as knife member (80) translates distally through end effector (40), thereby driving staples (90) through tissue and against anvil (60) into formation.

C. Exemplary Actuation of End Effector

In the present example, anvil (60) is driven toward lower jaw (50) by advancing closure ring (36) distally relative to end effector (40). Closure ring (36) cooperates with anvil (60) through a camming action to drive anvil (60) toward lower jaw (50) in response to distal translation of closure ring (36) relative to end effector (40). Similarly, closure ring (36) may cooperate with anvil (60) to open anvil (60) away from lower jaw (50) in response to proximal translation of closure ring (36) relative to end effector (40). By way of example only, closure ring (36) and anvil (60) may interact in accordance with at least some of the teachings of U.S. Pub. No. 2014/0239036, entitled "Jaw Closure Feature for End Effector of Surgical Instrument," published Aug. 28, 2014, issued as U.S. Pat. No. 9,839,421 on Dec. 12, 2017, the disclosure of which is incorporated by reference herein; and/or in accordance with at least some of the teachings of U.S. patent application Ser. No. 14/314,108, entitled "Jaw Opening Feature for Surgical Stapler," tiled on Jun. 25, 2014, issued as U.S. Pat. No. 10,335,147 on Jul. 2, 2019, the disclosure of which is incorporated by reference herein.

As noted above, handle assembly (20) includes a pistol grip (22) and a closure trigger (24). As also noted above, anvil (60) is closed toward lower jaw (50) in response to distal advancement of closure ring (36). In the present example, closure trigger (24) is pivotable toward pistol grip (22) to drive closure tube (32) and closure ring (36) distally. Various suitable components that may be used to convert pivotal movement of closure trigger (24) toward pistol grip (22) into distal translation of closure tube (32) and closure ring (36) relative to handle assembly (20) will be apparent to those of ordinary skill in the art in view of the teachings herein.

Also, in the present example, instrument (10) provides motorized control of firing beam (82). In particular, instrument (10) includes motorized components that are configured to drive firing beam (82) distally in response to pivoting of firing trigger (26) toward pistol grip (22). In some versions, a motor (not shown) is contained in pistol grip (22) and receives power from battery pack (28). This motor is coupled with a transmission assembly (not shown) that converts rotary motion of a drive shaft of the motor into linear translation of firing beam (82). By way of example only, the features that are operable to provide motorized actuation of firing beam (82) may be configured and operable in accordance with at least some of the teachings of U.S. Pat. No. 8,210,411, entitled "Motor-Driven Surgical instrument," issued July 3, 2012, the disclosure of which is incorporated by reference herein.; U.S. Pat. No. 8,453,914, entitled "Motor-Driven Surgical Cutting Instrument with Electric Actuator Directional Control Assembly," issued Jun. 4, 2013, the disclosure of which is incorporated by reference herein; and/or U.S. patent application Ser. No. 14/226,142, entitled "Surgical Instrument Comprising a Sensor System," filed Mar. 26, 2014, issued as U.S. Pat. No. 9,913,642 on Mar. 13, 2018, the disclosure of which is incorporated by reference herein.

It should also be understood that any other components or features of instrument (10) may be configured and operable in accordance with any of the various references cited herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the references cited herein will be apparent to those of ordinary skill in the art. It should therefore be understood that the teachings below may be readily incorporated into the various instruments taught in the various references that are cited herein. It should also be understood that the below teachings are not limited to instrument (10) or devices taught in the references cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Exemplary Buttress Assembly for Surgical Stapler

In some instances, it may be desirable to equip end effector (40) with a buttress material to reinforce the mechanical fastening of tissue provided by staples (90). Such a buttress may prevent the applied staples (90) from pulling through the tissue and may otherwise reduce a risk of tissue tearing at or near the site of applied staples (90). In addition to or as an alternative to providing structural support and integrity to a line of staples (90), a buttress may provide various other kinds of effects such as spacing or gap-filling, administration of therapeutic agents, and/or other effects. In some instances, a buttress may be provided on deck (73) of staple cartridge (70). In some other instances, a buttress may be provided on the surface of anvil (60) that faces staple cartridge (70). It should also be understood that a first buttress may be provided on deck (73) of staple cartridge (70) while a second buttress is provided on anvil (60) of the same end effector (40). Various examples of forms that a buttress may take will be described in greater detail below. Various ways in which a buttress may be secured to a staple cartridge (70) or an anvil (60) will also be described in greater detail below.

A. Exemplary Composition of Buttress Assembly for Surgical Stapler

Figure 4:
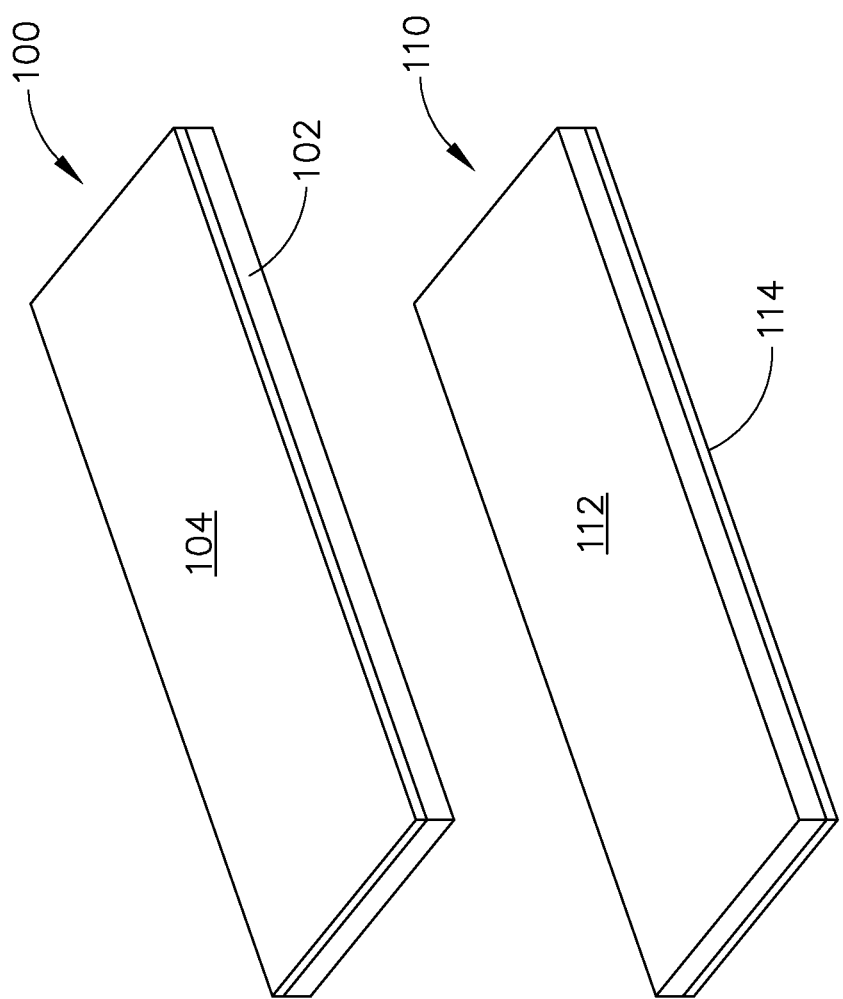
FIG. 4 depicts a perspective view of an exemplary upper buttress and an exemplary lower buttress, each of which may be applied to the end effector of FIG. 2.

FIG. 4 shows an exemplary pair of buttress assemblies (100, 110) with a basic composition. Buttress assembly (100) of this example comprises a buttress body (102) and an upper adhesive layer (104). Similarly, buttress assembly (110) comprises a buttress body (112) and a lower adhesive layer (114). In the present example, each buttress body (102, 112) comprises a strong yet flexible material configured to structurally support a line of staples (90). By way of example only, each buttress body (102, 112) may comprise a woven mesh of polyglactin 910 material by Ethicon, Inc. of Somerville, N.J. Alternatively, any other suitable materials or combinations of materials may be used in addition to or as an alternative to polyglactin 910 material to form each buttress body (102, 112). Each buttress body (102, 112) may take any other suitable form and may be constructed of any other suitable material(s). By way of further example only, each buttress body (102, 112) may comprise one or more of the following: NEOVEIL absorbable PGA felt by Gunze Limited, of Kyoto, Japan; SEAMGUARD polyglycolic acid:trimethylene carbonate (PGA:TMC) reinforcement material by W.L. Gore & Associates, Inc., of Flagstaff, Ariz.; PERI-STRIPS DRY with VERITAS Collagen Matrix (PSDV) reinforcement material, by Baxter Healthcare Corporation of Deerfield, Ill.; BIODESIGN biologic graft material by Cook Medical, Bloomington, Ind.; and/or SURGICEL NU-KNIT hemostat material by Ethicon, Inc. of Somerville, N.J. Still other suitable materials that may be used to form each buttress body (102, 112) will be apparent to those of ordinary skill in the art in view of the teachings herein.

In addition or in the alternative, each buttress body (102, 112) may comprise a material including, for example, a hemostatic agent such as fibrin to assist in coagulating blood and reduce bleeding at the severed and/or stapled surgical site along tissue (90). As another merely illustrative example, each buttress body (102, 112) may comprise other adjuncts or hemostatic agents such as thrombin may be used such that each buttress body (102, 112) may assist to coagulate blood and reduce the amount of bleeding at the surgical site. Other adjuncts or reagents that may be incorporated into each buttress body (102, 112) may further include but are not limited to medical fluid or matrix components. Merely illustrative examples of materials that may be used to form each buttress body (102, 112), as well as materials that may be otherwise incorporated into each buttress body (102, 112), are disclosed in U.S. patent application Ser. No. 14/667,842, entitled "Method of Applying a Buttress to a Surgical Stapler," filed Mar. 25, 2015, issued as U.S. Pat. No. 10,349,939 on Jul. 16, 2019 the disclosure of which is incorporated by reference herein. Alternatively, any other suitable materials may be used.

By way of further example only, each buttress body (102, 112) may be constructed in accordance with at least some of the teachings of U.S. Patent Pub. No. 2012/0241493, entitled "Tissue Thickness Compensator Comprising Controlled Release and Expansion," published Sep. 27, 2012, issued as U.S. Pat. No. 10,123,798 on Nov. 13, 2018, the disclosure of which is incorporated by reference herein; U.S. Patent Pub. No. 2013/0068816, entitled "Surgical Instrument and Buttress Material," published Mar. 21, 2013, now abandoned, the disclosure of which is incorporated by reference herein; U.S. Patent Pub. No. 2013/0062391, entitled "Surgical Instrument with Fluid tillable Buttress," published Mar. 14, 2013, issued as U.S. Pat. No. 9,999,408 on Jun. 19, 2018, the disclosure of which is incorporated by reference herein; U.S. Patent Pub. No. 2013/0068820, entitled "Fibrin Pad Matrix with Suspended Heat Activated Beads of Adhesive," published Mar. 21, 2013, issued as U.S. Pat. No. 8,814,025 on Aug. 26, 2014, the disclosure of which is incorporated by reference herein; U.S. Patent Pub. No. 2013/0082086, entitled "Attachment of Surgical Staple Buttress to Cartridge," published Apr. 4, 2013, issued as U.S. Pat. No. 8,899,464 on Dec. 2, 2014 the disclosure of which is incorporated by reference herein; U.S. Patent Pub. No. 2013/0037596, entitled "Device for Applying Adjunct in Endoscopic Procedure," published Feb. 14, 2013, issued as U.S. Pat. No. 9,492,170 on Nov. 15, 2016, the disclosure of which is incorporated by reference herein; U.S. Patent Pub. No. 2013/0062393, entitled "Resistive Heated Surgical Staple Cartridge with Phase Change Sealant," published. Mar. 14, 2013, issued as U.S. Pat. No. 8,998,060 on Apr. 7, 2015, the disclosure of which is incorporated by reference herein; U.S. Patent Pub. No. 2013/0075446, entitled "Surgical Staple Assembly with Hemostatic Feature," published Mar. 28, 2013, issued as U.S. Pat. No 9,393,018 on Jul. 19, 2016, the disclosure of which is incorporated by reference herein; U.S. Patent Pub. No. 2013/0062394, entitled "Surgical Staple Cartridge with Self-Dispensing Staple Buttress," published Mar. 14, 2013, issued as U.S. Pat. No. 9,101,359 on Aug. 11, 2015, the disclosure of which is incorporated by reference herein; U.S. Patent Pub. No. 2013/0075445, entitled "Anvil Cartridge for Surgical Fastening Device," published Mar. 28, 2013, issued as U.S. Pat. No. 9,198,644 on Dec. 1, 2015, the disclosure of which is incorporated by reference herein; U.S. Patent Pub. No. 2013/0075447, entitled "Adjunct Therapy for Applying Hemostatic Agent," published Mar. 28, 2013, now abandoned, the disclosure of which is incorporated by reference herein; U.S. Patent Pub. No. 2013/0256367, entitled "Tissue Thickness Compensator Comprising a Plurality of Medicaments," published Oct. 3, 2013, issued as U.S. Pat. No. 9,211,120 on Dec. 15, 2015, the disclosure of which is incorporated by reference herein; U.S. patent application Ser. No. 14/300,954, entitled "Adjunct Materials and Methods of Using Same in Surgical Methods for Tissue Sealing," filed Jun. 10, 2014, issued as U.S. Pat. No. 10,172,611 on Jan. 8, 2019, the disclosure of which is incorporated by reference herein; U.S. patent application Ser. No. 14/827,856, entitled "Implantable Layers for a Surgical Instrument," filed Aug. 17, 2015, published as U.S. Pub. No. 2017/0049444 on Feb. 23, 2017, the disclosure of which is incorporated by reference herein; U.S. patent application Ser. No. 14/840,613, entitled "Drug Eluting Adjuncts and Methods of Using Drug Eluting Adjuncts," filed Aug. 31, 2015, published as U.S. Pub. No. 2017/0055986 on Mar. 2, 2017, the disclosure of which is incorporated by reference herein; U.S. patent application Ser. No. 14/871,071, entitled "Compressible Adjunct with Crossing Spacer Fibers," filed Sep. 30, 2015, issued as U.S. Pat. No. 10,433,846 on Oct. 8, 2019, the disclosure of which is incorporated by reference herein; and/or U.S. patent application Ser. No. 14/871,131, entitled "Method for Applying an Implantable Layer to a Fastener Cartridge," filed Sep. 30, 2015, published as U.S. Pub. No. 2017/0086842 on Mar. 30, 2017, the disclosure of which is incorporated by reference herein.

In the present example, adhesive layer (104) is provided on buttress body (102) in order to adhere buttress body (102) to underside (65) of anvil (60), Similarly, adhesive layer (114) is provided on buttress body (112) in order to adhere buttress body (112) to deck (73) of staple cartridge (70). Adherence of the buttress body (102) to underside (65) of anvil (60) or to deck (73) of staple cartridge (70) can occur through a variety of mechanisms including but not limited to a pressure sensitive adhesive. In some versions, each adhesive layer (104, 114) comprise a pressure sensitive adhesive material. Examples of various suitable materials that may be used to form adhesive layers (104, 114) are disclosed in U.S. patent application Ser. No. 14/667,842, entitled "Method of Applying a Buttress to a Surgical Stapler," filed Mar. 25, 2015, issued as U.S. Pat. No. 10,349,939 on Jul. 16, 2019, the disclosure of which is incorporated by reference herein. Alternatively, any other suitable materials may be used. It should be understood that the term "adhesive," as used herein, may include (but is not limited to) tacky materials and also materials that are pliable or wax-like and adhere to a complex geometry via deformation and conformance. Some suitable adhesives may provide such pliability to adhere to a complex geometry via deformation and conformance without necessarily providing a high initial tack, some instances, adhesives with lower tackiness may be removed more cleanly from surfaces. Various suitable materials that may be used to form adhesive layers (104, 114) will be apparent to those of ordinary skill in the art in view of the teachings herein.

B. Exemplary Materials and Techniques for Providing Adhesion of Buttress to Surgical Stapler As noted above, a buttress assembly (100, 110) may include a layer (104, 114) of adhesive material (or other form of adhesive material) that adheres buttress body (102, 112) to either underside (65) of anvil (60) or deck (73) of staple cartridge (70). Such an adhesive material may provide proper positioning of buttress body (102, 112) before and during actuation of end effector (40); then allow buttress body (102, 112) to separate from end effector (40) after end effector (40) has been actuated, without causing damage to buttress body (102, 112) that is substantial enough to compromise the proper subsequent functioning of buttress body (102, 112).

FIGS. 5A-5C show a sequence where an end effector (40) that has been loaded with buttress assemblies (100, 110) is actuated to drive staples (90) through two apposed layers of tissue ($T_1$, $T_2$), with buttress assemblies (100, 110) being secured to the same layers of tissue ($T_1$, $T_2$) by staples (90). In particular, FIG. 5A shows layers of tissue ($T_1$, $T_2$) positioned between anvil (60) and staple cartridge (70), with anvil (60) in the open position. Buttress assembly (100) is adhered to the underside (65) of anvil (60) via adhesive layer (104); while buttress assembly (110) is adhered to deck (73) of staple cartridge (70) via adhesive layer (114). Layers of tissue ($T_1$, $T_2$) are thus interposed between buttress assemblies (100, 110). Next, trigger (24) is pivoted toward pistol grip (22) to drive closure tube (32) and closure ring (36) distally. This drives anvil (60) to the closed position as shown in FIG. 5B. At this stage, layers of tissue ($T_1$, $T_2$) are compressed between anvil (60) and staple cartridge (70), with buttress assemblies (100, 110) engaging opposite surfaces of tissue layers ($T_1$, $T_2$). End effector (40) is then actuated as described above, driving staple (90) through buttress assemblies (100, 110) and tissue (90). As shown in FIG. 5C, crown (92) of driven staple (90) captures and retains buttress assembly (110) against layer of tissue ($T_2$). Deformed legs (94) of staple (90) capture and retain buttress assembly (100) against layer of tissue ($T_1$).

Figure 6:
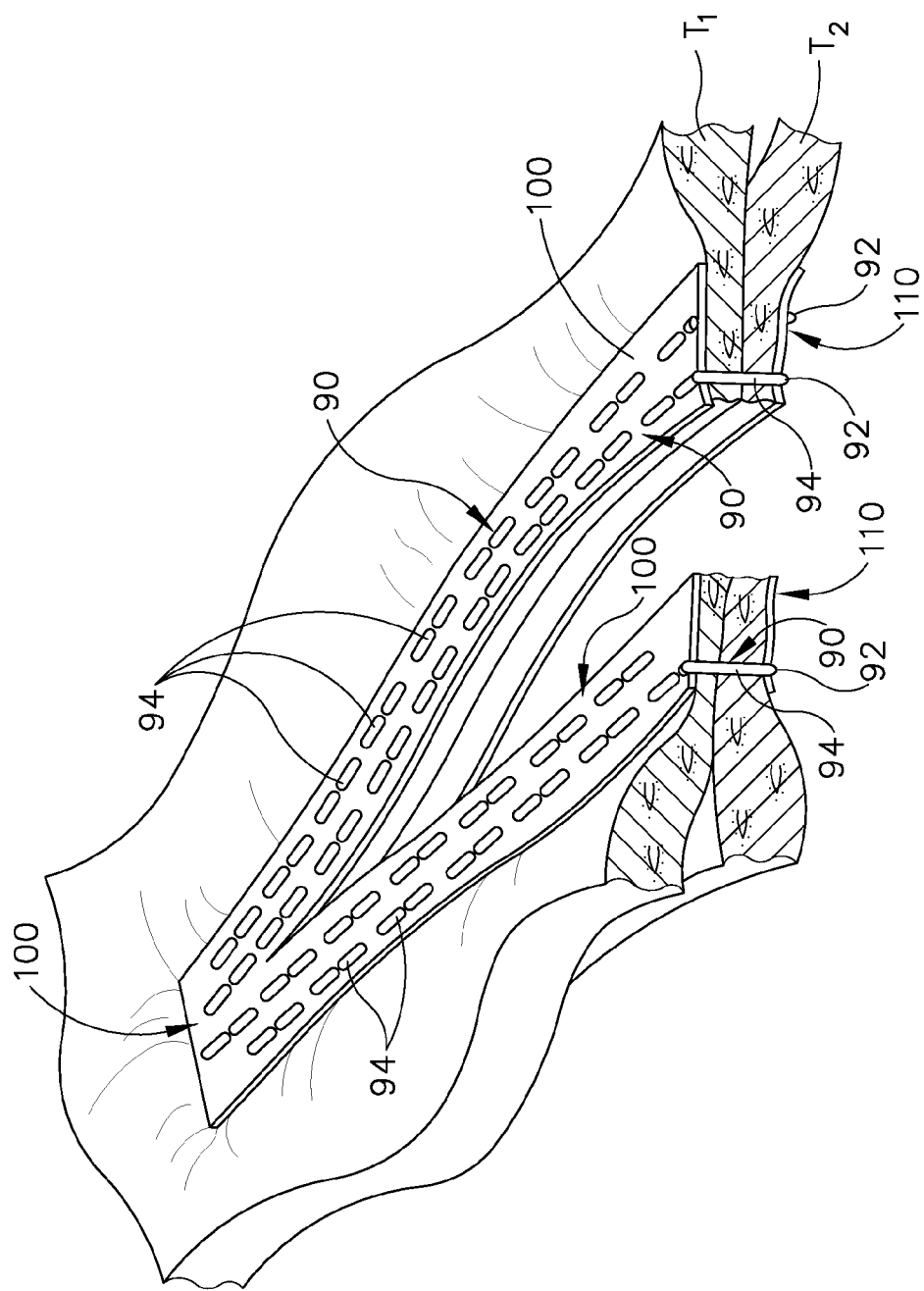
FIG. 6 depicts a perspective view of staples and the buttress assembly of FIG. 5A having been secured to the tissue by the end effector of FIG. 2.

It should be understood that a series of staples (90) will similarly capture and retain buttress assemblies (100, 110) against layers of tissue ($T_1$, $T_2$), thereby securing buttress assemblies (100, 110) to tissue ($T_1$, $T_2$) as shown in FIG. 6. As end effector (40) is pulled away from tissue (90) after deploying staples (90) and buttress assemblies (100, 110), buttress assemblies (100, 110) disengage end effector), such that buttress assemblies (100, 110) remain secured to tissue ($T_1$, $T_2$) with staples (90). Buttress tissue ($T_1$, $T_2$) thus provide structural reinforcement to the lines of staples (90). As can also be seen in FIG. 6, knife member (80) also cuts through a centerline of buttress tissue assemblies (100, 110), separating each buttress assemblies (100, 110) into a corresponding pair of sections, such that each section remains secured to a respective severed region of tissue ($T_1$, $T_2$).

In the foregoing example, buttress assembly (100) is sized to span across the full width of underside (65), such that buttress assembly (100) spans across channel (62). Thus, knife member (80) cuts through buttress assembly (100) during actuation of end effector (40) as described above. In some other examples, such as those described below, buttress assembly (100) is provided in two separate, laterally spaced apart portions, with one portion being disposed on one side of channel (62) and another portion being disposed on underside (65) on the other side of channel (62). In such versions, buttress assembly (100) does not span across channel (62), such that knife member (80) does not cut through buttress assembly (100) during actuation of end effector (40).

Likewise, buttress assembly (110) may be sized to span across the full width of deck (73), such that buttress assembly (110) spans across channel (72), and such that knife member (80) cuts through buttress assembly (110) during actuation of end effector (40) as described above. Alternatively, buttress assembly (110) may be provided in two separate, laterally spaced apart portions, with one portion being disposed on deck (73) on one side of channel (72) and another portion being disposed on deck (73) on the other side of channel (72), such that buttress assembly (110) does not span across channel (72), and such that knife member (80) does not cut through buttress assembly (110) during actuation of end effector (40).

III. Exemplary Alternative Buttress Assemblies with Features for Mechanically Coupling to Staple Cartridge In some instances, it may be desirable to deploy multiple, successive lines of staples (90) with buttress assemblies (100, 110) onto tissue during a surgical operation. Such a task may require the operator to remove end effector (40) from the patient (e.g., through a trocar), remove the spent staple cartridge (70), replace the staple cartridge (70), and re-insert end effector (40) into the patient via the trocar. Before end effector (40) is re-inserted into the patient, the operator may load a new buttress assembly (100) on anvil (60). In addition, the replacement staple cartridge (70) may include a new buttress assembly (110). In some such instances, knife member (80) may need to sever one or two new buttress assemblies (100, 110) each time end effector (40) is actuated. Deploying multiple successive lines of staples and buttress assemblies may thus cause stress and wear on knife member (80) and lead to operator fatigue. It may therefore desirable to reduce the amount of force required to actuate end effector (40), and reducing stress and wear on knife member (80), by reducing or eliminating structures that must be severed by knife member (80) during actuation of end effector (40). Several exemplary features that will prevent knife member (80) from having to sever buttress assembly (110) during actuation of end effector (40) are described below.

Some versions of buttress assemblies (100, 110) are removably secured to end effector (40) via an adhesive. Various examples of how adhesives may be used to secure buttress assemblies (100, 110) to end effector (40) are described in U.S. Patent App. No. 14/667,842, entitled "Method of Applying a Buttress to a Surgical Stapler," filed Mar. 25, 2015, issued as U.S. Pat. No. 10,349,939 on Jul. 16, 2019, the disclosure of which is incorporated by reference herein. It may be desirable to secure buttress assemblies (100, 110) to end effector (40) using something other than adhesives. Various mechanical features that may be used to removably secure buttress assembly (110) to staple cartridge (70) will be described in greater detail below. It should be understood that similar features may be used to secure buttress assembly (100) to anvil (60). It should also be understood that buttress assemblies (100, 110) may otherwise be configured and operable in accordance with at least some of the teachings of U.S. patent application Ser. No. 14/667,842, entitled "Method of Applying a Buttress to a Surgical Stapler," filed Mar. 25, 2015, issued as U.S. Pat. No. 10,349,939 on Jul. 16, 2019, the disclosure of which is incorporated by reference herein.

A. Buttress Assembly Including Retention Tabs

Figure 7:
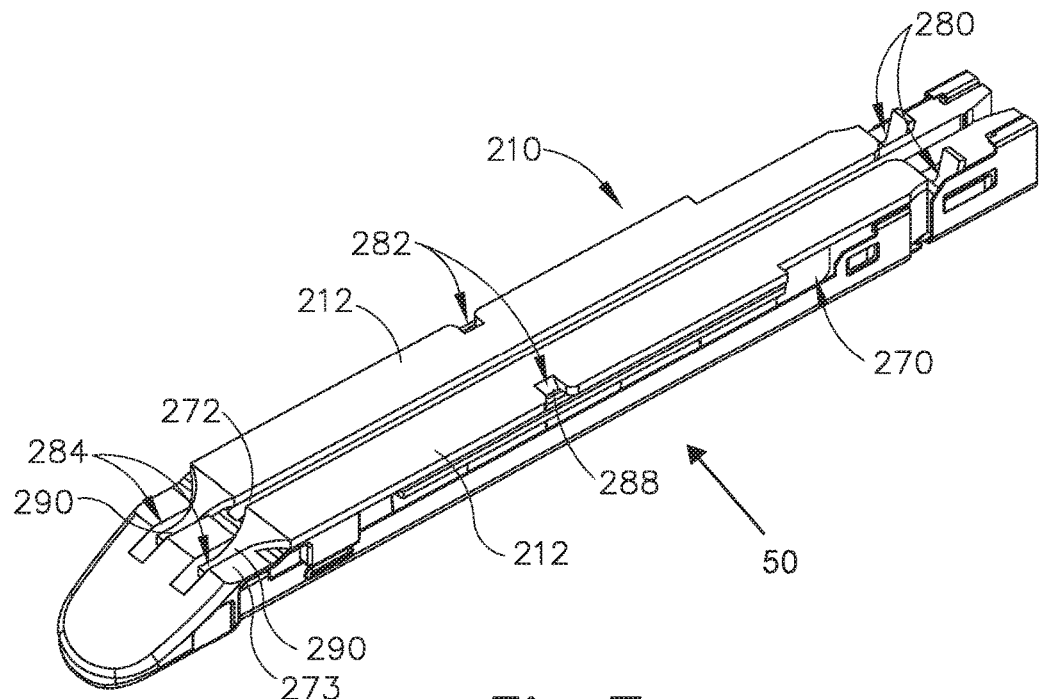
FIG. 7 depicts a perspective view of another exemplary alternative staple cartridge incorporated into the lower jaw of end effector of instrument of FIG. 1, including an exemplary alternative buttress assembly.

FIG. 7 shows an exemplary alternative buttress assembly (210) removably coupled to an exemplary alternative staple cartridge (270). In the example shown, buttress assembly (210) is releasably and mechanically coupled to cartridge (270) rather than being adhesively bonded to cartridge (270). Buttress assembly (210) includes a pair of opposing buttress bodies (212). Buttresses bodies (212) may be configured to be substantially similar to buttress bodies (100, 112) described above. It should be understood that upon actuation of end effector (40), a series of staples (90) will similarly capture and retain buttress assembly (210) against layers of tissue ($T_1$, $T_2$), thereby securing buttress assembly (210) to tissue ($T_1$, $T_2$) in a similar manner as shown in FIG. 6. In some examples, buttress assembly (210) may be utilized in conjunction with buttress assembly (100) on anvil (60) such that a series of staples (90) will similarly capture and retain buttress assemblies (100, 210) against layers of tissue ($T_1$, $T_2$), thereby securing buttress assemblies (100, 210) to tissue ($T_1$, $T_2$) in a similar manner as shown in FIG. 6.

In the present example, one buttress body (212) is disposed on deck (273) on one side of channel (272) and the other buttress body (212) is disposed on deck (273) on the other side of channel (272), such that buttress assembly (210) does not span across channel (272), and such that knife member (80) does not cut through buttress assembly (210) during actuation of end effector (40), thus potentially reducing the force required by an operator to actuate end effector (40).

Figure 8:
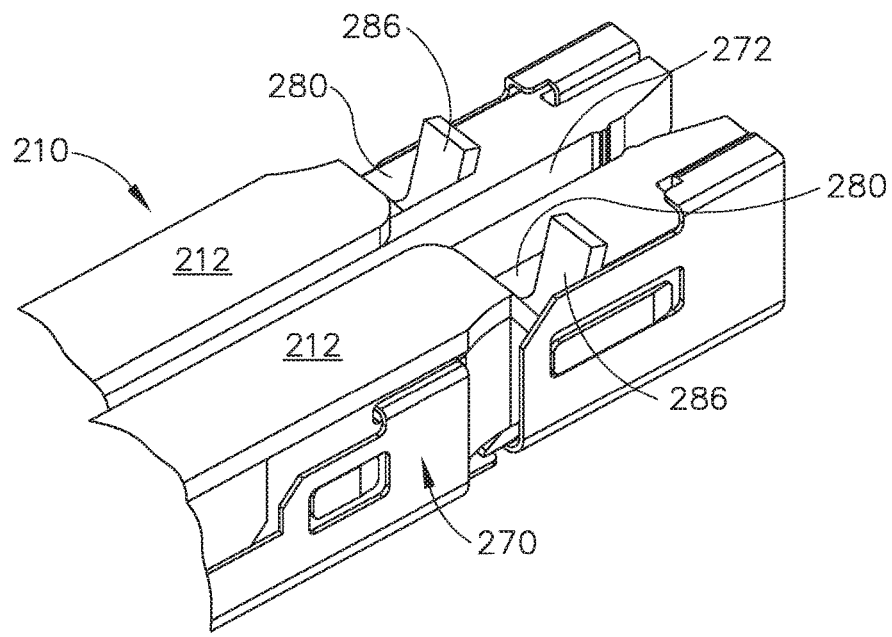
FIG. 8 depicts a detailed perspective view of the staple cartridge and buttress assembly of FIG. 7, showing retention features for releasably coupling the buttress assembly to the staple cartridge.

Staple cartridge (270) is removably coupled to lower jaw (50) of end effector (40). Staple cartridge (270) is substantially similar to staple cartridge (70) except for that staple cartridge (270) includes a plurality of recesses (280, 282, 284) for removably receiving corresponding retention features (286, 288, 290) on buttresses (212a, 212b). As shown best in FIGS. 9A-9B, retention feature (286) comprises a U-shaped tab extending from a rear portion of each buttress body (212) in a direction parallel to channel (272). Tab (286) is configured to fit at least partially within recess (280). As best seen in FIG. 8, tab (286) is configured to press fit within recess (280) when tab (286) is directed into recess (280). It should be understood that tab (286) may comprise a resilient material that provides a bias for the press fit.

Retention feature (288) comprises a tab extending away from channel (272), at an oblique angle relative to a plane defined by the faces of buttresses (212a, 212b) and downwardly relative to (i.e., toward) cartridge (270). Tab (288) is configured to press fit within recess (282) when tab (286) is directed into recess (282). In some versions, tab (288) comprises a resilient material that provides a bias for the press fit.

Retention feature (290) comprises a tab extending from a distal end of buttress (212) in a direction that is generally parallel to slot (272). Tabs (286, 288, 290) of the present example are configured to press fit into slots (280, 282, 284), respectively, but in other examples tabs (286, 288, 290) may be retained relative to slots (280, 282, 284) in other suitable manners, such as resilient snap fitting, for example. In some examples, recesses may (280, 282) include a portion that extends inwardly from an outer portion of recess toward slot (272) in order to create further interference with tabs (286, 288), respectively. Similarly, in some examples, recesses (284) may include one or more portions that extend inwardly toward a middle of recesses (284) that create further interference with tabs (290). Other suitable configurations of recesses (280, 282, 284) and tabs (286, 288, 290) will be apparent to persons skilled in the art in view of the teachings herein.

In the present example, any or all of tabs (286, 288, 290) comprise the same material or materials as buttress bodies (212). In other examples, any or all of tabs (286, 288, 290) may comprise a plurality of laminate, bioabsorbable layers, which may or may not include a layer that comprises part of buttress bodies (212). Other suitable configurations and materials that tabs (286, 288, 290) may comprise will be apparent to persons skilled in the art in view of the teachings herein.

The retention force provided between retention features (286, 288, 290) and recesses (280, 282, 284) is sufficient to maintain the removable coupling between buttress assembly (210) and cartridge (270) absent a sufficient decoupling force. However, buttress assembly (210) is configured to decouple from cartridge (270) in response to a sufficient decoupling force input, as discussed in more detail below. As discussed above with respect to the similarly operable staple cartridge (70), a wedge sled (78) translates longitudinally through cartridge (270) in order to drive staples (90) upwardly toward anvil (60). In the present example, recesses (280, 282) are positioned such that camming surface (79) of wedge sled (78) will to contact tabs (286, 288) as wedge sled (78) translates through cartridge (270), and thereby urge contact tabs (286, 288) upwardly out of engagement with recesses (280, 282), to assist in decoupling buttress assembly (210) from cartridge (270).

Figure 9A:
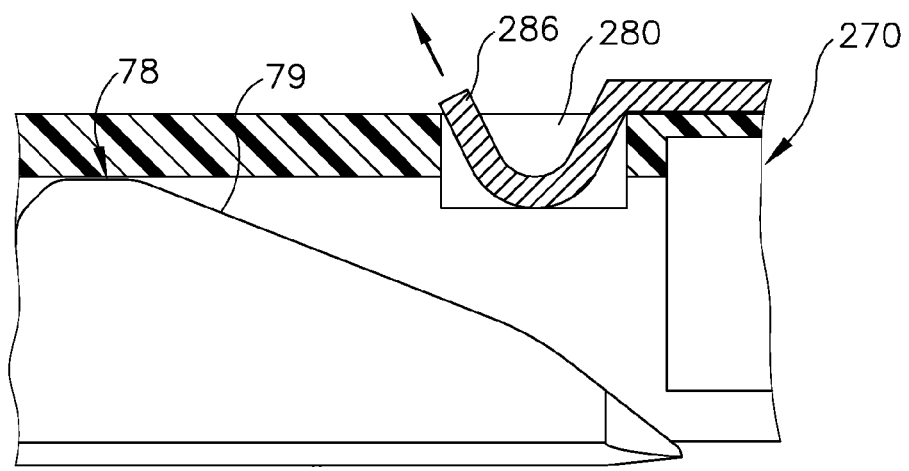
FIG. 9A depicts a partial cross-sectional side view of the staple cartridge and buttress assembly of FIG. 7, showing the retention features coupling the buttress assembly to the staple cartridge.
Figure 9B:
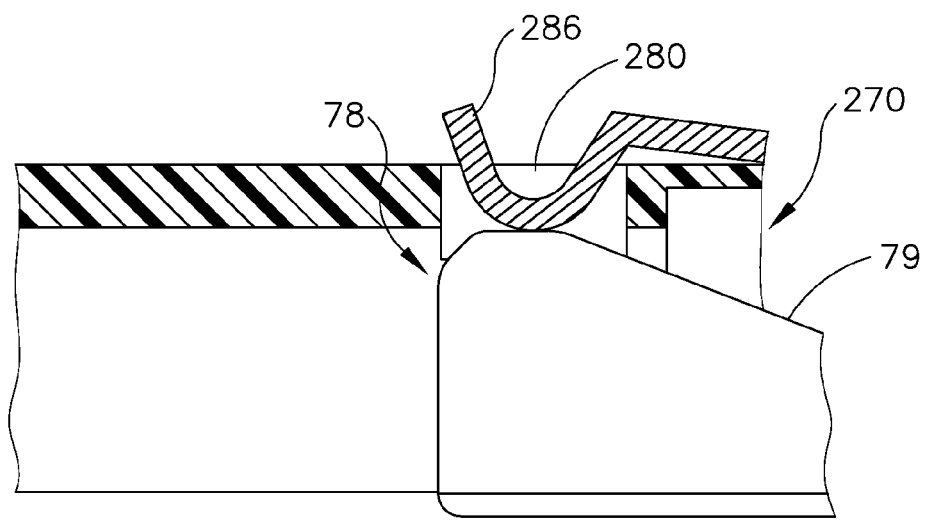
FIG. 9B depicts a partial cross-sectional side view of the staple cartridge and buttress assembly of FIG. 7, showing the retention features having been decoupled to release the buttress assembly from the staple cartridge.

More particularly, as shown in the transition from FIG. 9A to FIG. 9B, as wedge sled (78) translates longitudinally through cartridge (70) as discussed above, cam surface (79) of sled (78) is urged against tab (286), thus urging tab (286) out of recess (280) and away from cartridge (270). As sled (78) advances further longitudinally, cam surface (79) of wedge sled (78) is urged against tab (288), thus urging tab (288) and a more distal portion of buttress assembly (210) out of recess (282) and away from cartridge (270). Thus, the upward camming force provided by cam surface (79) of sled (78) assists in releasing buttress assembly (210) from cartridge (270) such that the release of buttress assembly (210) from cartridge (270) does not rely mostly or entirely on being captured by staples (90). In some examples, however, the upward force associated with being captured by staples (90) may be sufficient to release buttress assembly (210) from cartridge (270). Tabs (290) are released from recesses (284) as the more distal portions of buttress bodies (212) are captured by staples (90).

B. Buttress Assemblies Including Slots for Engaging with Connector Members on Cartridge Deck FIGS. 10-14 show an exemplary alternative buttress assembly (310) comprising a buttress body (312) that is removably coupled to an exemplary alternative staple cartridge (370). In the example shown, buttress assembly (310) is releasably and mechanically coupled to cartridge (370) rather than being adhesively bonded to cartridge (370). Buttress body (312) may be configured to be substantially similar to buttress (112) described above. It should be understood that upon actuation of end effector (40), a series of staples (90) will similarly capture and retain buttress assembly (310) against layers of tissue ($T_1$, $T_2$), thereby securing buttress assembly (310) to tissue ($T_1$, $T_2$) in a similar manner as shown in FIG. 6. In some examples, buttress assembly (310) may be utilized in conjunction with buttress assembly (100) on anvil (60) such that a series of staples (90) will similarly capture and retain buttress assemblies (100, 310) against layers of tissue ($T_1$, $T_2$), thereby securing buttress assemblies (100, 310) to tissue ($T_1$, $T_2$) in a similar manner as shown in FIG. 6.

Cartridge (370) is removably coupled to lower jaw (50) of end effector (40). Cartridge (370) is configured to be substantially similar to cartridge (70) discussed above, except for that cartridge (370) includes connector members (380) at opposing portions of cartridge deck (373) that, as discussed in further detail below, releasably and mechanically couple buttress assembly (310) to cartridge deck (373).

Figure 12:
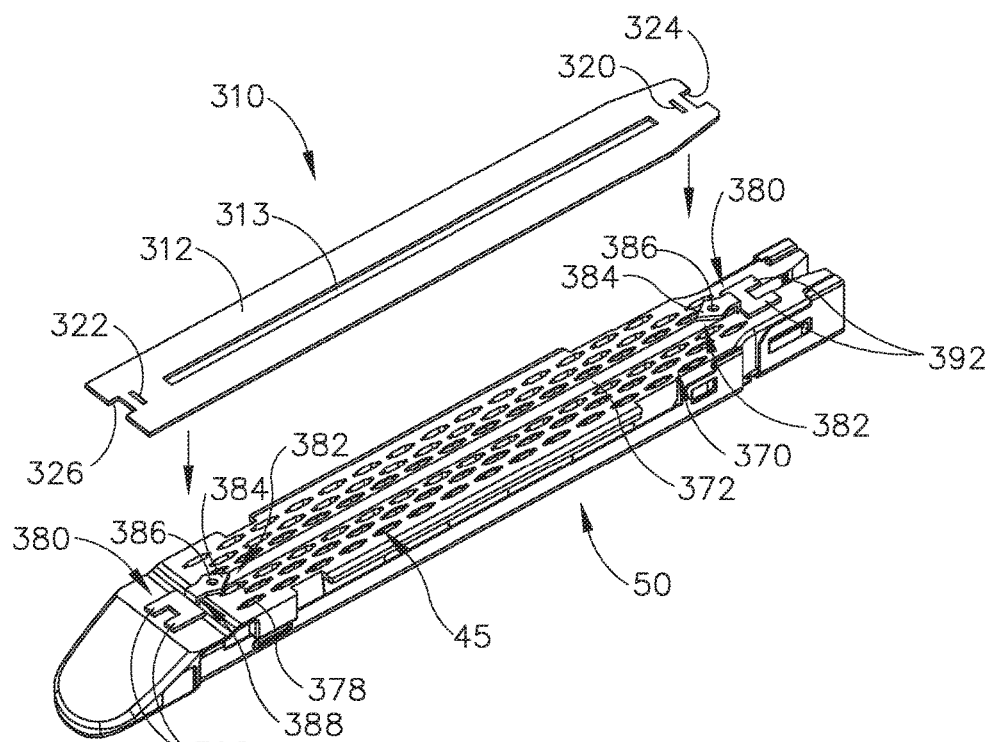
FIG. 12 depicts a perspective view of an exemplary alternative staple cartridge incorporated into the lower jaw of end effector of instrument of FIG. 1, showing the connector portion of FIG. 10 and the buttress assembly of FIG. 11.

As best seen in FIGS. 11-12, buttress (312) comprises a proximal end (314), a distal end (316), with a tapered portion (318) toward proximal end (314). Buttress (312) also includes an elongate slot (313) extending between the proximal and distal ends, a rectangular proximal recess (324), and a rectangular distal recess (326). Slot (313) and recesses (324, 326) are positioned and configured to correspond to channel (372), such that the majority of buttress (312) does not span across channel (372), and such that knife member (80) does not cut through buttress (312) during actuation of end effector (40). Buttress (312) further includes a proximal slot (320) and a distal slot (322) which, as discussed below, are configured assist in coupling buttress (312) to cartridge (370). In the present example, slots (320, 322) extend perpendicularly relative to a longitudinal axis (327) of buttress body (312).

As best seen in FIG. 10, connector member (380) includes a first end (382) with a head (384) including an aperture (386), a notch (387), a middle portion (388), and a second end (390) including opposing legs (392). In the present example, head (384) has a diamond shape, though it should be understood that head (384) may have any other suitable shape, including but not limited to the shapes of the various exemplary alternative heads (884a-884l) shown in FIGS. 19-30. In the present example, connector members (380) are bonded to cartridge deck (373) by various suitable methods including, but not limited to, adhesives. In addition or in the alternative, legs (392) may be fitted into corresponding slots (not shown) in cartridge (370) and may be secured in those slots using any suitable features and techniques as will be apparent to those of ordinary skill in the art in view of the teachings herein. As shown, connector member (380) at the proximal end of cartridge (370) is oriented such that head (384) points in a distal direction, and connector member (380) at the distal end of cartridge (370) is oriented such that head (384) points in a proximal direction.

Figure 13:
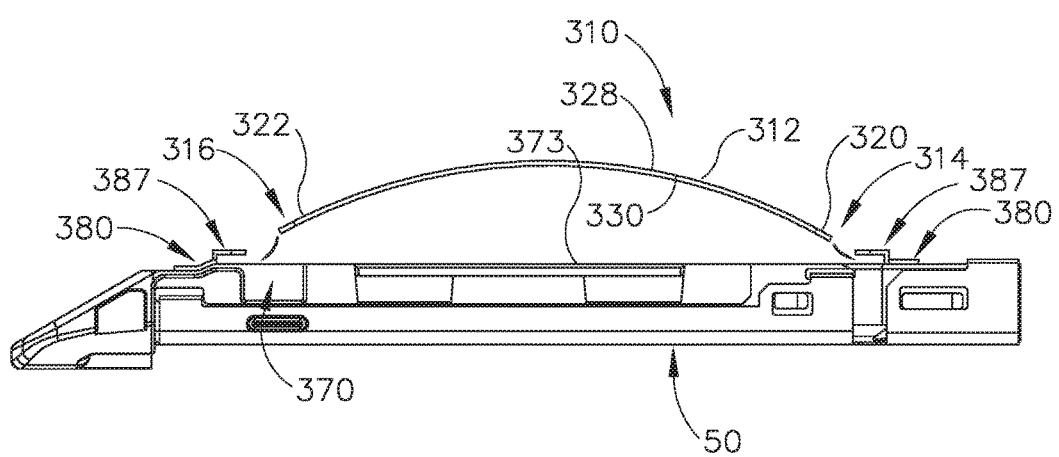
FIG. 13 depicts a side elevational view of the staple cartridge of FIG. 12, showing the buttress assembly of FIG. 11 being directed into engagement with the connector portions of FIG. 10.
Figure 14:
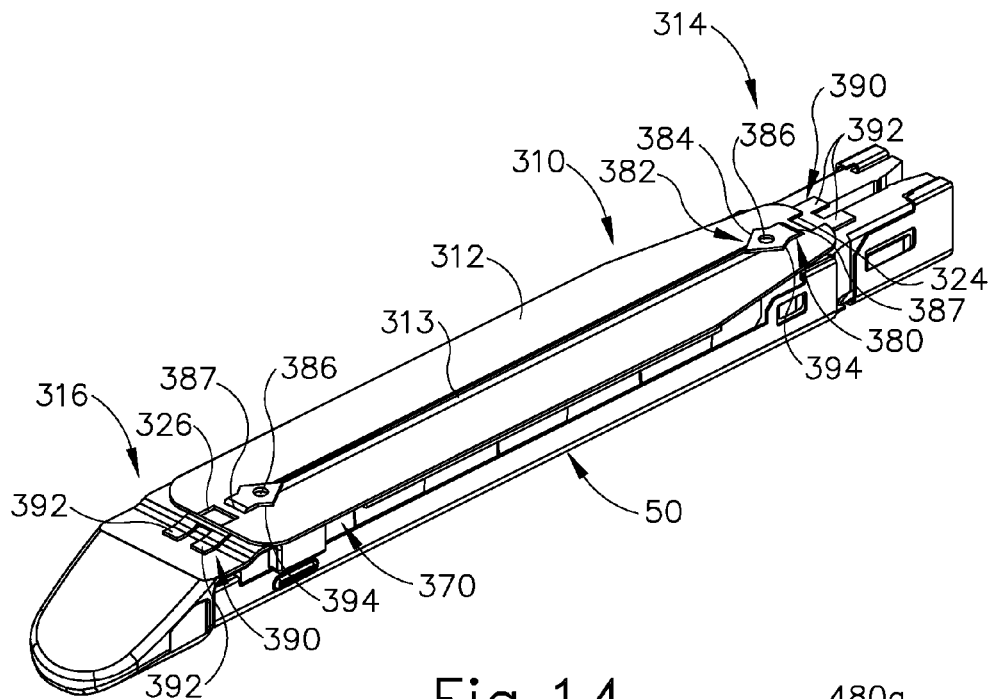
FIG. 14 depicts a perspective view of another exemplary alternative staple cartridge incorporated into the lower jaw of end effector of instrument of FIG. 1, including another exemplary alternative buttress assembly and connector portion.

FIG. 13 shows one manner of removably coupling buttress body (312) to connector portions (380). As shown, an operator may direct the proximal end (314) of buttress body (312) toward connector portion (380) such that head (384) enters slot (320) (in a direction parallel to axis (327)) on second side (330) of buttress body (312), until a trailing edge (394) of connector portion (380) extends out of slot (320). Similarly, an operator may direct the distal end (316) of buttress (312) toward the other connector portion (380) such that head (384) enters slot (322) (in a direction parallel to axis (327)) on first side of buttress body (312), until a trailing edge (394) of connector portion (380) extends out of slot (322), and slot (322) engages with notch (387). Due to the configuration of slots (320, 322) and head (384), proximal end (314) of buttress body (312) is substantially prevented from moving in the proximal direction, and distal end (316) of buttress body (312) is substantially prevented from moving in the distal direction. Thus, the releasable mechanical coupling between buttress body (312) and connector portions (380) substantially prevents proximal and distal movement of buttress body (312).

The retention force provided by the engagement between connector portions (380) and slots (320, 322) is sufficient to maintain the removable coupling between buttress assembly (310) absent a sufficient decoupling force. However, buttress assembly (310) is configured to decouple from cartridge (370) in response to a sufficient decoupling force input. In the present example, the upward force associated with being captured by staples (90) provides sufficient decoupling force to release buttress assembly (310) from connector portions (380) of cartridge (370), as discussed in further detail below.

As noted above, due to the presence of elongate slot (313), one portion of buttress body (312) is disposed on deck (373) on one side of channel (372) and another portion of buttress body (312) is disposed on deck (373) on the other side of channel (372), such that only a portion of buttress body (312) spans across channel (372). Therefore, the effort required to actuate end effector (40) and sever and staple tissue is reduced. As end effector (40) is actuated and staples (90) capture buttress body (312), the portion of buttress body (312) near slot (320) is driven upwardly and slips out of engagement with connector portion (380). Substantially contemporaneously, knife member (80) may sever the portion of buttress body (312) near slot (320) as well as connector portion (380). By way of example only, connector portion (380) may be constructed of any suitable material that may be severed by knife member (80), including but not limited to a thin plastic film, a non-woven mesh, a paper-like material, and/or any other suitable kind(s) of material(s) having any suitable form as will be apparent to those of ordinary skill in the art in view of the teachings herein. As knife member (80) and sled (78) travel further longitudinally, proximal portion of buttress body (312) is captured by staples (90) and subjected to a sufficient decoupling force, and is thus urged away from and out of engagement with other connector portion (380).

FIGS. 15-18 show exemplary alternative buttress assemblies (410, 510, 610, 710), connector portions (480, 580, 680, 780), and staple cartridges (470, 570, 670, 770), respectively, that are configured to operate substantially similarly to buttress assembly (310), connector portion (380), and staple cartridge (70, 370), except for the differences below. In each of the examples shown in FIGS. 15-18, cartridges (470, 570, 670, 770) are removably coupled to lower jaw (50) of end effector (40). It should be understood that upon actuation of end effector (40), a series of staples (90) will similarly capture and retain buttress assembly (410, 510, 610, 710) against layers of tissue ($T_1$, $T_2$), thereby securing buttress assembly (410, 510, 610, 710) to tissue ($T_1$, $T_2$) in a similar manner as shown in FIG. 6. In some examples, buttress assembly (410, 510, 610, 710) may be utilized in conjunction with buttress assembly (100) on anvil (60) such that a series of staples (90) will similarly capture and retain buttress assembly (100) and a buttress assembly (410, 510, 610, 710) against layers of tissue ($T_1$, $T_2$), thereby securing buttress assemblies (100) and buttress assembly (410, 510, 610, 710) to tissue ($T_1$, $T_2$) in a similar manner as shown in FIG. 6.

Figure 15:
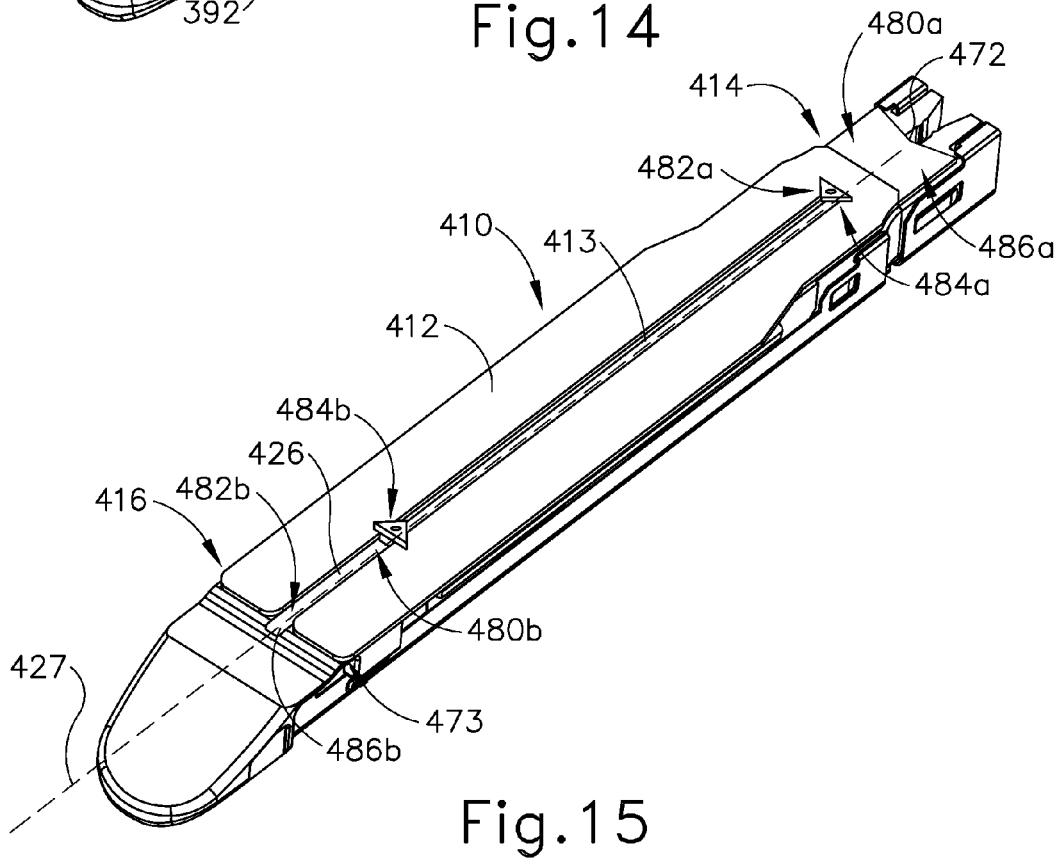
FIG. 15 depicts a perspective view of another exemplary alternative staple cartridge incorporated into the lower jaw of end effector of instrument of FIG. 1, including another exemplary alternative buttress assembly and connector portion.

As shown in FIG. 15, two connector portions (480a, 480b) are adhesively bonded to cartridge deck (473), though other manners of coupling connector portions (480a, 480b) to deck (473) will be apparent to persons skilled in the art in view of the teachings herein. In the example shown, proximal connector portion (480a) includes a first end (482a) with a head (484a) that is triangularly shaped. Alternative examples of head (484a) may include any other suitable shape, including the shapes of any one of alternative heads (884a-8841) shown in FIGS. 19-30. Second end (486a) includes a tapered portion to accommodate the shape of lower jaw (50), as well for the travel of knife member (80) through channel (472). Similarly, distal connector portion (480b) includes a first end (482b) with a head (484b) that is triangularly shaped. Alternative examples of head (484b) may include any other suitable shape, including the shapes of any one of alternative heads (884a-8841) shown in FIGS. 19-30. Second end (486b) includes a shape that is substantially similar to an end portion of cartridge (470) and covers a distal portion of channel (472).

Buttress body (412) includes an elongate slot (413) extending between a proximal end (414) and a distal end (416). Although not shown, buttress body (412) includes proximal and distal slots (similar to proximal and distal slots (320, 322)) that extend perpendicularly relative to axis (427) of buttress body (412). Buttress body (412) of the present example includes a distal recess (426) that is longer than distal recess (326). Buttress body (412) may be removably coupled to cartridge (470) via connector portions (480a, 480b) in a similar manner as buttress body (312) and connector portions (380). That is, buttress body (412) may be directed into engagement with a first one of the connector portions (480a, 480b) such that that one of the heads (484a, 484b) enters a respective one of the slots (in a direction parallel to axis (427)) on first side of buttress body (312) and the slot engages with notch (not shown). Then, another side of buttress body (412) may be directed into engagement with a second one of the connector portions (480a, 480b) such that that one of the heads (484a, 484b) enters a respective one of the slots (in a direction parallel to axis (427)), and the other slot engages with notch (not shown). Due to the configuration of slots and heads (484a, 484b), proximal end (414) of buttress body (412) is substantially prevented from moving in the proximal direction, and distal end (416) of buttress body (412) is substantially prevented from moving in the distal direction. Thus, the releasable mechanical coupling between buttress body (412) and connector portions (480a, 480b) substantially prevents proximal and distal movement of buttress body (412).

The retention force provided by the engagement between connector portions (480a, 480b) and slots (420, 422) is sufficient to maintain the removable coupling between buttress assembly (410) and cartridge (470) absent a sufficient decoupling force. However, buttress assembly (410) is configured to decouple from cartridge (470) in response to a sufficient decoupling force input. In the present example, the upward force associated with being captured by staples (90) provides sufficient decoupling force to release buttress assembly (410) from connector portions (480a, 480b) of cartridge (470), as discussed in further detail below.

As shown, one portion of buttress body (412) is disposed on deck (473) on one side of channel (472) and another portion of buttress body (412) is disposed on deck (473) on the other side of channel (472), such that only a portion of buttress body (312) spans across channel (472). Therefore, the effort required to actuate end effector (40) and sever and staple tissue is reduced. As end effector (40) is actuated and staples (90) capture buttress body (412), the portion of buttress body (412) near the proximal slot and connector portion (480a) is driven upwardly and slips out of engagement with connector portion (480a). Substantially contemporaneously, knife member (80) may sever the portion of buttress body (412) near connector portion (480a), as well as connector portion. As knife member (80) and sled (78) travel further longitudinally, proximal portion of buttress body (312) is captured by staples (90) and is thus urged away from and out of engagement with other connector portion (480b). However, due to the more proximal position of connector portion (480b) (relative to the example shown in FIG. 14), connector portion (480b) may also be severed as knife member (80) and sled (78) advance longitudinally further.

Figure 16:
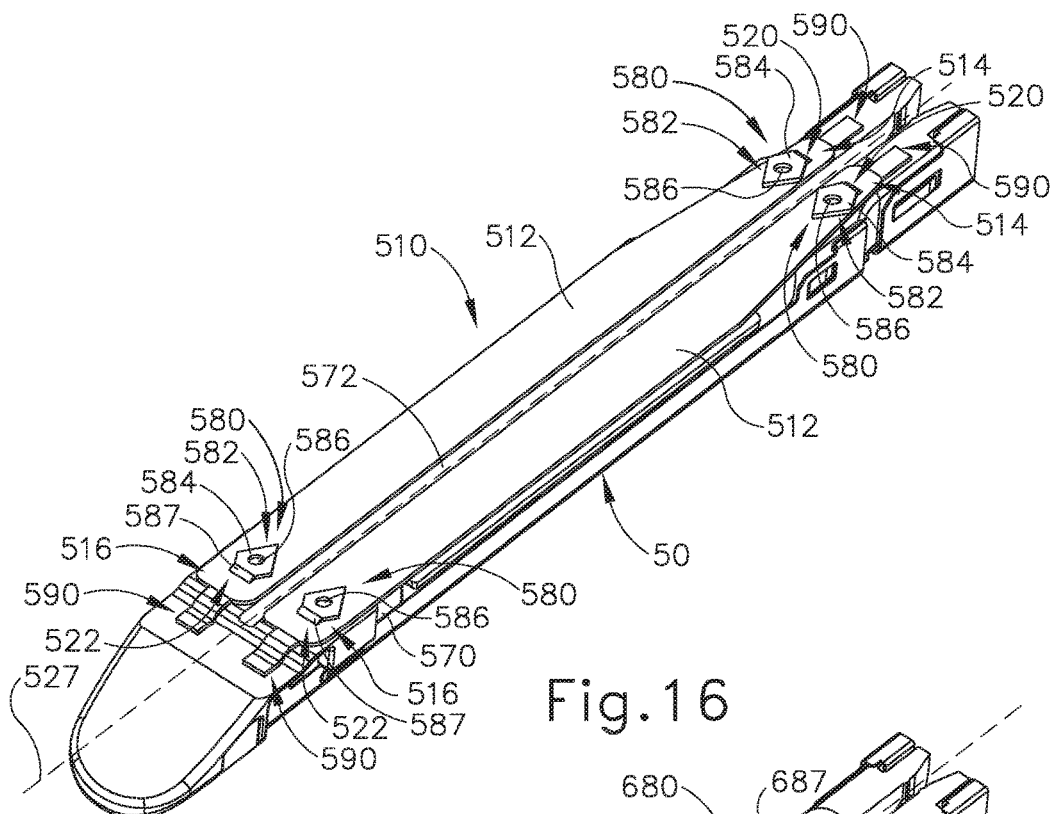
FIG. 16 depicts a perspective view of another exemplary alternative staple cartridge incorporated into the lower jaw of end effector of instrument of FIG. 1, including another exemplary alternative buttress assembly and connector portion.

Referring to FIG. 16, buttress assembly (510) includes a pair of buttress bodies (512). As shown, one buttress body (512) is disposed on deck (573) on one side of channel (572) and the other buttress body (512) is disposed on deck (573) on the other side of channel (572), such that buttress assembly (510) does not span across channel (572), and such that knife member (80) does not sever buttress assembly (210) during actuation of end effector (40), thus potentially reducing the force required by an operator to actuate end effector (40). In the example shown, buttress bodies (512) each include a proximal slot (520) and a distal slot (522) extending perpendicularly relative to axis (527) of buttress assembly (510).

Staple cartridge (570) includes exemplary alternative connector members (580) on each side of channel (572) and at each end of cartridge (570). As shown, each connector member (580) includes a first end (582) with a head (584) including an aperture (586), a notch (587), and a second end portion (590). Alternative examples of head (584) may include any other suitable shape, including the shapes of any one of alternative heads (884a-8841) shown in FIGS. 19-30.

To couple a buttress body (512) to a set of connector portions (580), proximal end (514) of buttress body (512) may be directed toward connector portion (580) such that head (584) enters slot (520) (in a direction parallel to axis (527)) on second side of buttress body (512), until a trailing edge of connector portion (580) extends out of slot (520) and slot (520) engages with notch (587). Similarly, an operator may direct the distal end (516) of buttress (512) toward the other connector portion (580) such that head (584) enters slot (522) (in a direction parallel to axis (527)) on first side of buttress body (512), until a trailing edge of connector portion (580) extends out of slot (522), and slot (522) engages with notch (587). As shown, connector member (380) at the proximal end of cartridge (570) is oriented such that head (584) points in a distal direction, and connector member (580) at the distal end of cartridge (570) is oriented such that head (584) points in a proximal direction. Due to the configuration of slots (520, 522) and head (584), proximal end (514) of buttress body (512) is substantially prevented from moving in the proximal direction, and distal end (516) of buttress body (512) is substantially prevented from moving in the distal direction. Thus, the releasable mechanical coupling between buttress bodies (512) and connector portions (580) substantially prevents proximal and distal movement of buttress body (512).

The retention force provided by the engagement between connector portions (580) and slots (520, 522) is sufficient to maintain the removable coupling between buttress assembly (510) and cartridge (570) absent a sufficient decoupling force. However, buttress assembly (510) is configured to decouple from cartridge (570) in response to a sufficient decoupling force input. In the present example, the upward force associated with being captured by staples (90) provides sufficient decoupling force to release buttress assembly (510) from connector portions (580) of cartridge (570), as discussed in further detail below.

As shown, one buttress body (512) is disposed on deck (573) on one side of channel (572) and another portion of buttress body (512) is disposed on deck (573) on the other side of channel (572), such that no portion of buttress bodies (512) spans across channel (572). Therefore, the effort required to actuate end effector (40) and sever and staple tissue is reduced. As end effector (40) is actuated and staples (90) capture buttress body (512), the portion of buttress body (512) near the proximal slot (520) and connector portions (580) is driven upwardly and slips out of engagement with connector portion (580). As knife member (80) and sled (78) travel further longitudinally, proximal portion (514) of buttress body (512) is captured by staples (90) and the portion of buttress body (512) near the distal slot (522) is driven upwardly and slips out of engagement with connector portion (580). Due to the positions of the buttress bodies (512) and connector portions (580) away from channel (572), knife member (580) does not sever any of buttress bodies (512) or connector portions.

Figure 17:
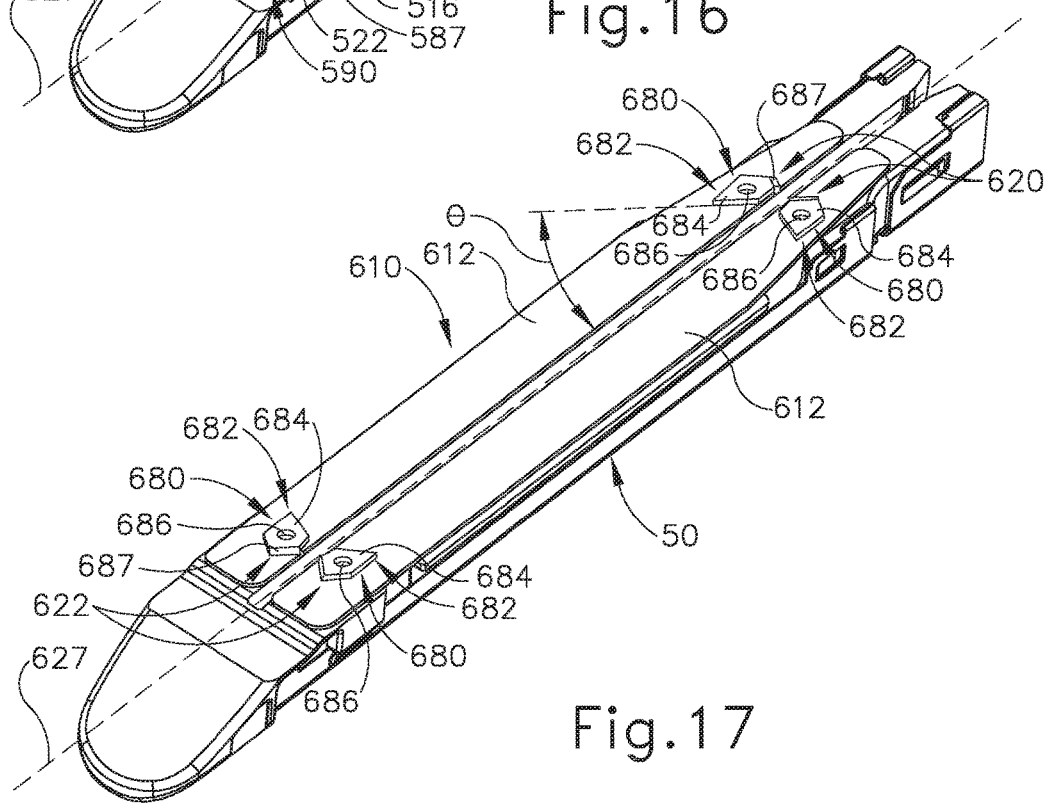
FIG. 17 depicts a perspective view of another exemplary alternative staple cartridge incorporated into the lower jaw of end effector of instrument of FIG. 1, including another exemplary alternative buttress assembly and connector portion.

FIG. 17 shows another exemplary alternative buttress assembly (610) in combination with an exemplary alternative staple cartridge (670) including exemplary alternative connector portions (680). Buttress assembly (610) is substantially identical to buttress assembly (510) discussed above, except for that buttress bodies (612) include slots (620, 622) that extend at an oblique angle (θ) relative to the longitudinal axis (627) of buttress assembly (610).

Staple cartridge (670) includes exemplary alternative connector members (680), each of which extends partially along channel (672) in a manner so as not to impede traversal of knife member (80) therethrough. As shown, each connector member (580) includes a first end (682) with a head (684) including an aperture (686), a notch (687), and a second end portion (not shown) extending downwardly relative to staple deck (673) Alternative examples of head (684) may include any other suitable shape, including the shapes of any one of alternative heads (884a-8841) shown in FIGS. 19-30.

To couple a buttress body (612) to a set of connector portions (680), proximal end (614) of buttress body (612) is directed toward connector portion (680) such that head (384) enters slot (620) (in a direction transverse to axis (627)) on second side of buttress body (612), until a trailing edge of connector portion (680) extends out of slot (620) and slot (620) engages with notch (687). Similarly, an operator may direct the distal end (616) of buttress (612) toward the other connector portion (680) such that head (684) enters slot (622) (in a direction transverse to axis (627)) on first side of buttress body (612), until a trailing edge of connector portion (680) extends out of slot (622), and slot (622) engages with notch (687). As shown, connector member (680) at the proximal end of cartridge (670) is oriented such that head (684) points in a distal direction at angle (θ) relative to axis (627), and connector member (680) at the distal end of cartridge (670) is oriented such that head (684) points in a proximal direction at an angle (θ) relative to axis (627). Due to the configuration of slots (620, 622) and head (684), proximal end (614) of buttress body (612) is substantially prevented from moving in the proximal and distal directions (parallel to axis (627)), and distal end (616) of buttress body (512) is substantially prevented from moving in the proximal and distal directions (parallel to axis (627)). Thus, the releasable mechanical coupling between buttress bodies (612) and connector portions (680) substantially resists proximal and distal movement of buttress body (612).

The retention force provided by the engagement between connector portions (680) and slots (620, 622) is sufficient to maintain the removable coupling between buttress assembly (610) and cartridge (670) absent a sufficient decoupling force. However, buttress assembly (610) is configured to decouple from cartridge (670) in response to a sufficient decoupling force input. In the present example, the upward force associated with being captured by staples (90) provides sufficient decoupling force to release buttress assembly (610) from connector portions (680) of cartridge (670), as discussed in further detail below.

As shown, one buttress body (612) is disposed on deck (673) on one side of channel (672) and another portion of buttress body (612) is disposed on deck (673) on the other side of channel (672), such that no portion of buttress body (612) spans across channel (672). Therefore, the effort required to actuate end effector (40) and sever and staple tissue is reduced. As end effector (40) is actuated and staples (90) capture buttress body (612), the portion of buttress body (612) near the proximal slot (620) and connector portions (680) is driven upwardly and slips out of engagement with connector portion (680). As knife member (80) and sled (78) travel further longitudinally, proximal portion of buttress body (612) is captured by staples (90) and the portion of buttress body (612) near the distal slot (622) is driven upwardly and slips out of engagement with connector portion (680). Due to the positions of the buttress bodies (612) and connector portions (680) away from channel (672) knife member (680) does not sever any of buttress bodies (612) or connector portions (680).

Figure 18:
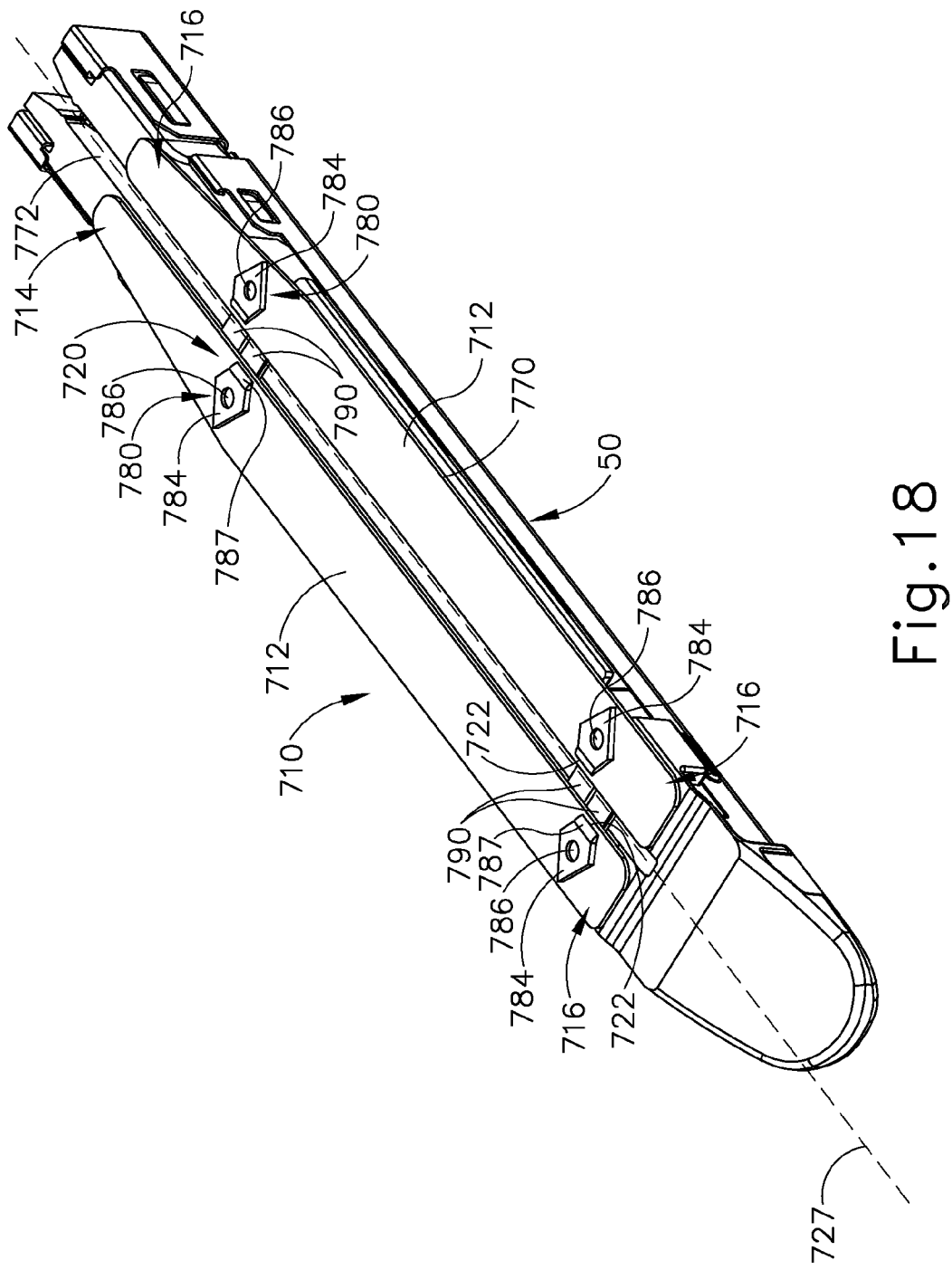
FIG. 18 depicts a perspective view of another exemplary alternative staple cartridge incorporated into the lower jaw of end effector of instrument of FIG. 1, including another exemplary alternative buttress assembly and connector portion.
Figure 21:
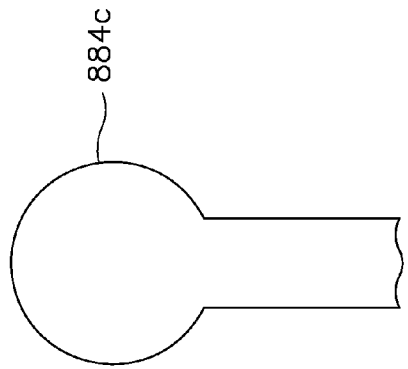
FIG. 21 depicts a top plan view of another exemplary alternative head portion suitable for incorporation into any of the connector portions shown in FIGS. 10 and 12-18.
Figure 24:
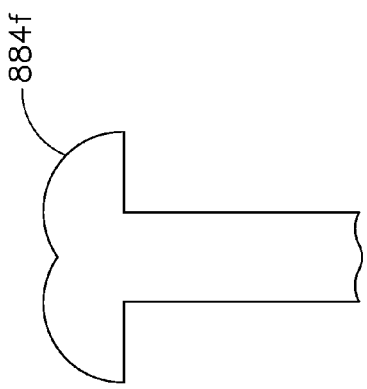
FIG. 24 depicts a top plan view of another exemplary alternative head portion suitable for incorporation into any of the connector portions shown in FIGS. 10 and 12-18.
Figure 20:
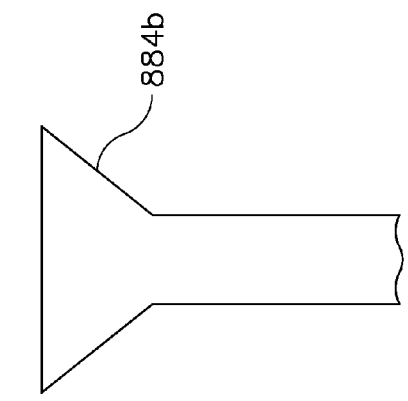
FIG. 20 depicts a top plan view of an exemplary alternative head portion suitable for incorporation into any of the connector portions shown in FIGS. 10 and 12-18.
Figure 23:
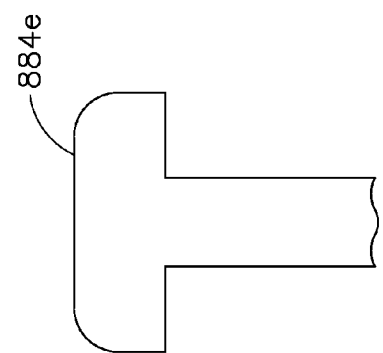
FIG. 23 depicts a top plan view of another exemplary alternative head portion suitable for incorporation into any of the connector portions shown in FIGS. 10 and 12-18.
Figure 19:
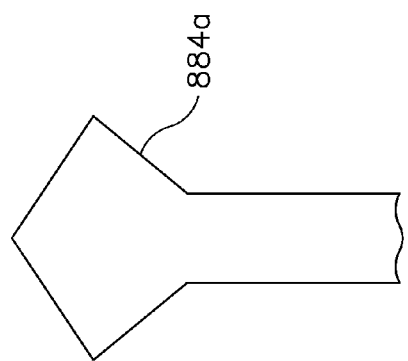
FIG. 19 depicts a top plan view of an exemplary alternative head portion suitable for incorporation into any of the connector portions shown in FIGS. 10 and 12-18.
Figure 22:
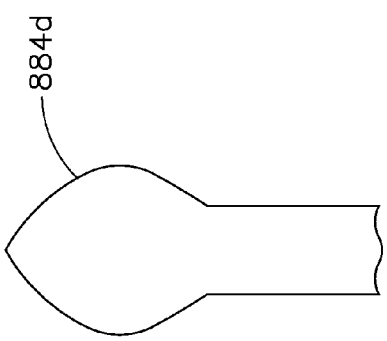
FIG. 22 depicts a top plan view of another exemplary alternative head portion suitable for incorporation into any of the connector portions shown in FIGS. 10 and 12-18.
Figure 31:
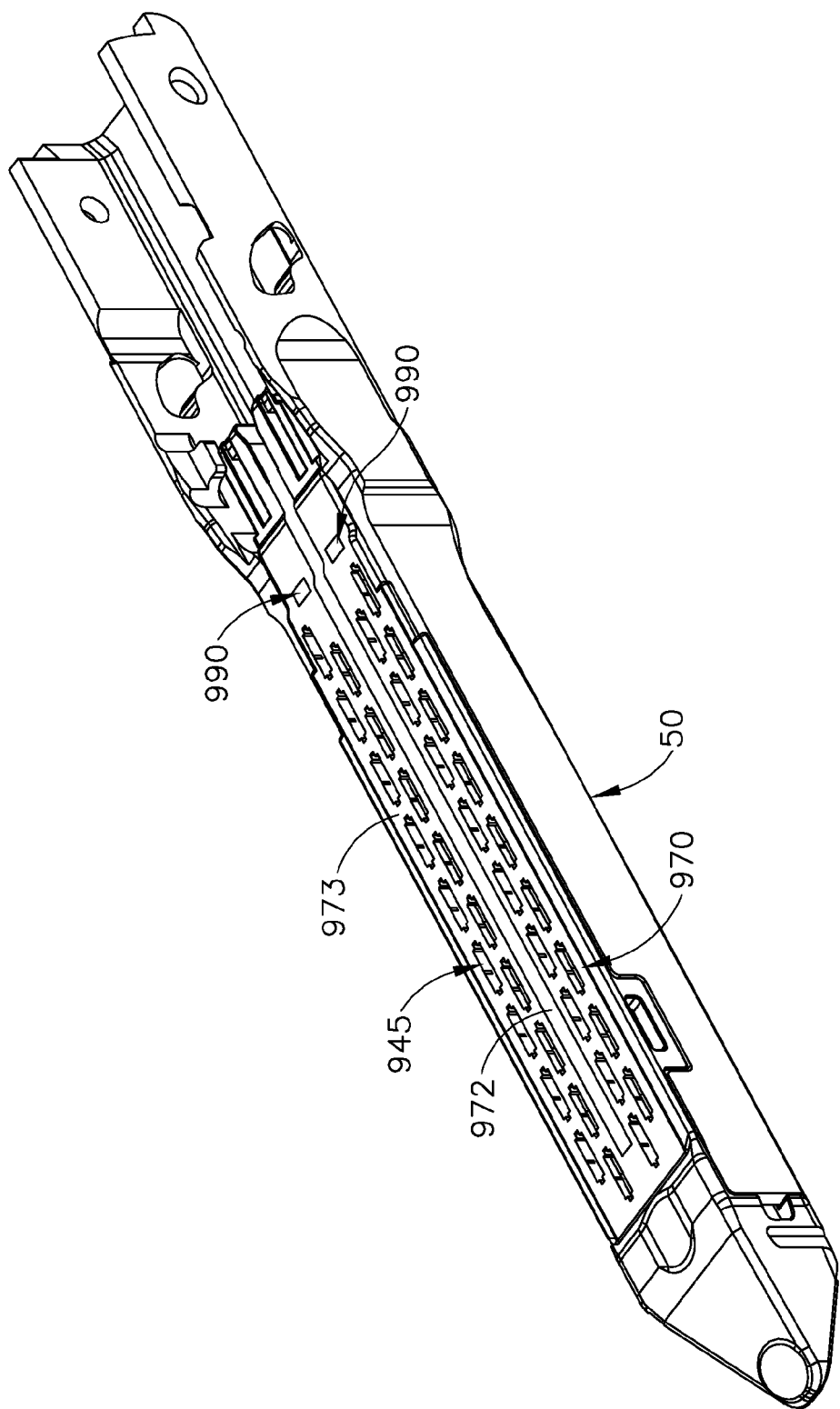
FIG. 31 depicts a perspective view of another exemplary alternative staple cartridge incorporated into the lower jaw of end effector of instrument of FIG. 1.
Figure 34:
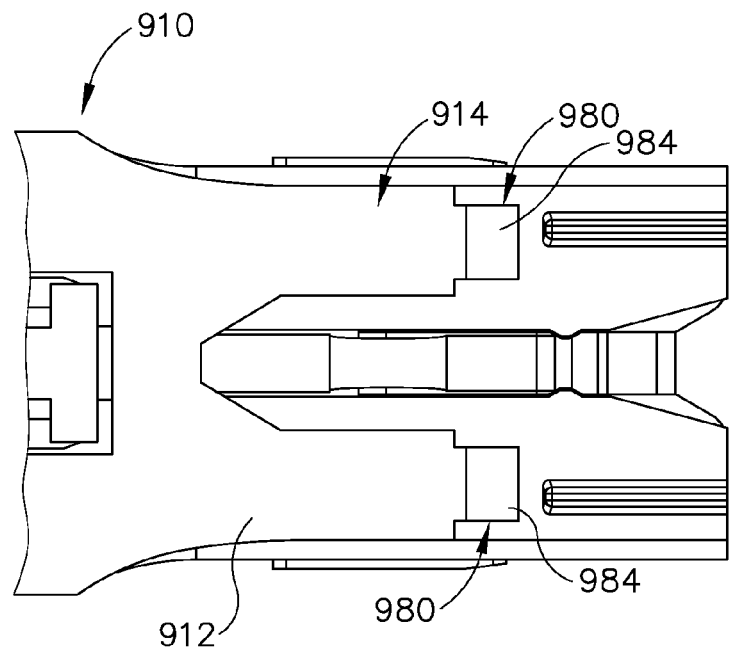
FIG. 34 depicts a detailed top plan view showing an attachment feature of the buttress assembly of FIG. 32 having been engaged with the staple cartridge of FIG. 31.
Figure 35:
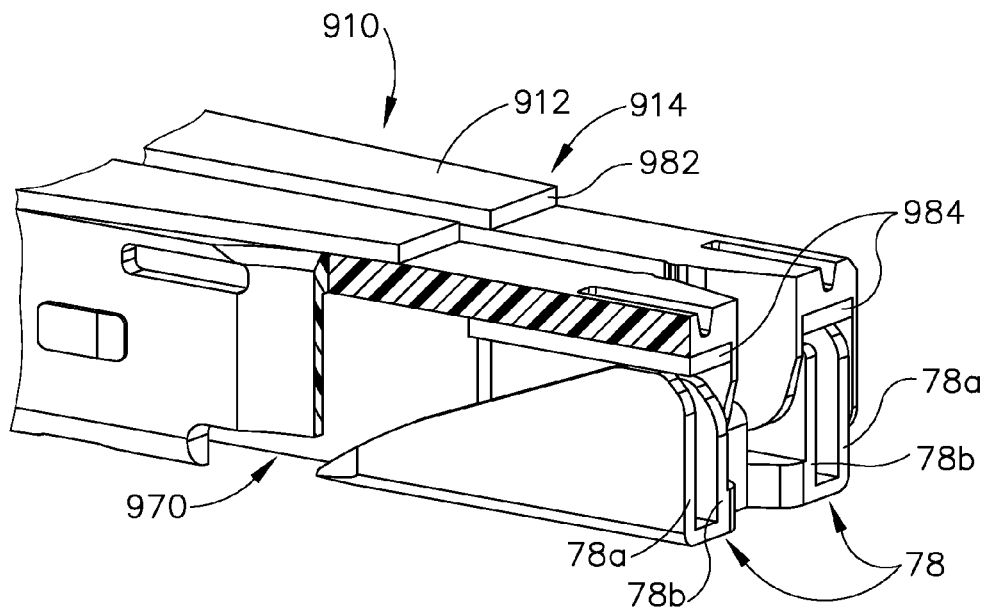
FIG. 35 depicts a cross-sectional perspective view of an attachment feature of the buttress assembly of FIG. 32 having been engaged with the staple cartridge of FIG. 31.
Figure 36:
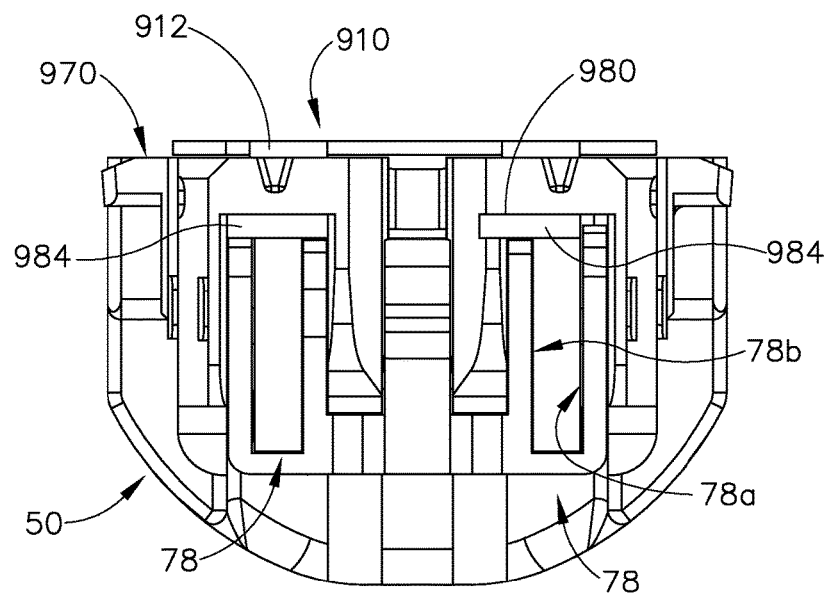
FIG. 36 depicts a cross-sectional end view showing the attachment feature of the buttress assembly of FIG. 32 having been engaged with the staple cartridge of FIG. 31.

FIG. 18 shows another exemplary alternative buttress assembly (710) in combination with an exemplary alternative staple cartridge (770) including exemplary alternative connector portions. Buttress assembly (710) is substantially identical to buttress assembly (510, 610) discussed above, except for that buttress bodies (712) include slots (720, 722) that extend parallel to the longitudinal axis (727) of buttress assembly (710).

Staple cartridge (770) includes exemplary alternative connector members (780), each of which extends partially along channel (772) in a manner so as not to impede traversal of knife member (80) therethrough. As shown, each connector member (580) includes a first end (782) with a head (784) including an aperture (786), a notch (787), and a second end portion (790) extending transversely relative to axis (727). As shown in the present example, each second end portion (790) extends across channel (772). Thus, each connector member (780) spans channel (772) in an opposite direction relative to an adjacent connector member (780). Thus, heads (784) of adjacent connector portions (780) extend in offset, opposite, and parallel directions. Alternative examples of head (784) may include any other suitable shape, including the shapes of any one of alternative heads (884a-8841) shown in FIGS. 19-30. Other suitable configurations of connector members (780) will be apparent to persons skilled in the art in view of the teachings herein.

To couple a buttress body (712) to a set of connector portions (780), proximal end (714) of buttress body (712) is directed toward connector portion (780) such that head (784) enters slot (720) (in a direction perpendicular to axis (727)) on second side of buttress body (712), until a trailing edge of connector portion (780) extends out of slot (720) and slot (720) engages with notch (787). Similarly, an operator may direct the distal end (716) of buttress (712) toward the other connector portion (780) such that head (784) enters slot (722) (in a direction perpendicular to axis (727)) on first side of buttress body (712), until a trailing edge of connector portion (780) extends out of slot (722), and slot (722) engages with notch (787). Due to the configuration of slots (720, 722) and head (784), proximal end (714) of buttress body (712) is substantially prevented from moving in the proximal and distal directions (parallel to axis (727)), and distal end (716) of buttress body (712) is substantially prevented from moving in the proximal and distal directions (parallel to axis (727)). Thus, the releasable mechanical coupling between buttress bodies (712) and connector portions (580) substantially prevents proximal and distal movement of buttress body (712).

The retention force provided by the engagement between connector portions (780) and slots (720, 722) is sufficient to maintain the removable coupling between buttress assembly (710) and cartridge (770) absent a sufficient decoupling force. However, buttress assembly (710) is configured to decouple from cartridge (770) in response to a sufficient decoupling force input. In the present example, the upward force associated with being captured by staples (90) provides sufficient decoupling force to release buttress assembly (710) from connector portions (780) of cartridge (770), as discussed in further detail below.

As shown, one buttress body (712) is disposed on deck (773) on one side of channel (772) and another portion of buttress body (712) is disposed on deck (773) on the other side of channel (772), such that no portion of buttress body (712) spans across channel (772). However, second end portions (790) span channel (772). Nonetheless, the effort required to actuate end effector (40) and sever and staple tissue is reduced. As end effector (40) is actuated and staples (90) capture buttress body (712), the portion of buttress body (712) near the proximal slot (720) and connector portions (780) is driven upward and slips out of engagement with connector portion (780). As knife member (80) and sled (78) travel further longitudinally, proximal portion of buttress body (712) is captured by staples (90) and the portion of buttress body (712) near the distal slot (722) is driven upward and slips out of engagement with connector portion (780). Due to the positions buttress bodies (712) being away from channel (772), knife member (80) does not sever any of buttress bodies (712).

C. Buttress Assemblies with Attachment Members for Engaging with Staple Cartridge Deck FIGS. 31 and 34-36 show an exemplary alternative staple cartridge (970) incorporated into lower jaw (50) of end effector (40). Staple cartridge (970) is configured to operate substantially similar to staple cartridge (70), except for the differences below. Particularly, staple cartridge (970) includes a pair of apertures (990) positioned proximal to staple openings (945). Apertures (990) are configured to receive attachment features (980) of a buttress assembly (910) in order to removably and mechanically couple buttress assembly (910), as discussed in further detail below.

As shown best in FIGS. 32-33, buttress assembly (910) includes a buttress body (912) including a proximal end (914), a distal end (916), and a plurality of apertures (918) extending along an axis (927) thereof. Apertures (916) may reduce the amount of force required for knife member (80) to cut through and traverse past severed tissue and buttress body (912). While four apertures (918) are shown in the present example, in alternative examples there may be less than (e.g., three, two, one, or zero) or more than four apertures (918). Other suitable configurations of apertures (918) will be apparent to persons skilled in the art in view of the teachings herein.

As shown, at the proximal end (914), attachment members (980) extend proximally from buttress body (912). Particularly, attachment members (980) include a first portion (982) extending in a perpendicular direction away from buttress body (912), and a second portion (984) extending proximally away from first portion (982) and parallel to buttress body (912). In the present example, any or all of attachment members (980) comprise the same material or materials as buttress body (912). In other examples, any or all of attachment members (980) may comprise a plurality of laminate, bioabsorbable layers, which may or may not include a layer that comprises part of buttress body (912). Other suitable configurations and materials that attachment members (980) may comprise will be apparent to persons skilled in the art in view of the teachings herein.

In order to removably couple buttress assembly (910) to cartridge (970), an operator may direct the second portions (984) of attachment members (980) into apertures (990) proximally and downwardly through apertures (990) until the first portion (982) enters apertures (990) and the bottom face (913) of buttress body (912) is flush with cartridge deck (973). In the present example, apertures (990) are positioned on cartridge (970), and attachment members are sized and configured such that when attachment members (980) are directed into apertures (990), attachment members (980) are releasably held between an underneath portion (973a) of deck (973) and rails (78a, 78b) of sled (78). In an alternative example, rather than being held between the top of rails (78a, 78b) and underneath portion (973a) of deck (973), attachment members may be releasably held (e.g., via an interference fit), between the rails (78a, 78b) of sled.

The retention force provided by the engagement between attachment members (980), cartridge deck (973), and sled rails (78a, 78b) is sufficient to maintain the removable coupling between buttress assembly (910) and cartridge (770) absent a sufficient decoupling force. However, buttress assembly (910) is configured to decouple from cartridge (970) in response to a sufficient decoupling force input. In the present example, longitudinal movement of sled (78) disengages sled rails (78a, 78b) from second portion, reducing the retention force between sled rails (78a, 78b), cartridge deck (973), and attachment members. Moreover, the upward force associated with being captured by staples (90) provides sufficient decoupling force to release buttress assembly (910) from connector portions (980) of cartridge (970), as discussed in further detail below.

It should be understood that upon actuation of end effector (40), a series of staples (90) will similarly capture and retain buttress assembly (910) against layers of tissue ($T_1$, $T_2$), thereby securing buttress assembly (910) to tissue ($T_1$, $T_2$) in a similar manner as shown in FIG. 6. In some examples, buttress assembly (910) may be utilized in conjunction with buttress assembly (100) on anvil (60) such that a series of staples (90) will similarly capture and retain buttress assemblies (100, 910) against layers of tissue ($T_1$, $T_2$), thereby securing buttress assemblies (100, 910) to tissue ($T_1$, $T_2$) in a similar manner as shown in FIG. 6.

Figure 37:
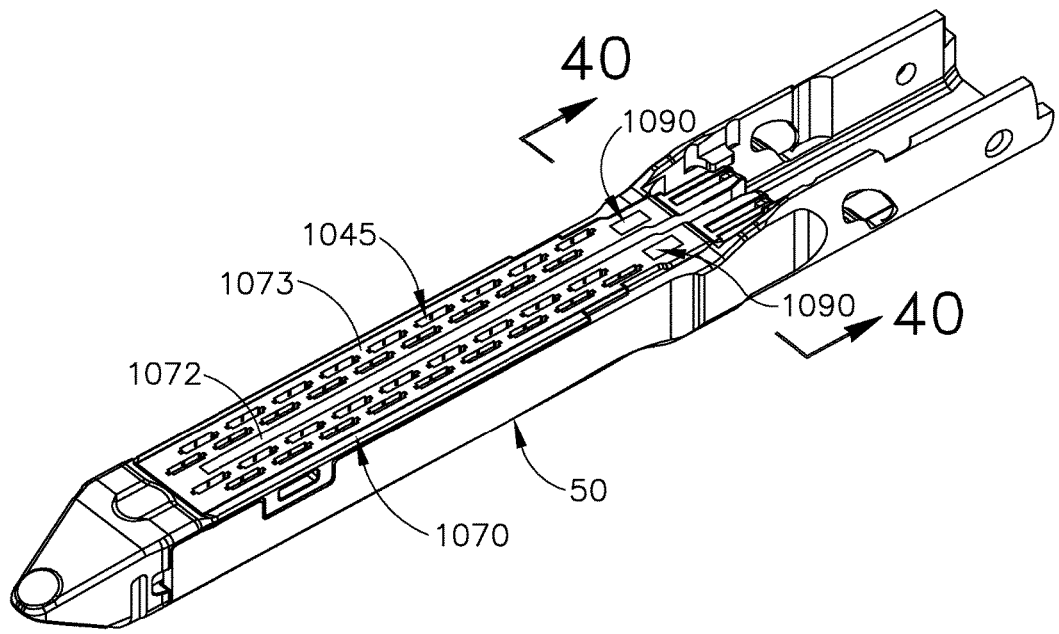
FIG. 37 depicts a perspective view of another exemplary alternative staple cartridge incorporated into the lower jaw of end effector of instrument of FIG. 1.
Figure 40:
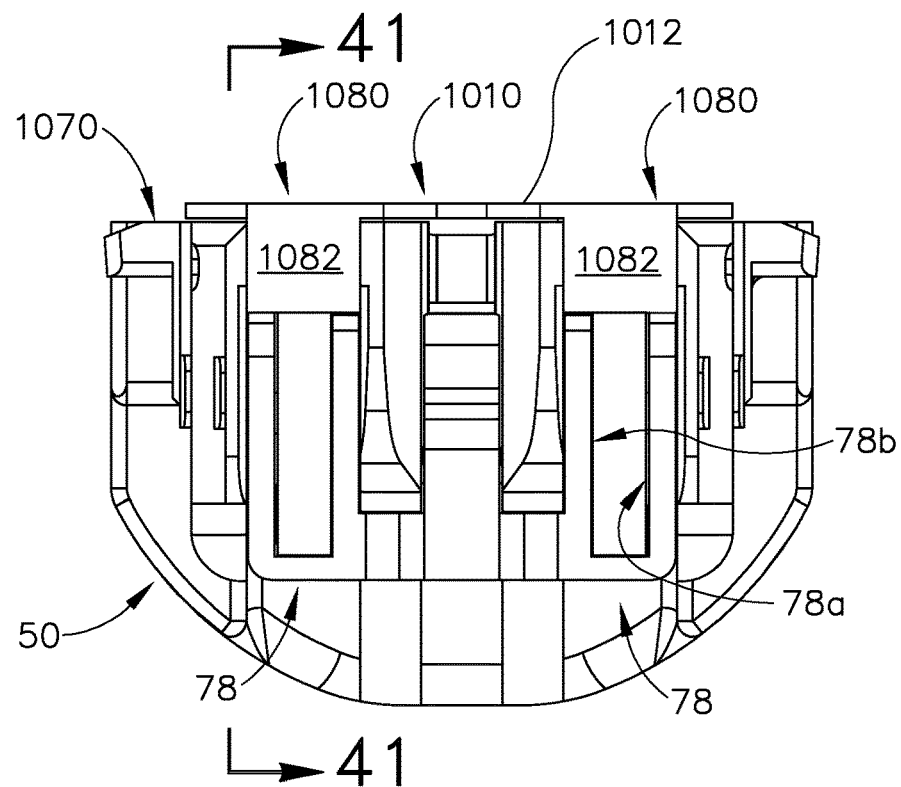
FIG. 40 depicts a cross-sectional view, taken along line 40-40 of FIG. 37, showing an attachment feature of the buttress assembly of FIG. 38 having been engaged with the staple cartridge of FIG. 37.
Figure 41:
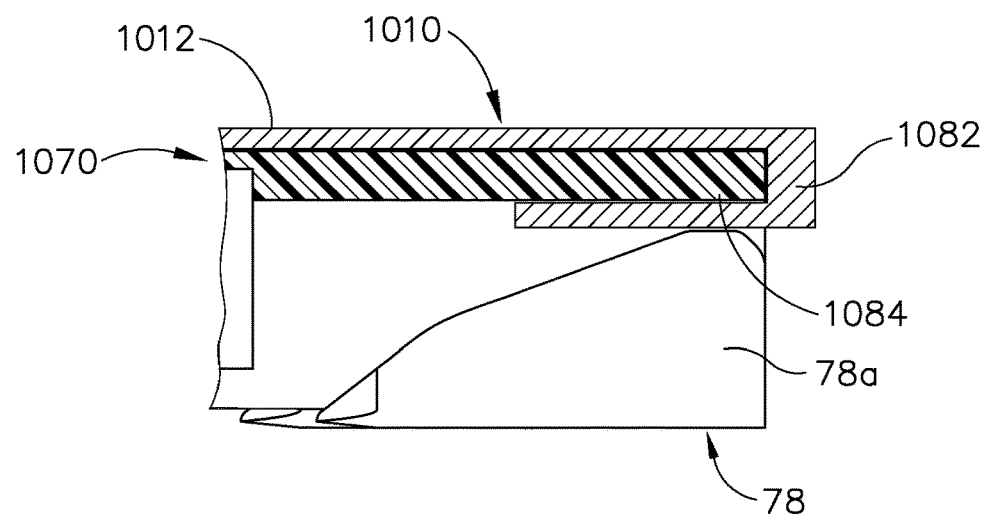
FIG. 41 depicts a cross-sectional view, taken along line 41-41 of FIG. 40, showing the attachment feature of the buttress assembly of FIG. 38 having been engaged with the staple cartridge of FIG. 37.

FIGS. 37 and 40-41 show an exemplary alternative staple cartridge (1070) incorporated into lower jaw (50) of end effector (40). Staple cartridge (1070) is configured to operate substantially similar to staple cartridge (70), except for the differences below. Particularly, staple cartridge (1070) includes a pair of apertures (1090) positioned proximal to staple openings (1045). Apertures (1090) are configured to receive attachment features (1080) of a buttress assembly (1010) in order to removably and mechanically couple buttress assembly (1010), as discussed in further detail below.

Figure 38:
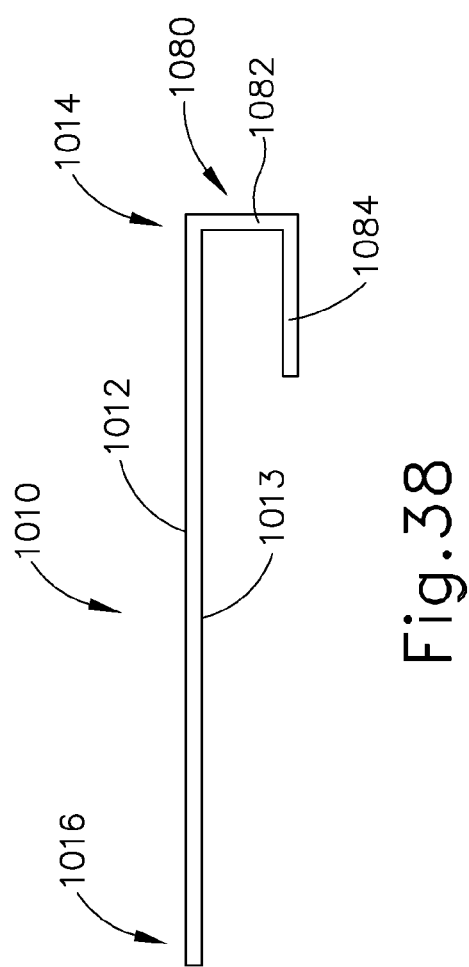
FIG. 38 depicts a side elevational view of another exemplary alternative buttress assembly.
Figure 39:
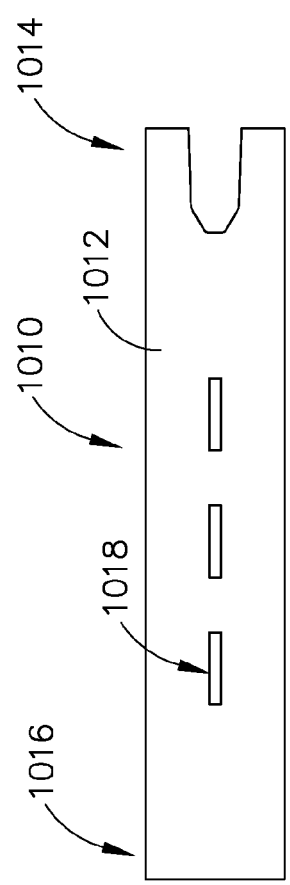
FIG. 39 depicts a top plan view of the buttress assembly of FIG. 38.

As shown best in FIGS. 38-39, buttress assembly (1010) includes a buttress body (1012) having a proximal end (1014), a distal end (1016), and a plurality of apertures (1018) extending along an axis (1027) thereof. Apertures (1016) may reduce the amount of force required for knife member (80) to cut through and traverse past severed tissue and buttress body (1012). While four apertures (1018) are shown in the present example, in alternative examples there may be less than (e.g., three, two, one, or zero) or more than four apertures (1018). Other suitable configurations of apertures (1018) will be apparent to persons skilled in the art in view of the teachings herein.

As shown, attachment members (1080) include a first portion (1082) extending in a perpendicular direction away from proximal end (1014) of buttress body (1012), and a second portion (1084) extending perpendicularly away from first portion (1082) toward distal end (1016) and parallel to buttress body (1012). In the present example, any or all of attachment members (1080) comprise the same material or materials as buttress body (1012). In other examples, any or all of attachment members (1080) may comprise a plurality of laminate, bioabsorbable layers, which may or may not include a layer that comprises part of buttress body (1012). Other suitable configurations and materials that attachment members (1080) may comprise will be apparent to persons skilled in the art in view of the teachings herein.

In order to removably couple buttress assembly (1010) to cartridge (1070), an operator may direct the second portions (1084) of attachment members (1080) into apertures (1090) distally and downwardly through apertures (1090) until the first portion (1082) may enter apertures (1090) and the bottom face (1013) of buttress body (1012) is flush with cartridge deck (1073). In the present example, apertures (1090) are positioned on cartridge (1070), and attachment members are sized and configured such that when attachment members (1080) are directed into apertures (1090), attachment members (1080) are releasably held between an underneath portion (1073a) of deck (1073) and rails (78a, 78b) of sled (78).

The retention force provided by the engagement between attachment members (1080), cartridge deck (1073), and sled rails (78a, 78b) is sufficient to maintain the removable coupling between buttress assembly (1010) and cartridge (1070) absent a sufficient decoupling force. However, buttress assembly (1010) is configured to decouple from cartridge (1070) in response to a sufficient decoupling force input. In the present example, longitudinal movement of sled (78) disengages sled rails (78a, 78b) from second portion, reducing the retention force between sled rails (78a, 78b), cartridge deck (1073), and attachment members. Moreover, the upward force associated with being captured by staples (90) provides additional and sufficient decoupling force to release buttress assembly (1010) from connector portions (1080) of cartridge (1070), as discussed in further detail below.

It should be understood that upon actuation of end effector (40), a series of staples (90) will similarly capture and retain buttress assembly (1010) against layers of tissue ($T_1$, $T_2$), thereby securing buttress assembly (1010) to tissue ($T_1$, $T_2$) in a similar manner as shown in FIG. 6. In some examples, buttress assembly (1010) may be utilized in conjunction with buttress assembly (100) on anvil (60) such that a series of staples (90) will similarly capture and retain buttress assemblies (100, 1010) against layers of tissue ($T_1$, $T_2$), thereby securing buttress assemblies (100, 1010) to tissue ($T_1$, $T_2$) in a similar manner as shown in FIG. 6.

Figure 42:
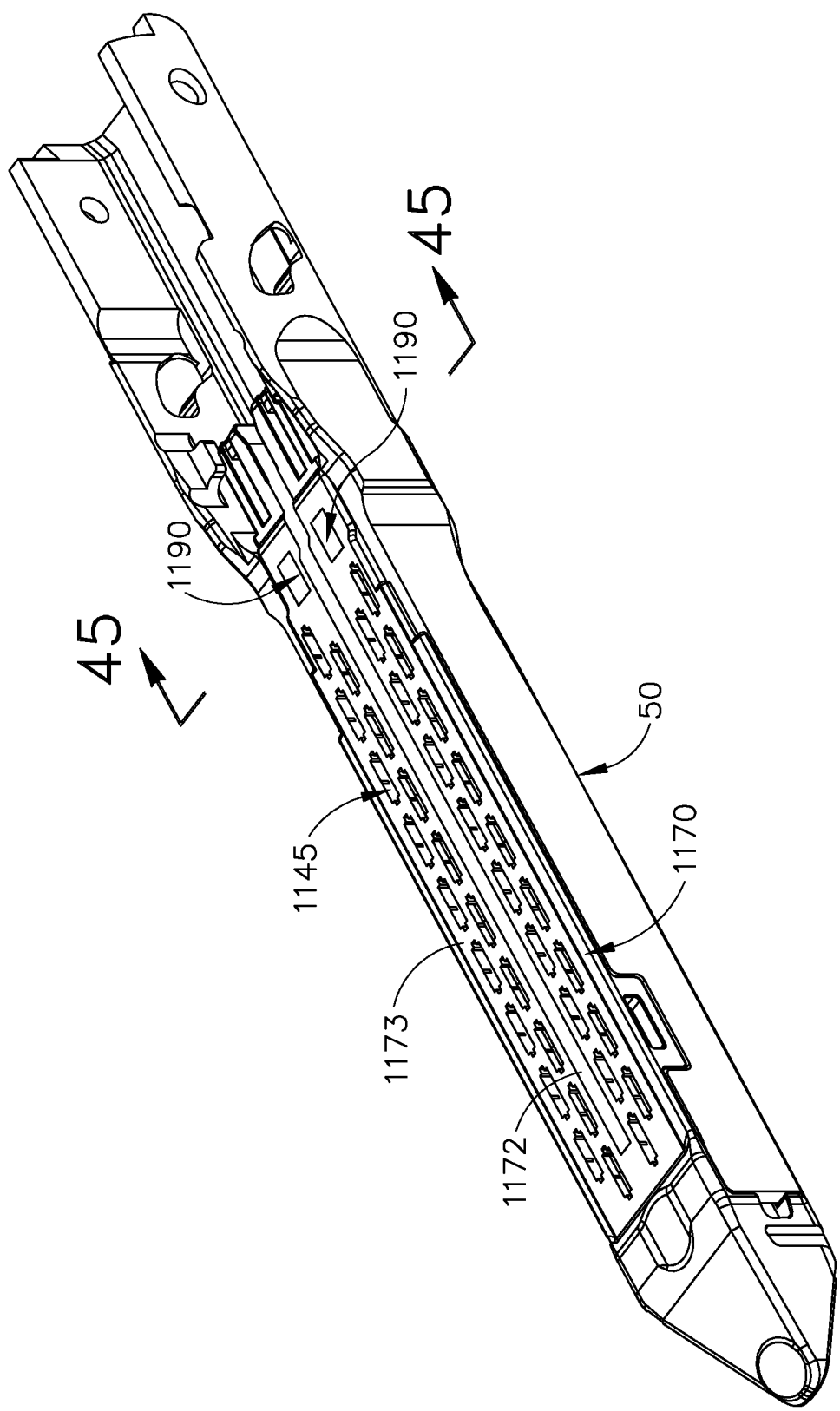
FIG. 42 depicts a perspective view of another exemplary alternative staple cartridge incorporated into the lower jaw of end effector of instrument of FIG. 1.
Figure 45:
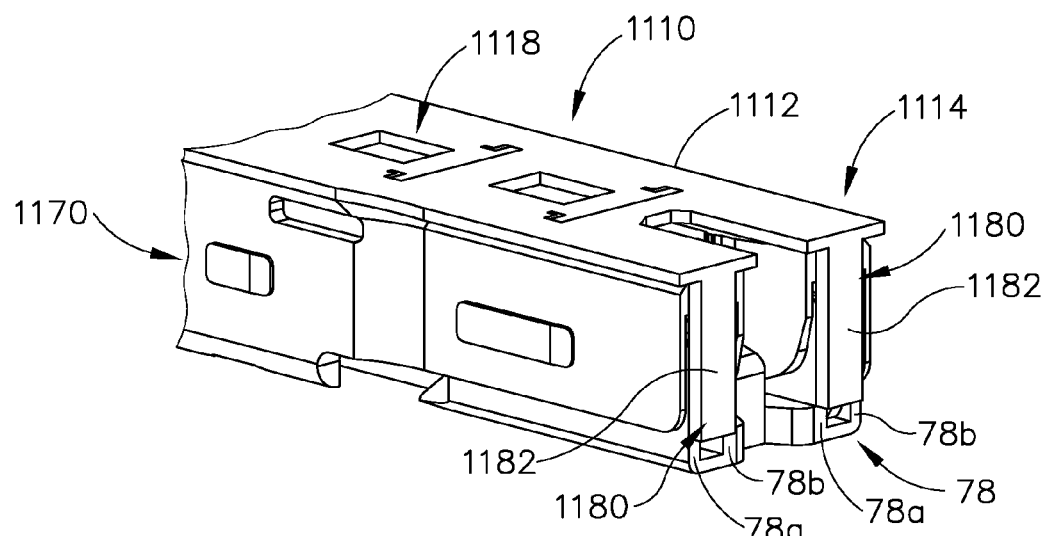
FIG. 45 depicts a cross-sectional perspective view, taken along line 45-45 of FIG. 42, showing an attachment feature of the buttress assembly of FIG. 43 having been engaged with the staple cartridge of FIG. 42.
Figure 46:
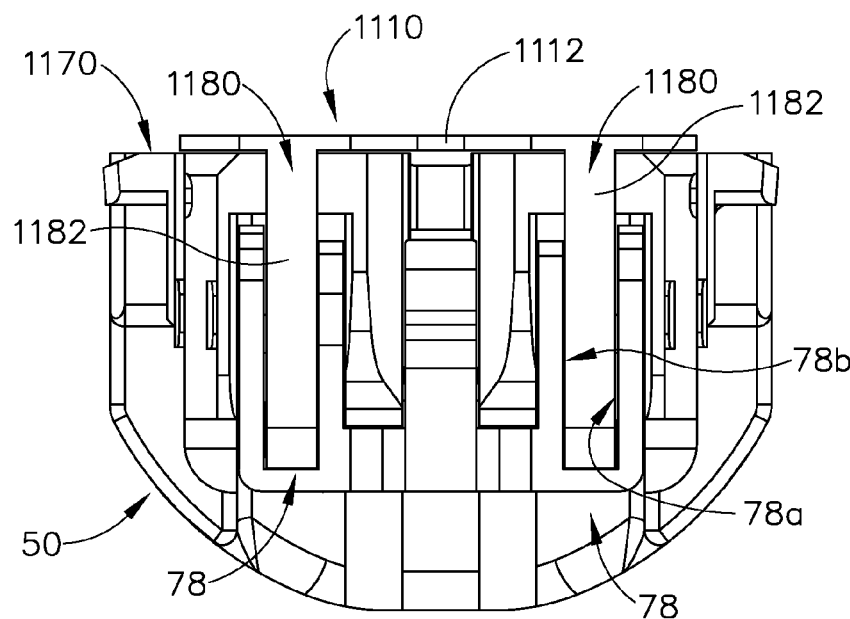
FIG. 46 depicts a cross-sectional end view showing the attachment feature of the buttress assembly of FIG. 43 having been engaged with the staple cartridge of FIG. 42.

FIGS. 42 and 45-46 show an exemplary alternative staple cartridge (1170) incorporated into lower jaw (50) of end effector (40). Staple cartridge (1170) is configured to operate substantially similar to staple cartridge (70), except for the differences below. Particularly, staple cartridge (1170) includes a pair of apertures (1190) positioned proximal to staple openings (1145). Apertures are configured to receive attachment features (1180) of a buttress assembly (1110) in order to removably and mechanically couple buttress assembly (1110), as discussed in further detail below.

Figure 43:
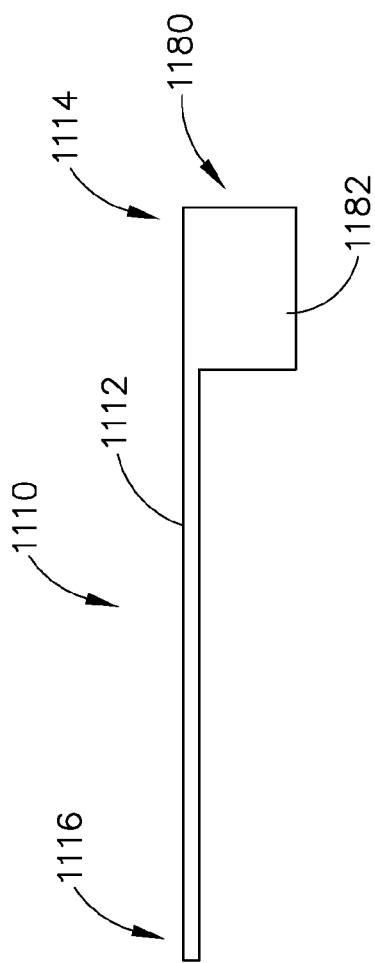
FIG. 43 depicts a side elevational view of another exemplary alternative buttress assembly.
Figure 44:
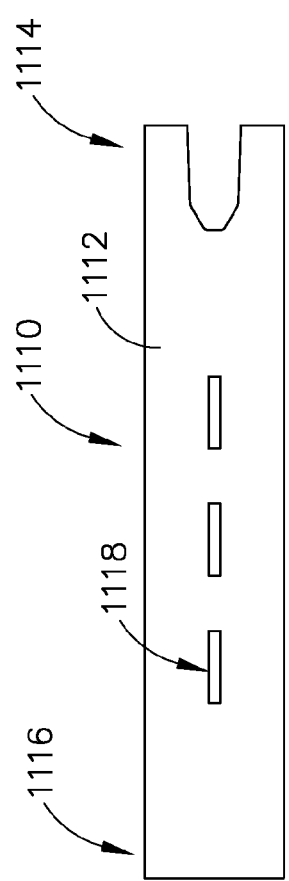
FIG. 44 depicts a top plan view of the buttress assembly of FIG. 43.

As shown best in FIGS. 43-44, buttress assembly (1110) includes a buttress body (1112) having a proximal end (1114), a distal end (1116), and a plurality of apertures (1118) extending along an axis (1127) thereof. Apertures (1116) may reduce the amount of force required for knife member (80) to cut through and traverse past severed tissue and buttress body (1112). While four apertures (1116) are shown in the present example, in alternative examples there may be less than (e.g., three, two, one, or zero) or more than four apertures (1116). Other suitable configurations of apertures (1116) will be apparent to persons skilled in the art in view of the teachings herein.

As shown, attachment members (1180) include a first portion (1182) extending in a perpendicular direction away from proximal end (1014) of buttress body (1112). In the present example, any or all of attachment members (1180) comprise the same material or materials as buttress body (1112). In other examples, any or all of attachment members (1180) may comprise a plurality of laminate, bioabsorbable layers, which may or may not include a layer that comprises part of buttress body (1112). Other suitable configurations and materials that attachment members (1180) may comprise will be apparent to persons skilled in the art in view of the teachings herein.

In order to removably couple buttress assembly (1110) to cartridge (1170), an operator may direct the first portions (1182) of attachment members (1180) into apertures (1190) downwardly through apertures (1190) (in a direction perpendicular to deck (1173)) until the bottom face (1113) of buttress body (1112) is flush with cartridge deck (1173). In the present example, apertures (1190) are positioned on cartridge (1170), and attachment members (1180) are sized and configured such that when attachment members (1180) are directed into apertures (1190), each attachment member (1180) is releasably held between each rail (78a, 78b) of sled (78). In the example shown, each attachment member (1180) is interference fit in between each set of sled rails (78a, 78b), but may alternatively be releasably held in other suitable manners.

The retention force provided by the engagement between attachment members (1180) and sled rails (78a, 78b) is sufficient to maintain the removable coupling between buttress assembly (1110) and cartridge (1170) absent a sufficient decoupling force. However, buttress assembly (1110) is configured to decouple from cartridge (1170) in response to a sufficient decoupling force input. In the present example, longitudinal movement of sled (78) disengages sled rails (78a, 78b) from attachment members (1180), reducing or eliminating the retention force between sled rails (78a, 78b) and attachment members (1180). Moreover, the upward force associated with being captured by staples (90) provides additional and sufficient decoupling force to release buttress assembly (1110) from connector portions (1180) of cartridge (1170), as discussed in further detail below.

It should be understood that upon actuation of end effector (40), a series of staples (90) will similarly capture and retain buttress assembly (1110) against layers of tissue ($T_1$, $T_2$), thereby securing buttress assembly (1110) to tissue ($T_1$, $T_2$) in a similar manner as shown in FIG. 6. In some examples, buttress assembly (1110) may be utilized in conjunction with buttress assembly (100) on anvil (60) such that a series of staples (90) will similarly capture and retain buttress assemblies (100, 1110) against layers of tissue ($T_1$, $T_2$), thereby securing buttress assemblies (100, 1110) to tissue ($T_1$, $T_2$) in a similar manner as shown in FIG. 6.

Figure 47:
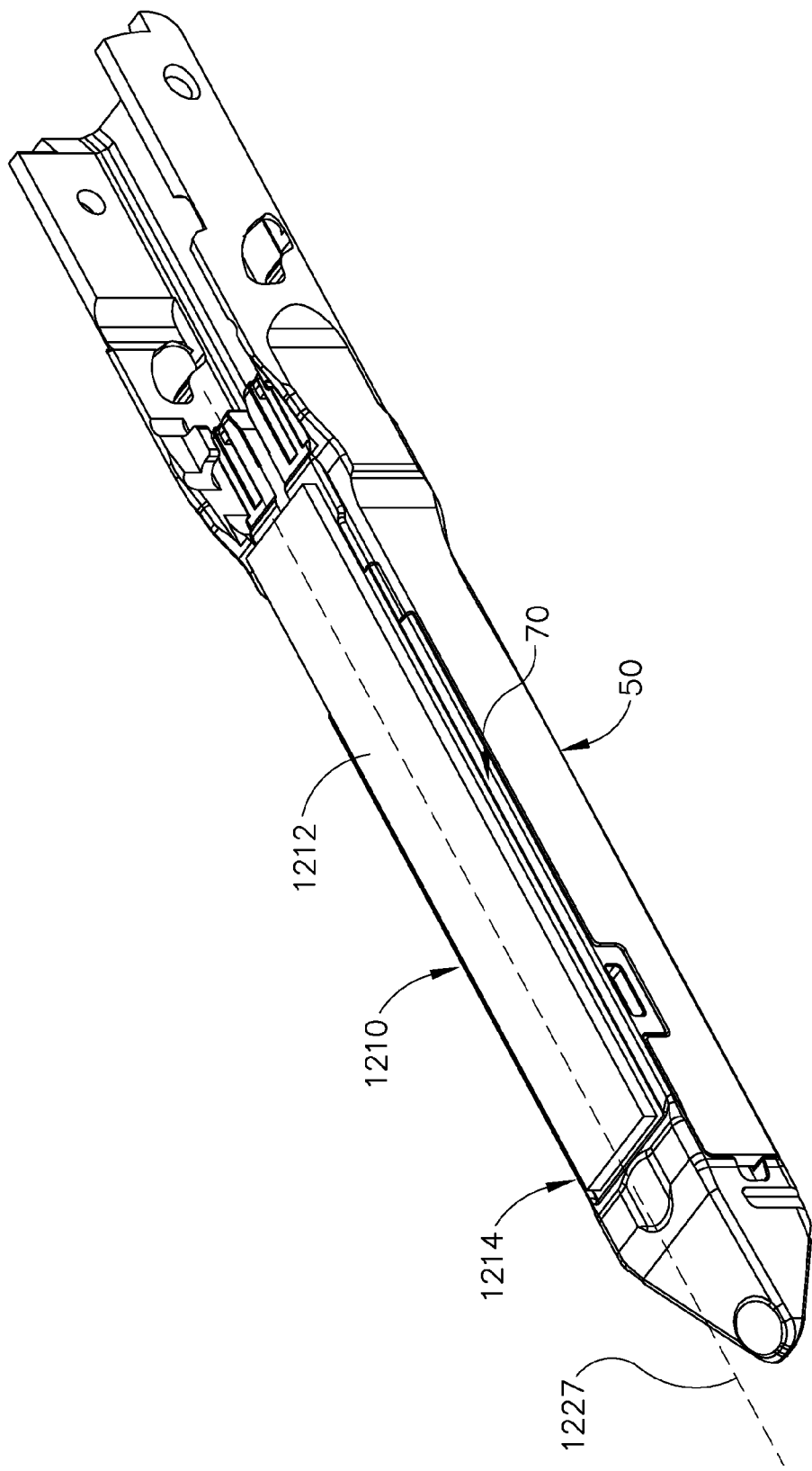
FIG. 47 depicts a perspective view of another exemplary alternative staple cartridge incorporated into the lower jaw of end effector of instrument of FIG. 1, including another exemplary alternative buttress assembly.

FIG. 47 shows another exemplary alternative buttress assembly (1210) releasably coupled to staple cartridge (70) via an attachment member (1280). Unlike the previous examples, staple cartridge (70) does not need to be modified in order to accommodate an attachment member (1280) of buttress assembly (1210). In the example shown, buttress assembly (1210) comprises a buttress body (1212) extending including a proximal end (1214) and a distal end (1216). Buttress body (1212) extends along a longitudinal axis (1227).

Figure 48:
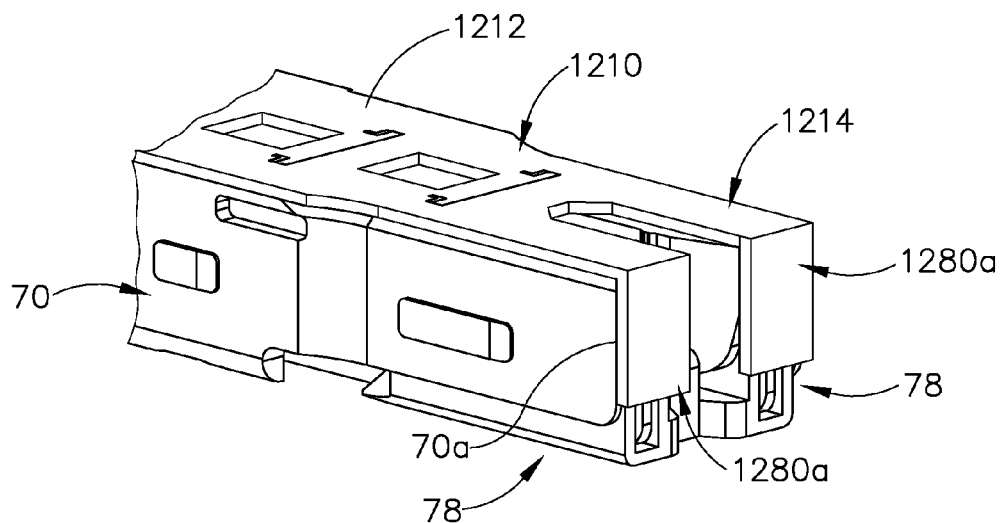
FIG. 48 depicts a perspective view of the proximal end of the staple cartridge of FIG. 47, showing an exemplary attachment feature of the buttress assembly of FIG. 47.
Figure 49:
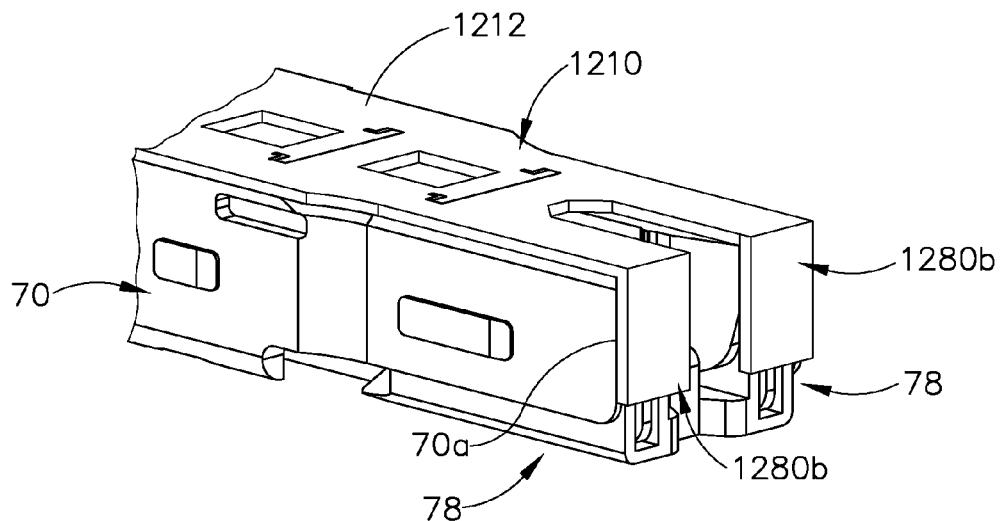
FIG. 49 depicts a perspective view of the proximal end of the staple cartridge of FIG. 47, showing an exemplary attachment feature that may be used with the buttress assembly of FIG. 47.

In the example shown in FIG. 48, attachment member (1280a) is in the form of a tab extending perpendicularly relative to the proximal end of buttress body (1212). In the present example, attachment member (1280a) comprises the same material or materials as buttress body (1212). Other suitable configurations and materials that attachment member may comprise will be apparent to persons skilled in the art in view of the teachings herein. For example, as shown in FIG. 49, attachment member (1280b) is substantially identical to attachment member (1280a), except for that attachment member (1280b) comprises a laminate material. Particularly, the laminate material comprises a plurality of laminate, bioabsorbable layers, which may or may not include a layer that comprises part of buttress body (1212). Other suitable configurations and materials that attachment member (1280b) may comprise will be apparent to persons skilled in the art in view of the teachings herein.

In order to removably couple buttress assembly (1210) to cartridge (70), an operator may direct the attachment member (1280a, 1280b) over the proximal end (70a) of cartridge (70) such that attachment member (1280a, 1280b) is positioned between proximal end of cartridge (70) and a distally facing portion of lower jaw, and until the bottom face (1213) of buttress body (1212) is flush with cartridge deck (73). Attachment member (1280a, 1280b) is sized and configured such that when attachment member (1180) is positioned between proximal end of cartridge (70) and lower jaw (50), attachment member (1180a, 1180b) is releasably held therebetween. In the example shown, attachment member (1180a, 1180b) is interference fit in between proximal end (70a) of cartridge (70) and lower jaw (50). It should be understood that buttress assembly (1210) may first be positioned on cartridge (70), and then the combination of buttress assembly (1210) and cartridge (70) may be loaded into lower jaw (50). Alternatively, cartridge (70) may be loaded into lower jaw (50) first; and then buttress assembly (1210) may be loaded onto cartridge (70).

The retention force provided by the engagement between attachment members (1280a, 1280b), proximal end (70a) of cartridge (70), and lower jaw (50) is sufficient to maintain the removable coupling between buttress assembly (1210) and cartridge (70) absent a sufficient decoupling force. However, buttress assembly (1210) is configured to decouple from cartridge (70) in response to a sufficient decoupling force input. In the present example, the upward force associated with being captured by staples (90) provides additional and sufficient decoupling force to release buttress assembly (1210) and connector portions (1280) from engagement with cartridge (70).

Figure 50:
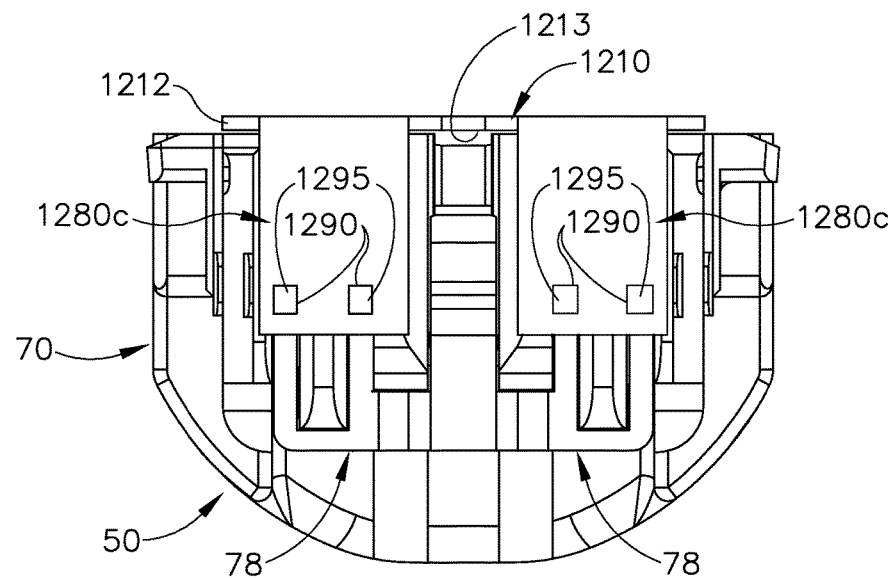
FIG. 50 depicts an end view of the proximal end of the staple cartridge of FIG. 47, showing an exemplary attachment feature that may be used with the buttress assembly of FIG. 47.
Figure 51:
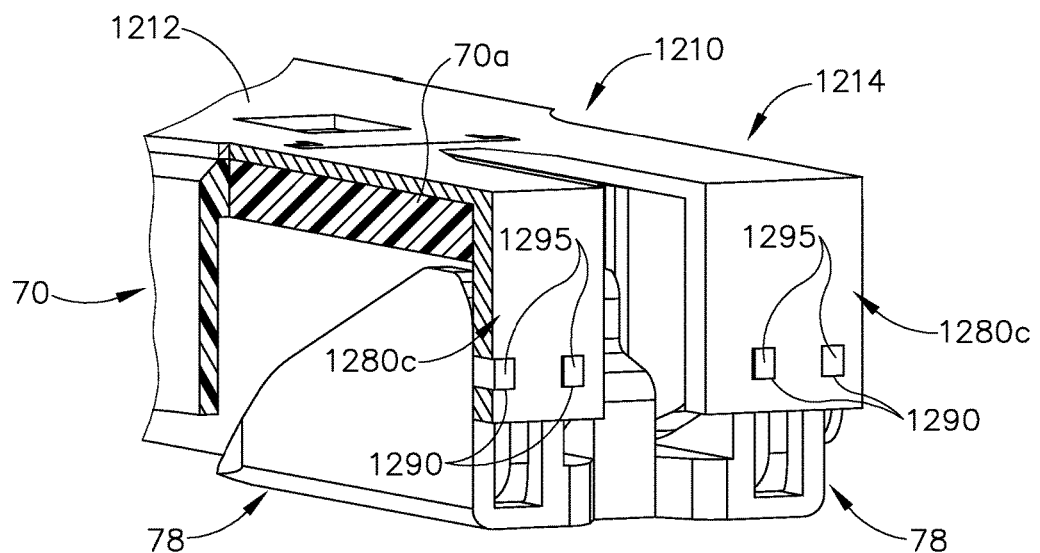
FIG. 51 depicts a cross-sectional perspective view of the proximal end of the staple cartridge of FIG. 47 with the attachment feature of FIG. 50.

FIGS. 50-51 show an exemplary variation of buttress assembly (1210) that includes alternative attachment members (1280c). As shown, each attachment member (1280c) includes a pair of apertures (1290) that are configured to receive similarly shaped extensions on sled (78). Particularly, as shown in FIGS. 50-51, each sled rail (78a, 78b) includes proximally projecting extensions (1295) that are sized and configured to be received in apertures (1290).

Thus, in order to removably couple buttress assembly (1210) including attachment members (1280c) to cartridge (70), an operator may direct attachment member (1280c) over the proximal end (70a) of cartridge (70) such that attachment member (1280c) is positioned between proximal end of cartridge (70) and a portion of lower jaw (50), and apertures (1290) engage the corresponding extensions (1295). Moreover, apertures (1290) and extensions (1295) are configured such that when they are engaged, the bottom face (1213) of buttress body (1212) is flush with cartridge deck (73).

The retention force provided by the engagement between apertures (1290) of attachment members (1280c), extensions (1295) of sled (78), and lower jaw (50) is sufficient to maintain the removable coupling between buttress assembly (1210) and cartridge (70) absent a sufficient decoupling force. However, buttress assembly (1210) is configured to decouple from cartridge (70) in response to a sufficient decoupling force input. In the present example, longitudinal movement of sled (78) disengages extensions (1295) from apertures (1290), reducing the retention force between sled rails (78a, 78b) and attachment members (1280c). In the present example, the upward force associated with being captured by staples (90) provides additional and sufficient decoupling force to release buttress assembly (1210) and connector portions (1280) from engagement with cartridge (70).

It should be understood that upon actuation of end effector (40), a series of staples (90) will similarly capture and retain buttress assembly (1210) against layers of tissue ($T_1$, $T_2$), thereby securing buttress assembly (1210) to tissue ($T_1$, $T_2$) in a similar manner as shown in FIG. 6. In some examples, buttress assembly (1210) may be utilized in conjunction with buttress assembly (100) on anvil (60) such that a series of staples (90) will similarly capture and retain buttress assemblies (100, 1210) against layers of tissue ($T_1$, $T_2$), thereby securing buttress assemblies (100, 1210) to tissue ($T_1$, $T_2$) in a similar manner as shown in FIG. 6.

Figure 52:
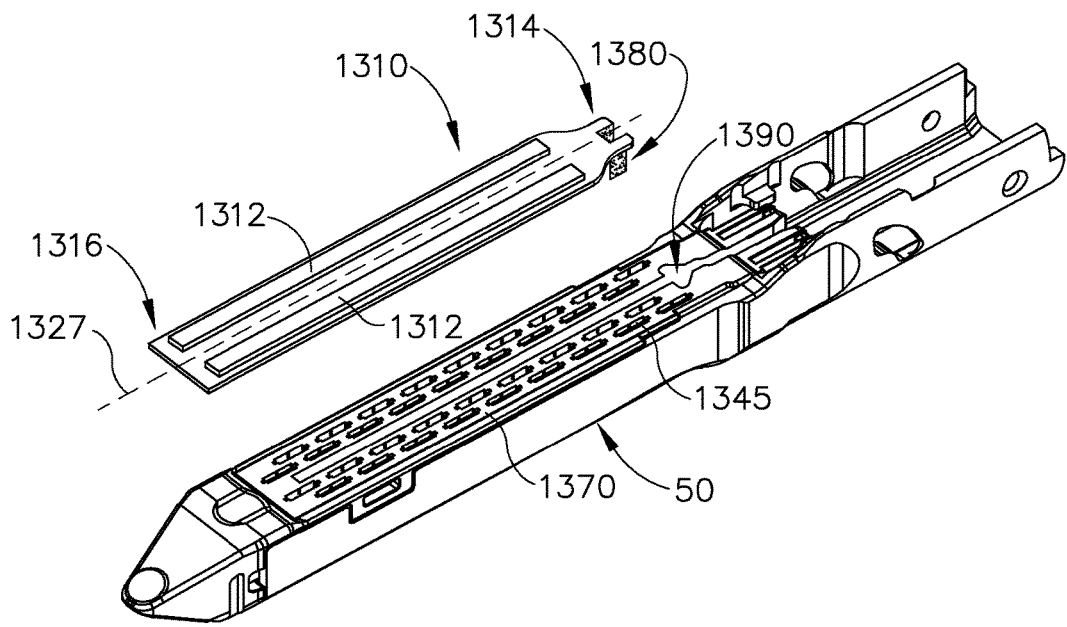
FIG. 52 depicts a perspective view of another exemplary alternative staple cartridge incorporated into the lower jaw of end effector of instrument of FIG. 1, including another exemplary alternative buttress assembly.
Figure 54A:
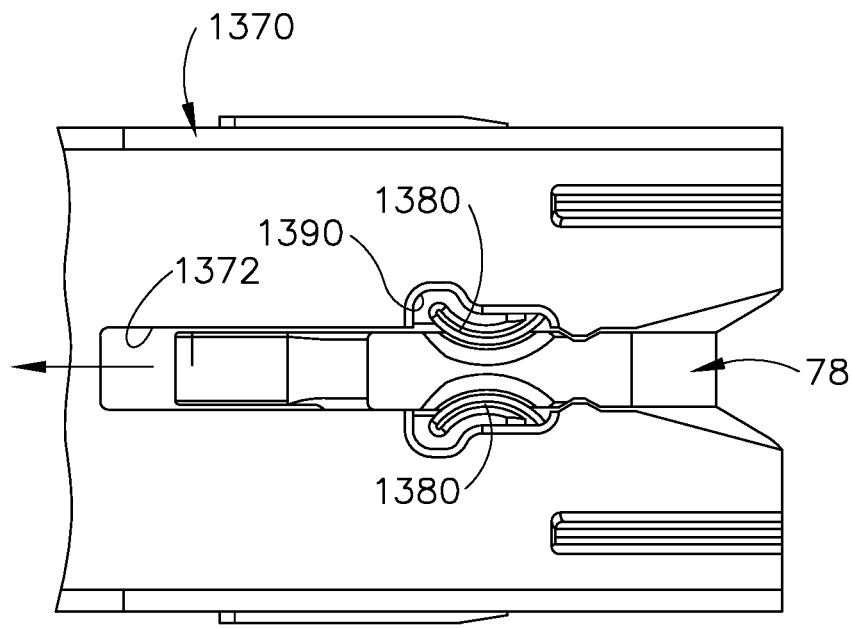
FIG. 54A depicts a bottom plan view of retention features of the buttress assembly of FIG. 52 engaged with a sled of the cartridge of FIG. 52.
Figure 54B:
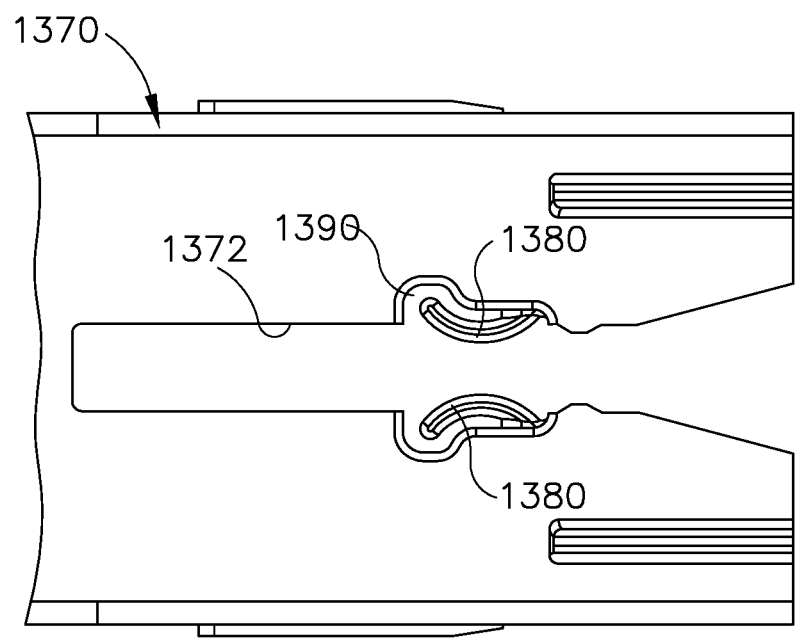
FIG. 54B depicts a bottom plan view of retention features of the buttress assembly of FIG. 52, showing the sled having moved distally and out of engagement with the retention features.

FIGS. 52 and 54A-B show another exemplary alternative staple cartridge (1370) incorporated into lower jaw (50) of end effector (40). Staple cartridge (1370) is configured to operate substantially similar to staple cartridge (70), except for the differences below. Particularly, staple cartridge (1370) includes an aperture (1390) positioned proximal to staple openings (1345). Aperture (1390) is formed as lateral extensions of slot (1372). Aperture (1390) and the portion of slot (1372) that is coincident with aperture (1390) are configured to receive attachment features (1080) of a buttress assembly (1010) in order to removably and mechanically couple buttress assembly (1010), as discussed in further detail below.

Figure 53:
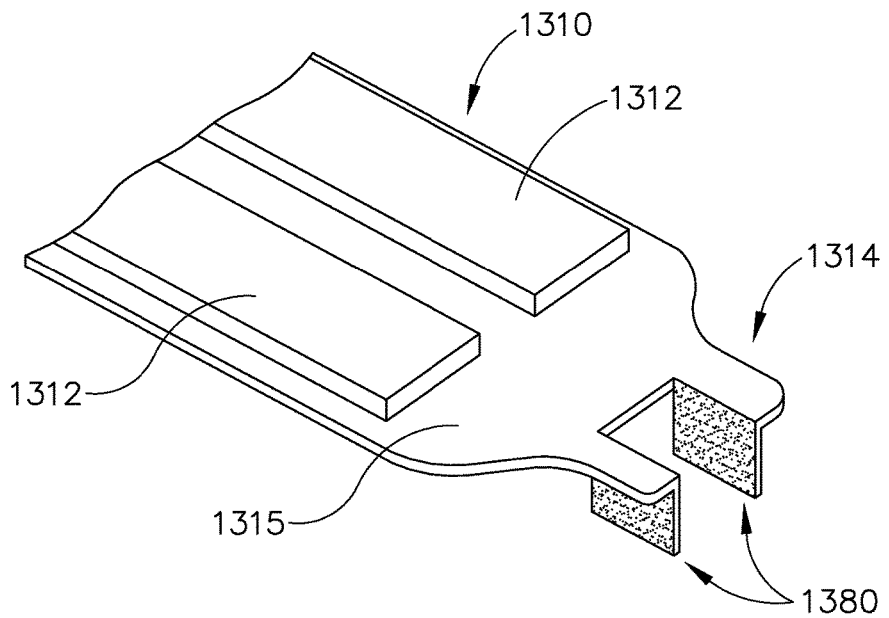
FIG. 53 depicts a partial perspective view of the proximal end of the buttress assembly of FIG. 52.

As shown best in FIGS. 52-53, buttress assembly (1310) includes a pair of buttress bodies (1312) coupled to a base portion (1315). In the present example, each buttress body (1312) comprises a strong yet flexible material configured to structurally support a line of staples (90). By way of example only, buttress body (1312) may comprise a woven mesh of VICRYL® (polyglactin 910) material by Ethicon US, LLC, and base portion (1315) may comprise the same or different material (e.g., a thin film, etc.). Alternatively, any other suitable materials or combinations of materials may be used in addition to or as an alternative to VICRYL® material to form buttress body (1312) and/or base portion (1315). Of course, buttress body (1312) and base portion (1315) may take any other suitable form and may be constructed of any other suitable material(s).

In the present example, buttress assembly (1310) includes a proximal end (1314) and a distal end (1316) and extends along an axis (1327) thereof. As shown, buttress assembly (1310) includes attachment members (1380) extending from proximal end (1314) of base portion (1315) in a perpendicular direction away from buttress body (1012) and base portion (1315). Attachment members (1380) comprise resilient tabs that comprise the same material or materials as base member (1312). In other examples, any or all of tabs (1380) may comprise a plurality of laminate, bioabsorbable layers, which may or may not include a layer that comprises part of base member (1312). In some examples, any or all of resilient tabs (1380) may comprise a woven, non-woven, or foam material. Other suitable configurations and materials that tabs (1380) may comprise will be apparent to persons skilled in the art in view of the teachings herein.

In order to removably couple buttress assembly (1310) to cartridge (1370), an operator may direct resilient tabs (1380) into aperture (1390) downwardly through aperture (1390) until tabs (1380) engage sled (78), and face (1313) of buttress body (1312) is substantially flush with cartridge deck (1373). As shown best in FIGS. 54A-54B, tabs (1380) resiliently engage sled, thereby releasably coupling buttress assembly (1310) to sled (78), and thereby releasably coupling buttress assembly (1310) to cartridge (1370).

The retention force provided by the engagement between tabs (1380) and sled (78) is sufficient to maintain the removable coupling between buttress assembly (1310) and cartridge (1370) absent a sufficient decoupling force. However, buttress assembly (1310) is configured to decouple from cartridge (1370) in response to a sufficient decoupling force input. In the present example, longitudinal movement of sled (78) disengages sled (78) from tabs (1380), releasing the retention force between sled (78) and tabs (1380). Moreover, the upward force associated with being captured by staples (90) provides additional and sufficient decoupling force to release buttress assembly (1310) from connector portions (1380) of cartridge (1370).

Figure 55:
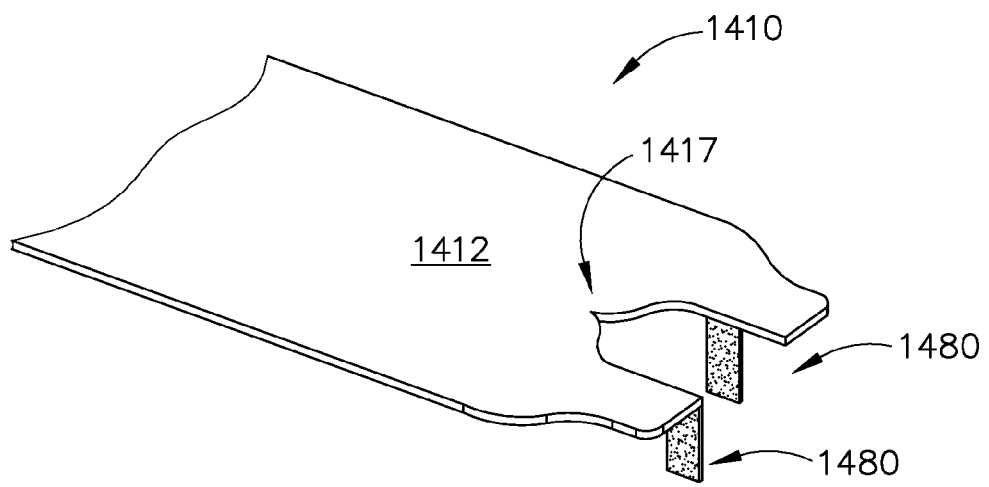
FIG. 55 depicts a partial perspective view of the proximal end of another exemplary alternative buttress assembly that may be applied to the end effector of FIG. 2.

FIG. 55 shows another alternative exemplary buttress assembly (1410). Buttress assembly (1410) is substantially similar to buttress assembly (1310) except for that resilient tabs (1480) are longitudinally staggered. Moreover, buttress assembly (1410) includes a medial cut edge portion (1417) that facilitates severing of buttress body (1412) by knife member (80) and thus traversal of knife member (80) through buttress body (1412). It should be understood that upon actuation of end effector (40), a series of staples (90) will similarly capture and retain buttress assembly (1310, 1410) against layers of tissue ($T_1$, $T_2$), thereby securing buttress assembly (1310, 1410) to tissue ($T_1$, $T_2$) in a similar manner as shown in FIG. 6. In some examples, buttress assembly (1310, 1410) may be utilized in conjunction with buttress assembly (100) on anvil (60) such that a series of staples (90) will similarly capture and retain buttress assemblies (100, 1310, 1410) against layers of tissue ($T_1$, $T_2$), thereby securing buttress assemblies (100, 1310, 1410) to tissue ($T_1$, $T_2$) in a similar manner as shown in FIG. 6.

D. Buttress Assemblies with Features to Facilitate Knife Member Traversal

Figure 56:
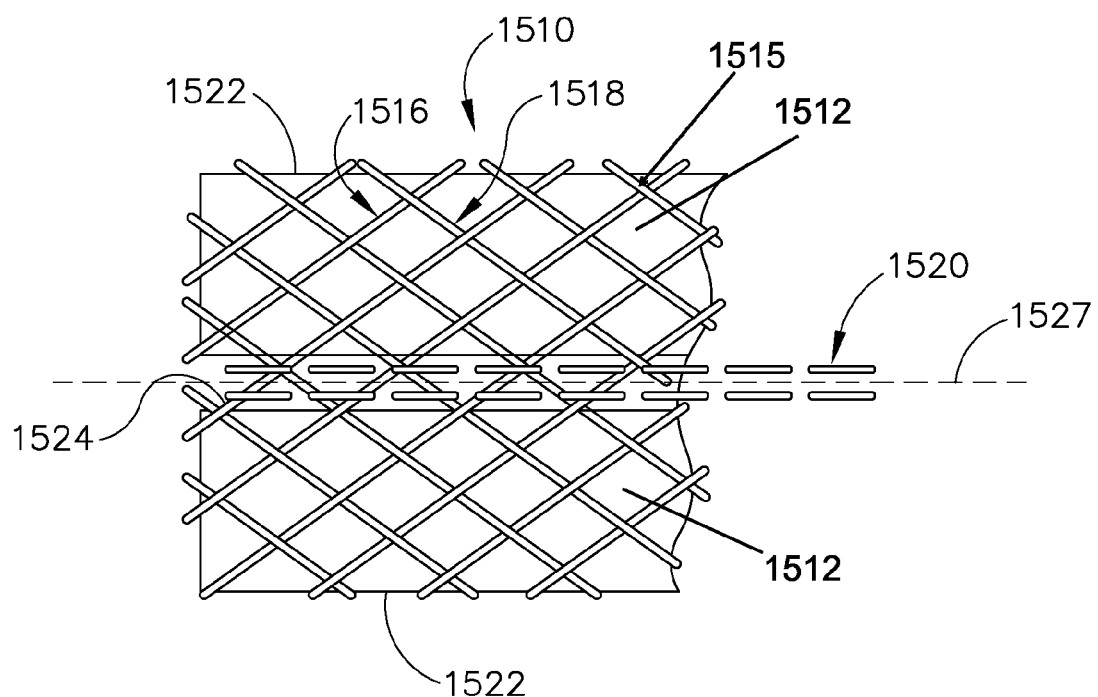
FIG. 56 depicts a partial top plan view of another exemplary alternative buttress assembly that may be applied to the end effector of FIG. 2.
Figure 57:
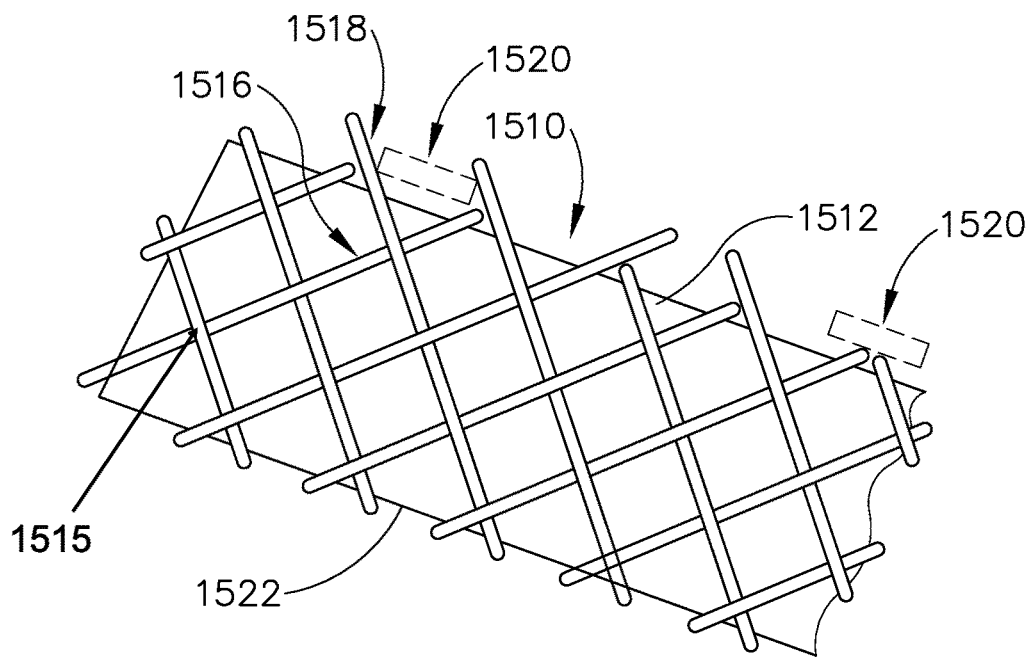
FIG. 57 depicts a perspective view of the buttress assembly of FIG. 56 after having been severed after actuation of the end effector FIG. 2.

FIG. 56 shows an exemplary alternative buttress assembly (1510) including a pair of buttress bodies (1512) that are connected by a diagonal woven mesh (1515). While only a portion of buttress assembly (1510) is shown, it will be understood that buttress assembly (1510) may be incorporated into a suitable staple cartridge (e.g., staple cartridge (70)) of a surgical instrument (e.g., instrument (10)) and may be utilized in steps of a surgical stapling procedure, such as those shown in FIGS. 5A-6. Moreover, the construction of buttress assembly (1510) may be readily incorporated into any of the various buttress assemblies described herein.

In the example shown, buttress bodies (1512) are coupled to one another via a woven mesh (1515) of material filaments. A first portion (1516) of filaments which the mesh (1515) comprises extend at an oblique angle (e.g., forty five degrees as shown) relative to the longitudinal axis (1527), and a second portion of filaments (1518) extend orthogonally relative to the first portion (1516) and at an oblique angle relative to the longitudinal axis (1527) (e.g., forty five degrees as shown).

In the present example, filaments comprising mesh (1515) are made of VICRYL® (polyglactin 910) material by Ethicon US, LLC. Buttress body (1512) is comprised of a film or woven mesh of VICRYL® (polyglactin 910) material by Ethicon US, LLC. Alternatively, any other suitable materials or combinations of materials may be used in addition to or as an alternative to VICRYL® material to form buttress body (1512) or filaments of mesh (1515). Of course, buttress body (1512) and mesh (1515) may take any other suitable form and may be constructed of any other suitable material(s).

Figure 65:
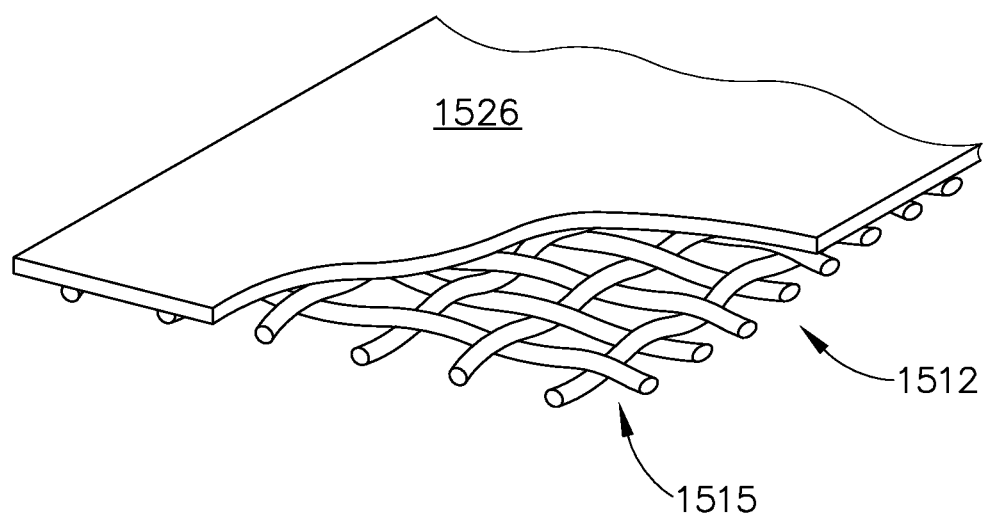
FIG. 65 depicts a perspective view of another exemplary alternative buttress assembly that may be applied to the end effector of FIG. 2.

In the present example, portions of mesh (1515) that are coincident with buttress bodies (1512) are bonded or otherwise coupled to a top portion of buttress bodies (1512). In addition or in the alternative, mesh (1515) may be bonded or otherwise coupled along a bottom portion of buttress bodies (1512). As another merely illustrative alternative, mesh (1515) may be at least partially impregnated within one or both of buttress bodies (1512). In the example shown, mesh (1515) is a woven mesh, but in other examples, mesh (1515) may be knitted or formed in any other suitable manner. In some examples, mesh (1515) may be severed and formed using heat or other forms of energy so as to fuse the filaments together as they are cut to, for example, prevent rough edges. Other suitable manners of coupling buttress bodies (1512) and mesh (1515) to one another, and of forming mesh (1515), will be apparent to persons skilled in the art in view of the teachings herein. In an alternative example, as shown in FIG. 65, buttress body (1512) may include a mesh (1515) according to the teachings just discussed, in combination with an integral film (1526).

Buttress assembly (1510) further includes two lines of perforations (1520) oriented at an oblique angle (forty-five degrees as shown) and parallel to the longitudinal axis (1527). In the present example, perforations (1520) may be formed using heat or other forms of energy so as to fuse the filaments together as they are cut to, for example, prevent rough edges. For example, filaments may be treated with an ultrasonic treatment, a heated knife member, laser, and other modes of treating with energy as will be understood by persons skilled in the art in view of the teachings herein. Perforations (1520) may also be formed in various other suitable manners as will be apparent to persons skilled in the art in view of the teachings herein.

Perforations (1520) facilitate separation of buttress bodies (1512) as knife member (80) traverses therebetween. More particularly, due to the perforations (1520), none of the filaments comprising mesh extend completely from one end of one buttress body to an end of the other buttress body (1512). Rather, the filaments extend from an edge (1522) of buttress body to one of the edges of perforations (1520), as represented by some of filaments extending further away from other edge (1524) of buttress body (1512) Therefore, rather than requiring knife member (80) to sever portions of mesh (1515) extending over channel (72), for example, as knife member (80) traverses channel (72), filaments may simply be pulled out of the way as buttress bodies (1512) are captured by staples (90). Thus, stress on the severed and stapled tissue, and damage and wear on knife member (80), may be decreased.

Figure 58:
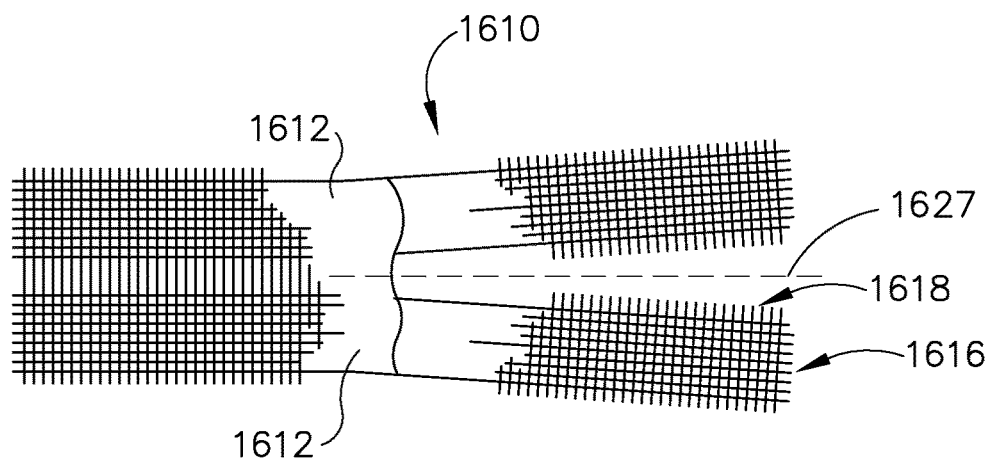
FIG. 58 depicts a top plan view of another exemplary alternative buttress assembly that may be applied to the end effector of FIG. 2, showing part of the buttress assembly having been severed after actuation of the end effector.

An alternative example of a buttress assembly (1610) is shown in FIG. 58. Buttress assembly (1610) is similar to buttress assembly (1510) in that in includes a woven mesh (1615). However, woven mesh (1615) includes a first portion (1616) of filaments that extend parallel to the longitudinal axis (1627) of buttress assembly (1610), and a second portion (1618) of filaments that extend parallel to the longitudinal axis (1627). Mesh (1615) connects opposing buttress bodies (1612). A first portion (1616) of filaments that extend parallel to axis (1627) do not extend along a portion between buttress bodies (1612). Thus, first portion of filaments are not present along channel (72) of cartridge (70) when buttress assembly (1610) is utilized with staple cartridge (70). Therefore, rather than requiring the knife member (80) to sever mesh (1515) with both portions of filament, extending over channel (72), for example, as knife member (80) traverses channel (72), knife member (80) only severs first portion (1616) (perpendicular to axis (1627)) of filaments as buttress bodies (1612) are captured by staples (90). Thus, stress on the severed and stapled tissue, and damage and wear on knife member (80), may be decreased.

In the present example, portions of mesh (1615) that are coincident with buttress bodies (1612) are bonded or otherwise coupled to a top portion of buttress bodies (1612). In addition or in the alternative, mesh (1615) may be bonded or otherwise coupled along a bottom portion. As another merely illustrative alternative, mesh (1615) may be at least partially impregnated within one or both of buttress bodies (1612). In the example shown, mesh (1615) is a woven mesh, but in other examples, mesh (1615) may be knitted or formed in any other suitable manner. In some examples, mesh (1615) may be severed and formed using heat or other forms of energy so as to fuse the filaments together as they are cut to, for example, prevent rough edges. For example, filaments may be treated with an ultrasonic treatment, a heated knife member, laser, and other modes of treating with energy as will be understood by persons skilled in the art in view of the teachings herein. Other suitable manners of coupling buttress bodies (1612) and mesh (1615) to one another, and of forming mesh (1615), will be apparent to persons skilled in the art in view of the teachings herein.

Figure 5:
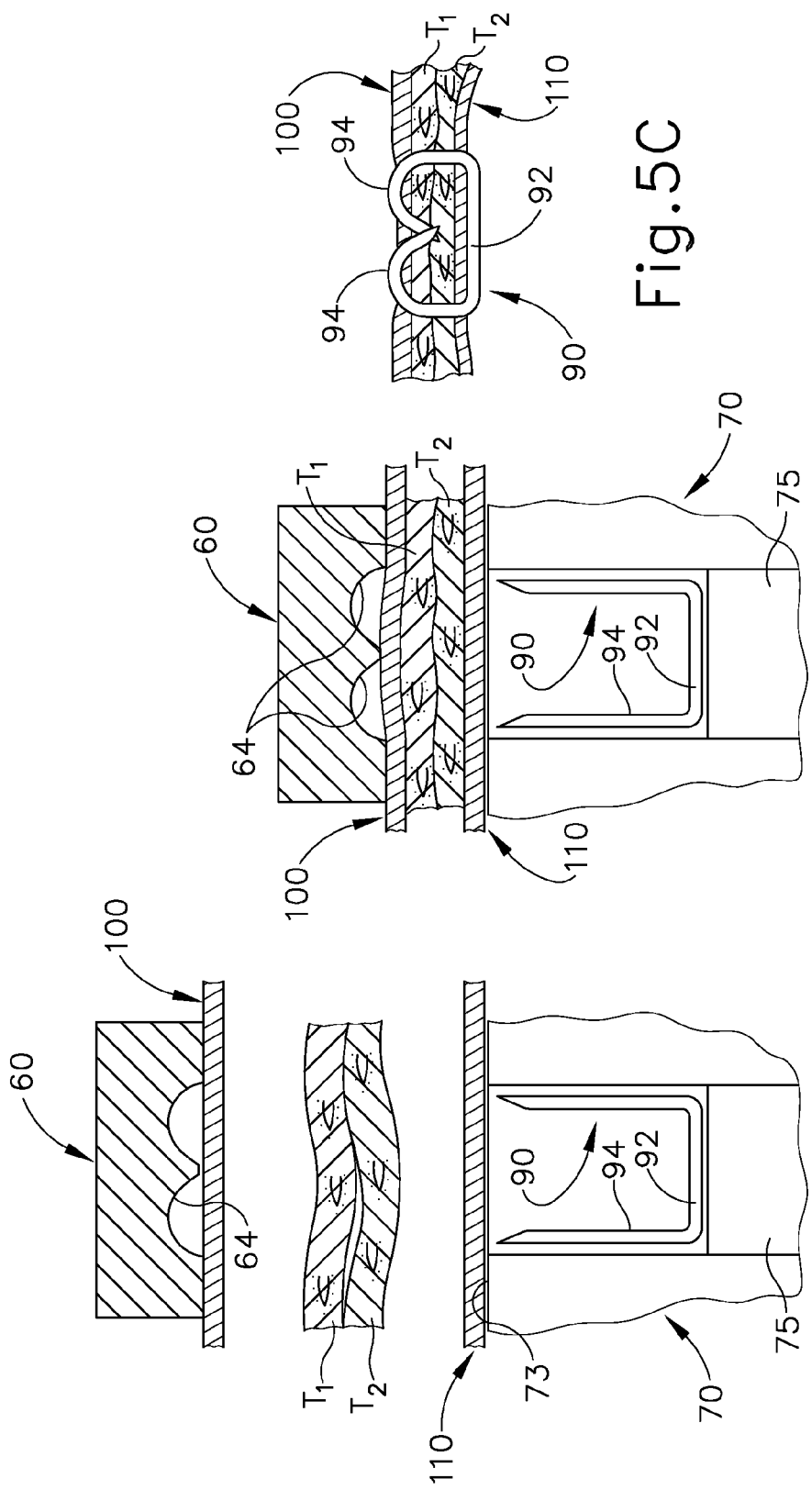
FIG. 5A depicts a cross-sectional end view of a portion of the end effector of FIG. 2 with a buttress assembly formed by the buttresses of FIG. 4 applied to the end effector, with tissue positioned between the buttresses in the end effector, and with the anvil in an open position.
FIG. 5B depicts a cross-sectional end view of the combined end effector and buttress assembly of FIG. 5A, with tissue positioned between the buttresses in the end effector, and with the anvil in a closed position.
FIG. 5C depicts a cross-sectional view of a staple and the buttress assembly of FIG. 5A having been secured to the tissue by the end effector of FIG. 2.
Figure 59:
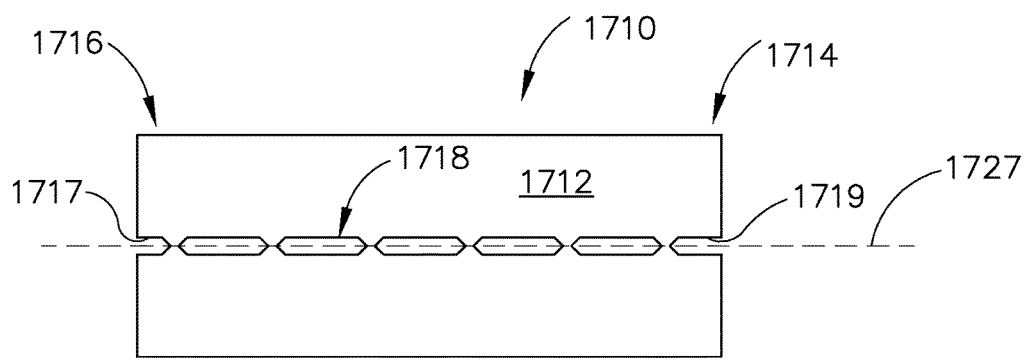
FIG. 59 depicts a top plan view of another exemplary alternative buttress assembly that may be applied to the end effector of FIG. 2.
Figure 60:
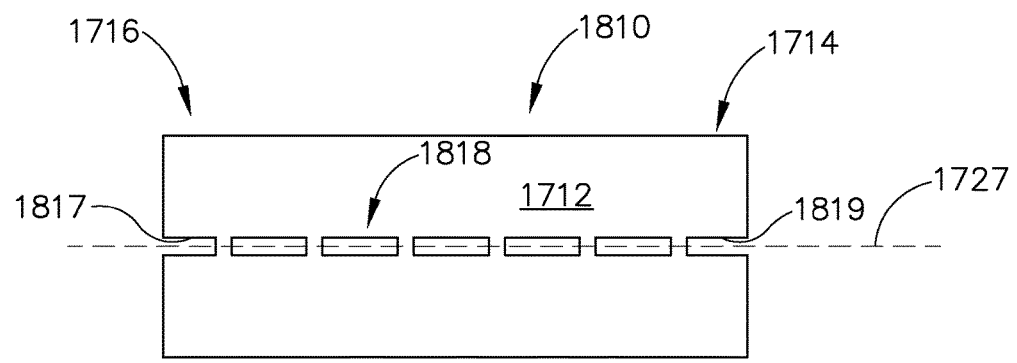
FIG. 60 depicts a top plan view of another exemplary alternative buttress assembly that may be applied to the end effector of FIG. 2.

FIGS. 59 and 60 show additional examples of buttress assemblies (1710, 1810) that may be incorporated into a suitable staple cartridge (e.g., staple cartridge (70)) of a surgical instrument (e.g., instrument (10)) and may be utilized in steps of a surgical stapling procedure, such as those shown in FIGS. 5A-6. Buttress assemblies (1710, 1810) include features that may reduce the amount of effort to advance knife member (80) through channel (72) as end effector (40) is actuated. Stress on the severed and stapled tissue, and damage and wear on knife member (80), may therefore be decreased.

As shown in FIG. 59, buttress assembly (1710) includes a buttress body (1712) including a proximal end (1714) having a proximal recess (1715), a distal end (1716) having a distal recess (1717), and a plurality of apertures (1718) extending along an axis (1727) thereof. While five apertures (1718) are shown in the present example, in alternative examples there may be less than (e.g., four, three, two, one, or zero) or more than five apertures (1718). In the present example, apertures (1718) are obround-shaped apertures, and recesses (1715, 1717) are half-obround recesses. Of course, any other suitable shapes may be used. Other suitable configurations of apertures (1718) and recesses (1715, 1717) will be apparent to persons skilled in the art in view of the teachings herein. Referring to FIG. 60, buttress assembly (1810) is substantially identical to buttress assembly (1710), except for that buttress assembly (1810) includes rectangular apertures (1818) and half-rectangular recesses (1815, 1817).

In the present examples, apertures (1718, 1818) and recesses (1715, 1815) may reduce the amount of force required for knife member (80) to cut through and traverse past severed tissue and buttress body (1712). Thus, stress on the severed and stapled tissue, and damage and wear on knife member (80), may be decreased.

Each buttress assembly (1710, 1810) of these examples comprises a buttress body (1712, 1812) and, in some instances, an adhesive layer (not shown). In the present example, each buttress body (1712, 1812) comprises a strong yet flexible material that is configured to structurally support a line of staples (90). By way of example only, each buttress body (1712, 1812) may comprise a woven mesh of VICRYL® (polyglactin 910) material by Ethicon US, LLC. Alternatively, any other suitable materials or combinations of materials may be used in addition to or as an alternative to VICRYL® material to form each buttress body (1712, 1812), such as any of the materials or configurations discussed above with respect to other disclosed buttress bodies. Of course, each buttress body (1712, 1812) may take any other suitable form and may be constructed of any other suitable material(s).

Figure 61:
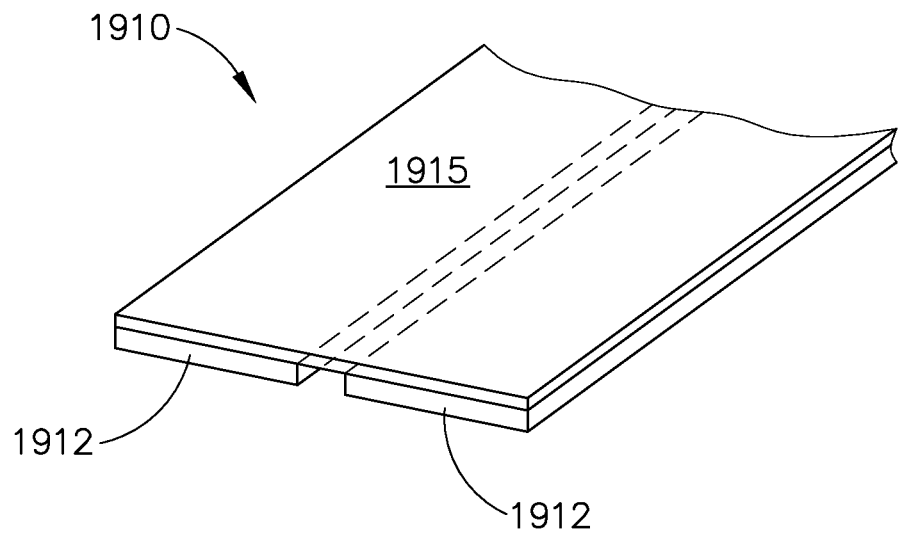
FIG. 61 depicts a partial perspective view of another exemplary alternative buttress assembly that may be applied to the end effector of FIG. 2.

FIG. 61 shows another exemplary alternative buttress assembly (1910) that may be incorporated into a suitable staple cartridge (e.g., staple cartridge (70)) of a surgical instrument (e.g., instrument (10)) and may be utilized in steps of a surgical stapling procedure, such as those shown in FIGS. 5A-6. Buttress assembly (1910) includes features that may reduce the amount of effort to advance knife member (80) through channel (72) as end effector (40) is actuated. In the example shown, buttress assembly (1910) includes a pair of buttress bodies (1912) configured such that when buttress assembly (1910) is incorporated onto staple cartridge (70), buttress bodies (1912) do not span across channel (72), such that knife member (80) does not sever buttress bodies (1912) during actuation of end effector (40). Thus, stress on the severed and stapled tissue, and damage and wear on knife member (80), may be decreased.

As shown in FIG. 61, buttress bodies (1912) are coupled to one another via a connector member (1915), such that knife member (70) would cut through at least a portion of connector member (1915). As shown, connector member (1915) comprises a sheet or thin film of material, such as wax, gelatin, or a woven or non-woven material similar to other buttress bodies described herein. Connector member (1915) may be thinner and/or weaker than buttress bodies (1912), such that knife member (80) will encounter less resistance and/or suffer from less wear when traversing connector member (1915) than knife member (80) would otherwise encounter if knife member (80) were to traverse buttress bodies (1912).

In some versions, connector member (1915) provides additional thickness to buttress bodies (1912) such that, buttress assembly (1910) provided herein may provide a. tissue compression effect between anvil (60) and deck (73) of staple cartridge (70), such as that described in U.S. patent application Ser. No. 14/810,786, entitled "Surgical Staple Cartridge with Compression Feature at Knife Slot," filed Jul. 28, 2015, issued as U.S. Pat. No. 10,314,580 on Jun. 11, 2019, the disclosure of which is incorporated by reference herein; U.S. patent application Ser. No. 14/811,087, entitled "Surgical Staple Cartridge with Compression Feature at Staple Driver Edges," filed Jul. 28, 2015, issued as U.S. Pat. No. 10,201,348 on Feb. 12, 2019, the disclosure of which is incorporated by reference herein; and U.S. patent application Ser. No. 14/811,154, entitled "Surgical Staple Cartridge with Outer Edge Compression Features," filed Jul. 28, 2015, issued as U.S. Pat. No. 10,194,192 on Feb. 5, 2019, the disclosure of which is incorporated by reference herein.

Figure 62:
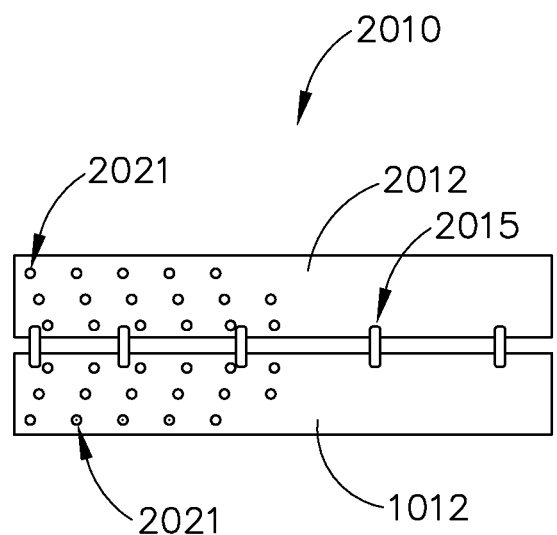
FIG. 62 depicts a top plan view of another exemplary alternative buttress assembly that may be applied to the end effector of FIG. 2.

FIG. 62 shows another exemplary alternative buttress assembly (2010) that may be incorporated into a suitable staple cartridge (e.g., staple cartridge (70)) of a surgical instrument (e.g., instrument (10)) and may be utilized in steps of a surgical stapling procedure, such as those shown in FIGS. 5A-6. Buttress assembly (2010) includes features that may reduce the amount of effort to advance knife member (80) through channel (72) as end effector (40) is actuated. In the example shown, buttress assembly (2010) includes a pair of buttress bodies (2012) configured such that when buttress assembly (2010) is incorporated onto staple cartridge (70), buttress bodies (2012) do not span across channel (72), such that knife member (80) does not sever buttress bodies (2012) during actuation of end effector (40). As shown, however, buttress bodies (2012) are coupled to one another via discrete connector members (2015) that would span channel (72) when incorporated into staple cartridge (70).

In the example shown, connector members (2015) comprise five lines of adhesive spanning between buttress bodies (2012). However, in other examples, there may be fewer or more than five lines of adhesive spanning buttress bodies (2012). Moreover, in some examples, any or all of connector members (2015) might be alternatively configured. For example, any or all of connector members (2015) may comprise filament impregnated adhesive, filaments, or other elements capable of maintaining buttress bodies (2102) in a releasably couplable relationship but that would not inhibit or impede the traversal of knife member (80). As shown, buttress bodies (2012) each include discrete portions of adhesive (2021) that may be utilized to help releasably couple buttress bodies to cartridge deck (73). As shown, discrete portions of adhesive (2021) are formed as dots and may ease the release of buttress bodies (2012) from deck (73) as buttress bodies (2012) are captured by staples (90) (e.g., as opposed to an entire sheet of adhesive coupling buttress bodies (2012) to deck (73)).

Figure 63:
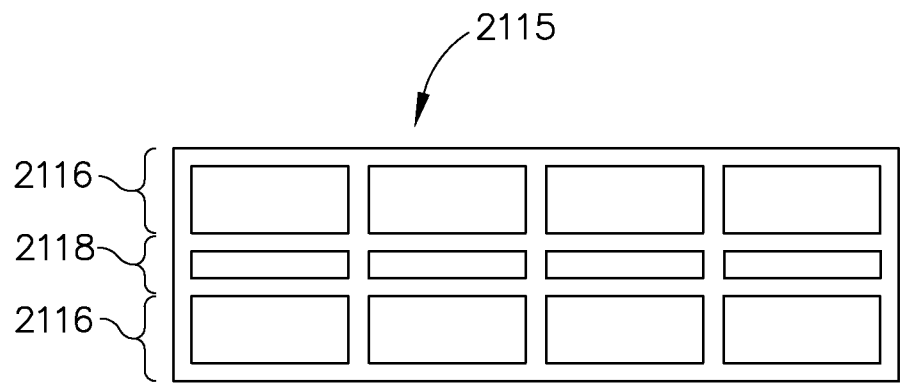
FIG. 63 depicts a top plan view of a connecting member that may be applied to the end effector of FIG. 2 to connect two portions of a buttress assembly.

FIG. 63 shows another exemplary alternative connector member (2115) that is configured to be utilized together with a buttress body, such as buttress body (1912) just discussed, and incorporated into a suitable staple cartridge (e.g., staple cartridge (70)) of a surgical instrument (e.g., instrument (10)) and utilized in steps of a surgical stapling procedure, such as those shown in FIGS. 5A-6, As shown, connector member (2115) comprises a matrix-like configuration of intersecting lines forming a generally rectangular shape. Particularly, connector member (2115) includes outer portions (2116) that are configured to lie coincidently with buttress bodies (2112) and an inner portion (2118) that is configured to span channel (72), such that buttress bodies (1912) do not span channel (72). In some versions, connector member (2115) provides an added thickness to a buttress assembly such that the buttress assembly provides a tissue compression effect between anvil (60) and lower jaw (50), such as that described in U.S. patent application Ser. No. 14/810,786 issued as U.S. Pat. No. 10,314,580 on Jun. 11, 2019; U.S. patent application Ser. No. 14/811,087, the disclosure of which is incorporated by reference herein, issued as U.S. Pat. No. 10,201,348 on Feb. 12, 2019; and U.S. patent application Ser. No. 14/811,154, issued as U.S. Pat. No. 10,194,192 on Feb. 5, 2019, the disclosure of which is incorporated by reference herein.

In the present example, connector member (2115) comprises a wax material but in other examples, all or a portion of connector member (2115) may comprise gelatin, a woven or non-woven material similar to buttress bodies (210), and/or any other suitable material(s). In the present example, buttress bodies (1912, 2012) may comprises a strong yet flexible material configured to structurally support a line of staples (90). By way of example only, buttress body (1912) may comprise a woven mesh of VICRYL® (polyglactin 910) material by Ethicon US, LLC, and base portion may comprise the same or different material. Alternatively, any other suitable materials or combinations of materials may be used in addition to or as an alternative to VICRYL® material to form buttress body (1912) and/or connector member portion (1915, 2015). Of course, buttress body (1912) and base portion (1915) may take any other suitable form and may be constructed of any other suitable material(s).

Figure 64A:
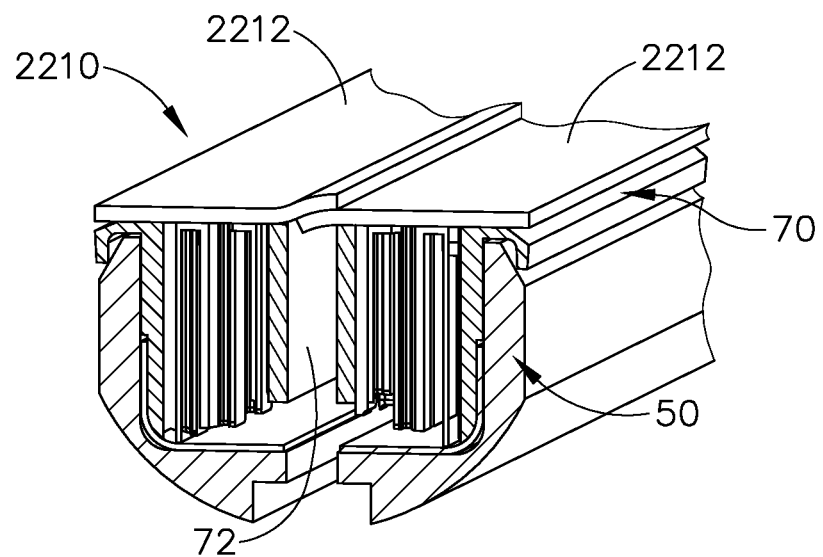
FIG. 64A depicts a perspective view of another exemplary alternative staple cartridge incorporated into the lower jaw of the end effector of FIG. 2, including another exemplary alternative buttress assembly.
Figure 64B:
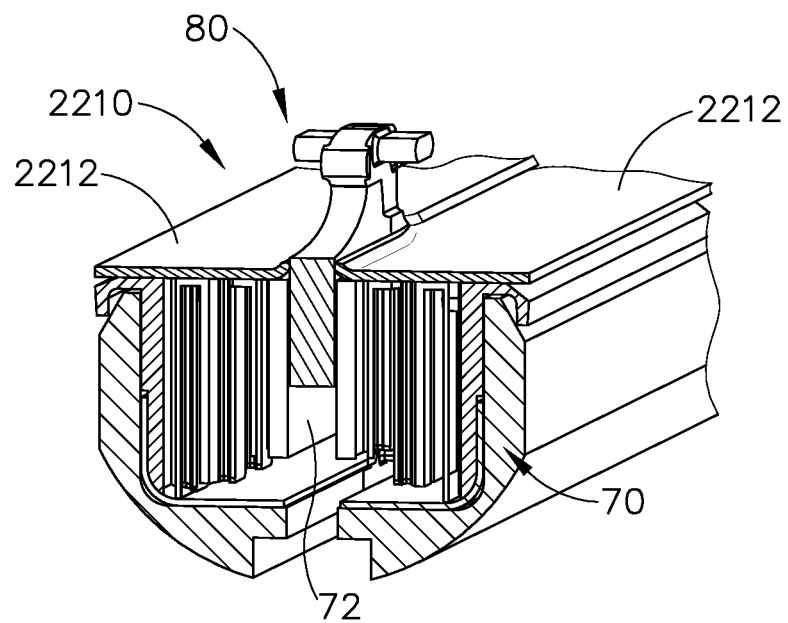
FIG. 64B depicts a perspective view of the staple cartridge of FIG. 64A, showing the buttress assembly having been displaced from a channel of the cartridge by a knife member.

FIGS. 64A-64B show another exemplary alternative buttress assembly (2210) comprising opposing buttress bodies (2212), incorporated into staple cartridge (70) of a surgical instrument (e.g., instrument (10)), which may be utilized in steps of a surgical stapling procedure, such as those shown in FIGS. 5A-6. By way of example only, buttress bodies (2212) may comprise a woven mesh of VICRYL® (polyglactin 910) material by Ethicon US, LLC. Alternatively, any other suitable materials or combinations of materials may be used in addition to or as an alternative to VICRYL® material to form buttress body (2212), such as the other configurations of buttress bodies disclosed herein.

As shown, buttress bodies (2212) are discrete members that each partially span channel (72). As shown in FIG. 64A, one buttress body (2212) partially overlaps the other buttress body (2212), though it will be understood that other overlapping configurations may be utilized. Rather than having to cut through buttress assembly (2210), as knife member (80) traverses channel (72), knife member (80) displaces buttress bodies (2212) away from channel (72) as shown in FIG. 64B. In some instances, buttress bodies (212) or knife member (80) may include a lubricious coating to reduce the friction between such components. Stress on the severed and stapled tissue and damage, and wear on knife member (80), may therefore be decreased.

E. Buttress Assemblies Covering Only a Portion of Staple Cavities

Figure 66:
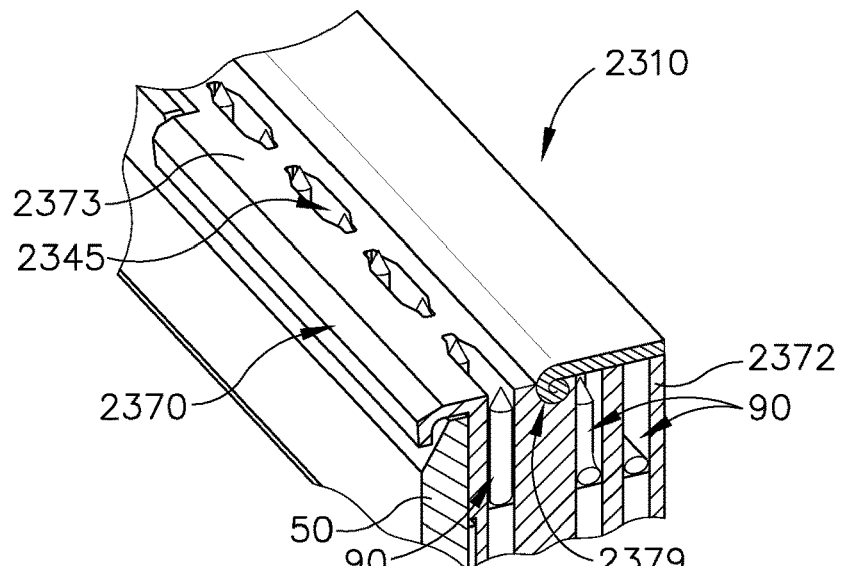
FIG. 66 depicts a cross-sectional end view of a portion of the end effector of FIG. 2 with an exemplary alternative buttress assembly applied to the end effector.
Figure 67A:
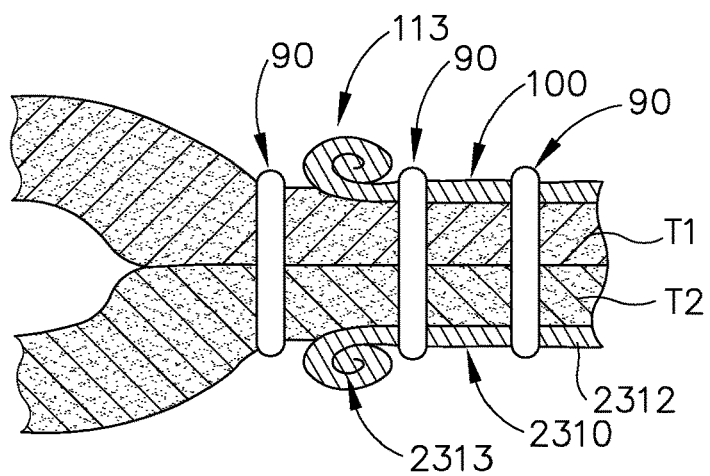
FIG. 67A depicts a cross-sectional end view of a portion of the buttress assembly of FIG. 66 applied to tissue with staples, with an end portion of the buttress assembly shown in a rolled configuration.
Figure 67B:
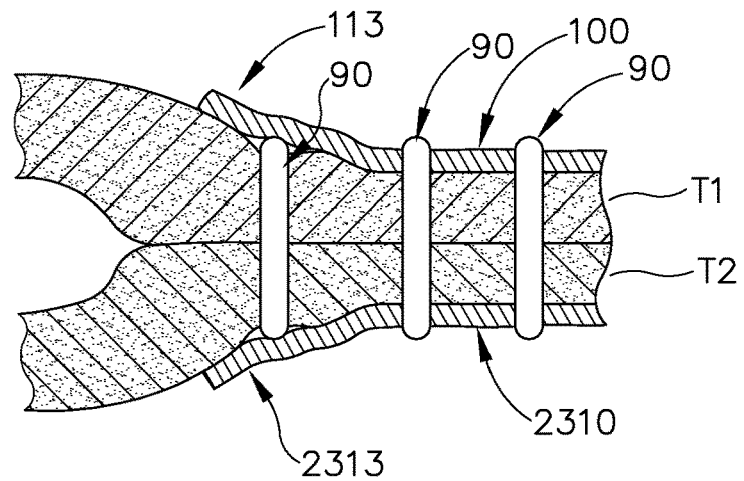
FIG. 67B depicts a cross-sectional end view of a portion of the buttress assembly of FIG. 66 applied to tissue with staples, with the end portion of the buttress assembly shown in a unrolled configuration.

FIG. 66-67B show an exemplary alternative buttress assembly (2310). As shown best in FIG. 66, buttress assembly (2310) is disposed on a staple cartridge (2370) that is configured to operate substantially similarly to staple cartridge (70) discussed above. Cartridge (2370) is removably coupled to lower jaw (50) of end effector (40). In the present example, staple cartridge (2370) includes three rows of staples (90) in three sets of cavities (2345) on each side of channel (2372) instead of two rows of staples cavities (2345). Moreover, cartridge (2370) includes an elongate trough (2379) extending along staple deck (2373). Trough (2379) extends longitudinally along the length of cartridge (2370) and is laterally positioned between the outermost row of cavities (2345) and the middle row of cavities (2345). Trough (2379) has a partially circular cross-sectional profile. In other examples, however, trough (2379) may have any other suitable shapes which as will be apparent to persons skilled in the art in view of the teachings herein.

Buttress assembly (2310) of the present example may be configured in accordance with other buttress assemblies disclosed herein. As shown, buttress body (2312) of buttress assembly (2310) extends along deck (2373) and an end portion (2313) of buttress body (2373) is disposed in a rolled configuration within trough (2379). In the present example, end portion (2313) is biased toward an unrolled configuration, but is retained in the rolled configuration when positioned within trough (2379). Other suitable configurations of buttress assembly (2310) will be apparent to persons skilled in the art in view of the teachings herein.

Upon actuation of end effector (40), staples (90) capture and retain buttress assembly (2310) against layers of tissue (T1, T2), thereby securing buttress assembly (2310) to tissue (T1, T2) in a similar manner as shown in FIG. 6. In the example shown in FIGS. 67A-67B, buttress assembly (2310) has been utilized in conjunction with buttress assembly (100) on anvil (60) such that a series of staples (90) has captured and retained buttress assemblies (100, 2310) against layers of tissue (T1, T2), thereby securing buttress assemblies (100, 2310) to tissue (T1, T2) in a similar manner as shown in FIG. 6. Similar to end portion (2313) of buttress assembly (2310), an end portion of buttress assembly (100) is shown to initially be in a rolled configuration upon being captured onto tissue (T1, T2), with the remaining portions of buttress assemblies covering the two rows of staples (90) closest to channel (2373). Thus, due to the presence of staples (90) and buttress assemblies (100, 2310) captured at the first and second rows of staples (90), there is a relatively higher level of compression at the first and second rows of staples (90), and better profusion at the third row of staples (90). As shown best in FIG. 67B, upon being captured onto tissue (T1, T2), ends (113, 2313) resiliently unfurl to transition to an unrolled position to cover the third row of staples (90). Buttress assemblies (100, 2310) thereby facilitate tissue ingrowth and seal any puncture leaks, if present.

Figure 68:
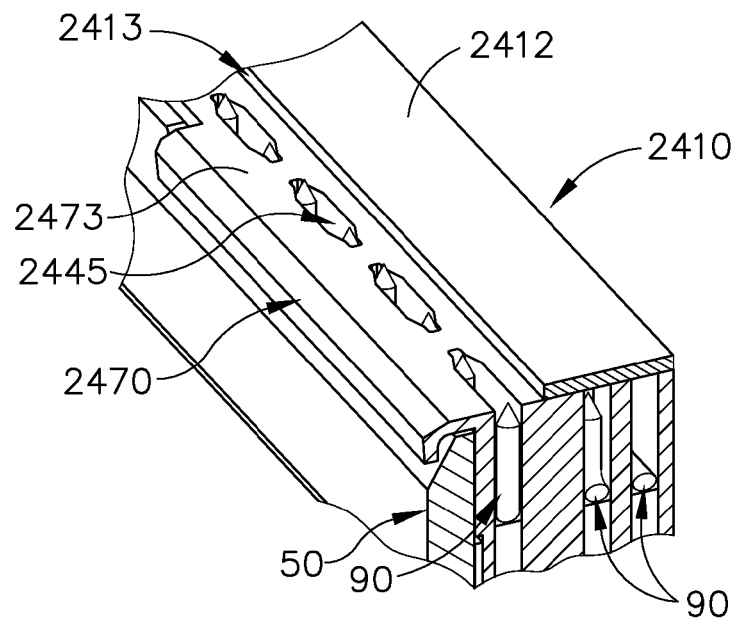
FIG. 68 depicts a cross-sectional end view of a portion of the end effector of FIG. 2 with an exemplary alternative buttress assembly applied to the end effector.
Figure 69:
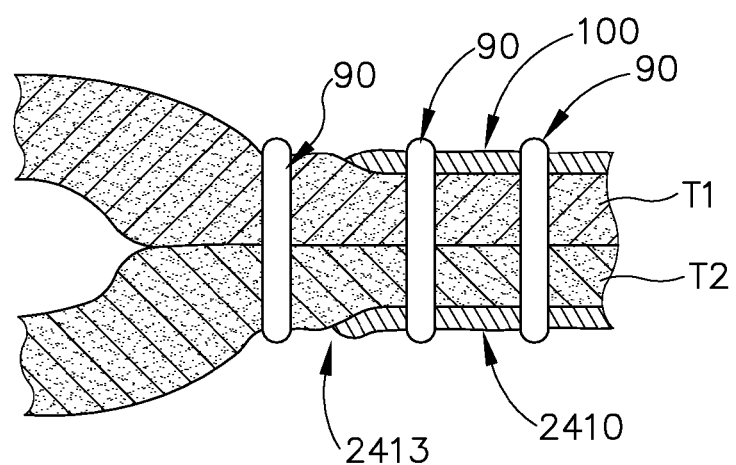
FIG. 69 depicts a cross-sectional end view of a portion of the buttress assembly of FIG. 68 applied to tissue with staples.

FIG. 68-69 show an exemplary alternative buttress assembly (2410). As shown best in FIG. 68, buttress assembly (2410) is disposed on a staple cartridge (2470) that is configured to operate substantially similarly to staple cartridge (70) discussed above. Cartridge (2470) is removably coupled to lower jaw (50) of end effector (40). Staple cartridge (2470) of this example includes three rows of staples (2490) in three sets of cavities (2445) on each side of channel (2472) instead of two rows of staples (2445).

Buttress assembly (2410) of the present example may be configured in accordance with other buttress assemblies disclosed herein. Buttress body (2412) of buttress assembly (2410) extends longitudinally along deck (2473) and laterally terminates at a position such that a lateral edge (2413) is between the outermost row of staple cavities (2445) and the middle row of staple cavities (2445). Other suitable configurations of buttress assembly (2410) will be apparent to persons skilled in the art in view of the teachings herein.

Upon actuation of end effector (40), staples (90) capture and retain buttress assembly (2410) against layers of tissue (T1, T2), thereby securing buttress assembly (2410) to tissue (T1, T2) in a similar manner as shown in FIG. 6. As shown, some examples, buttress assembly (2410) has been utilized in conjunction with buttress assembly (100) on anvil (60) such that a series of staples (90) has captured and retained buttress assemblies (100, 2410) against layers of tissue (T1, T2), thereby securing buttress assemblies (100, 2410) to tissue (T1, T2). As shown, lateral edge (2413) of buttress assembly (2410) is positioned between the outermost row of staples (90) and the intermediate row of staples (90). The rest of buttress assembly (2410) has been captured by the first and second rows of staples (90). Thus, due to the presence of staples (90) and buttress assemblies (100, 2410) captured at the first and second rows of staples (90), there is a relatively higher level of compression at the first and second rows of staples, and better profusion at the third row of staples (90).

Figure 70:
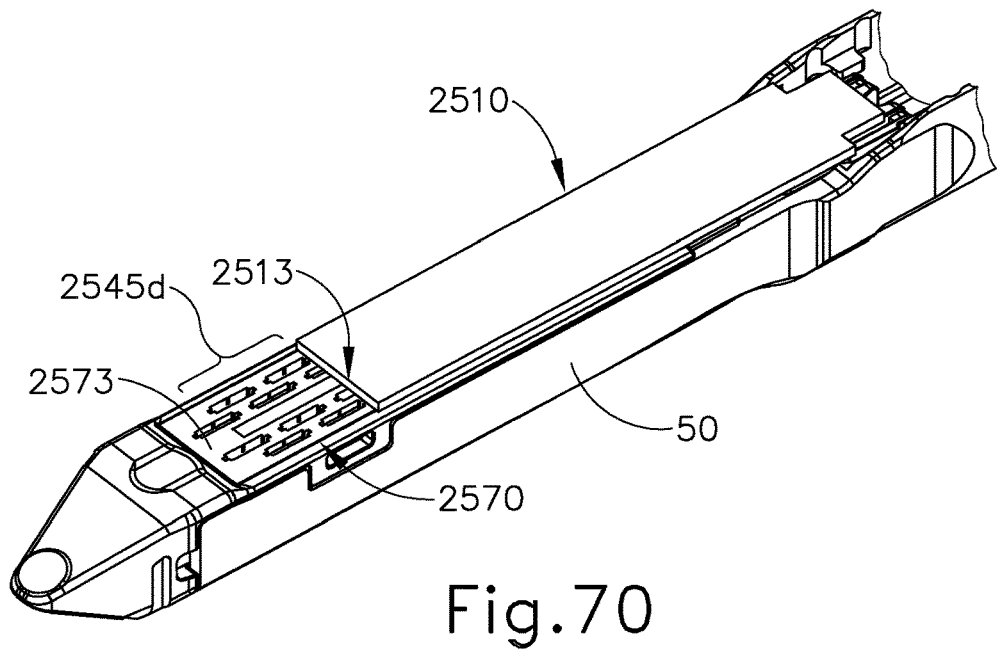
FIG. 70 depicts a perspective view of another exemplary alternative staple cartridge incorporated into the lower jaw of end effector of instrument of FIG. 1, including another exemplary alternative buttress assembly.
Figure 71:
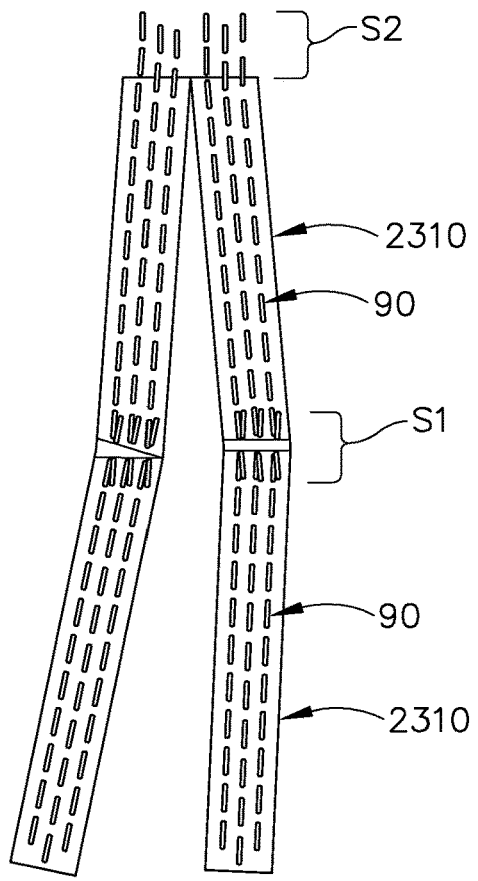
FIG. 71 depicts a top plan view of tissue severed and stapled multiple times in succession using the cartridge and buttress assembly of FIG. 70.

FIGS. 70-71 show an exemplary alternative buttress assembly (2510). As shown best in FIG. 70, buttress assembly (2510) is disposed on a staple cartridge (2570) that is configured to operate substantially similarly to staple cartridge (70) discussed above. Cartridge (2570) is removably coupled to lower jaw (50) of end effector (40). Cartridge (2570) of this example includes three rows of staples (2590) in three sets of cavities (2545) on each side of channel (2572) instead of two rows of staples (2545).

Buttress assembly (2510) of the present example may be configured in accordance with other buttress assemblies disclosed herein. As shown, buttress body (2512) of buttress assembly (2510) extends along deck (2573) and a distal end portion (2513) of buttress body (2573) terminates such that buttress assembly (2510) does not cover a distal portion (2545d) of staple cavities (2545); or a distal portion of channel (2572) or deck (2573). In other words, buttress assembly (2510) does not extend along the full length of deck (2573). Other suitable configurations of buttress assembly (2510) will be apparent to persons skilled in the art in view of the teachings herein.

Upon actuation of end effector (40), staples (90) capture and retain buttress assembly (2510) against layers of tissue (T1, T2), thereby securing buttress assembly (2510) to tissue (T1, T2) in a similar manner as shown in FIG. 6. FIG. 71 shows a plurality of buttress assemblies (2510) that have been deployed with staples (90) onto tissue, after actuating end effector (40) multiple times. Due to the configuration of buttress assembly (2510) terminating proximal to distal portion (2545d), when buttress assembly (2510) and staples (90) are deployed onto tissue, a portion of stapled tissue includes staples (90) but does not include buttress assembly (2510), such as at region (S2). However, at region (S1), which has been severed and stapled with successive lines of staples (90), a region (S2) of overlap occurs. Notably, due to the lack of buttress (2510) at distal portion (2545d), successive staple lines overlap (as shown by more than three rows of staples (90) at region (S1)), but overlapping portions of buttress assemblies (2510) are not created.

In some examples, buttress assembly (2510) may be utilized in conjunction with buttress assembly (100) on anvil (60) such that a series of staples (90) will similarly capture and retain buttress assemblies (100, 2510) against layers of tissue ($T_1$, $T_2$), thereby securing buttress assemblies (100, 2510) to tissue ($T_1$, $T_2$) in a similar manner as shown in FIG. 6. Of course, buttress assembly (100) in such instances may be modified to be configured substantially identical to buttress assembly (2510).

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising a staple cartridge, wherein the staple cartridge comprises: (i) a plurality of staples, (ii) a deck, wherein the deck defines a plurality of openings, wherein each opening of the plurality of openings is associated with a corresponding staple of the plurality of staples, such that each staple is configured to pass through a corresponding opening of the plurality of openings, wherein the deck further comprises a first mechanical coupling feature, and (iii) a buttress assembly, comprising: (A) a buttress body, and (B) a second mechanical coupling feature, wherein the second mechanical coupling feature is configured to engage the first mechanical coupling feature to releasably couple the buttress body to the deck.

Example 2

The apparatus of Example 1, wherein the first mechanical coupling feature comprises an aperture in the deck, wherein the second mechanical coupling feature is configured to be received within the aperture.

Example 3

The apparatus of Example 2, wherein the second mechanical coupling feature comprises a tab coupled to the buttress body.

Example 4

The apparatus of any one or more of Examples 1 through 3, wherein the cartridge further comprises a sled member disposed in the cartridge below the deck, wherein the sled member is configured to traverse longitudinally below the deck.

Example 5

The apparatus of Example 4, wherein first mechanical coupling feature comprises the sled member.

Example 6

The apparatus of Example 5, wherein the deck comprises an aperture, wherein the second mechanical coupling feature is configured to be received within the aperture, wherein the second mechanical coupling feature is configured to engage with the sled in response to being directed into the aperture.

Example 7

The apparatus of any one or more of Examples 5 through 6, wherein the deck defines an outer portion and an inner portion, wherein the first mechanical coupling feature further comprises the inner portion of the deck.

Example 8

The apparatus of Example 7, wherein the second mechanical coupling feature is configured to engage with the sled and the inner portion of the deck in response to being directed into the aperture.

Example 9

The apparatus of any one or more of Examples 1 through 8, wherein the first mechanical coupling feature is bonded to the deck.

Example 10

The apparatus of any one or more of Examples 1 through 9, wherein the second mechanical coupling feature comprises a slot in the buttress body.

Example 11

The apparatus of Example 10, wherein the buttress body defines a longitudinal axis, wherein the slot is positioned transverse to the slot.

Example 12

The apparatus of any one or more of Examples 10 through 11, wherein the wherein the buttress body defines a longitudinal axis, wherein the slot is positioned parallel to the slot.

Example 13

The apparatus of any one or more of Examples 1 through 12, wherein the buttress body comprises: (1) a first discrete buttress portion on one side of the deck, and (2) a second discrete buttress portion on another side of the deck.

Example 14

The apparatus of any one or more of Examples 1 through 13, wherein the second mechanical coupling feature extends from the buttress body, wherein the second mechanical coupling feature comprises a different material than the buttress body.

Example 15

The apparatus of claim 1, further comprising: (a) an end effector, wherein the end effector comprises: (i) an anvil, and (ii) a lower jaw, wherein the anvil is pivotable toward the lower jaw to capture tissue between the anvil and the lower jaw, wherein the staple cartridge is secured to the lower jaw; and (b) a stapling and severing mechanism in communication with the shaft assembly and end effector, wherein the stapling and severing mechanism is configured to sever and staple tissue clamped between the anvil and the lower jaw.

Example 16

An apparatus comprising a staple cartridge, wherein the staple cartridge comprises: (i) a plurality of staples, (ii) a deck, wherein the deck defines a plurality of openings, wherein each opening of the plurality of openings is associated with a corresponding staple of the plurality of staples, such that each staple is configured to pass through a corresponding opening of the plurality of openings, and (iii) a buttress assembly disposed on the deck, wherein the buttress assembly covers less than all of the plurality of openings such that a first portion of the staples is configured to capture a portion of the buttress as the first portion of the staples passes through a corresponding opening, and such that a second portion of the staples is configured not to capture a portion of the buttress as the second portion of staples passes through a corresponding opening.

Example 17

The apparatus of Example 16, wherein the deck defines a channel, wherein the plurality of openings defines an inner longitudinally extending row of openings and an outer longitudinally extending row of openings, wherein the outer longitudinally extending row of openings is laterally positioned further from the channel than the inner longitudinally extending row of openings, wherein the buttress assembly does not cover the outer longitudinally extending row of openings.

Example 18

The apparatus of any one or more of Examples 16 through 17, wherein the deck defines a distal portion and a proximal portion, wherein the buttress assembly covers the openings at the proximal portion but not at the distal portion.

Example 19

An apparatus comprising a surgical buttress assembly, the buttress assembly comprising: (i) a first buttress body, (ii) a second buttress body spaced apart from the first buttress body thereby defining a gap between the first buttress body and the second buttress body, and (iii) a connecting structure connecting the first buttress body to the second buttress body, wherein a first portion of the connecting structure is coincident with one or both of the first buttress body and second buttress body, wherein a second portion of the connecting structure is coincident with the gap, wherein the second portion is less dense than the first portion.

Example 20

The apparatus of Example 19, wherein the connecting structure comprises a plurality of filaments.

V. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

In addition to the foregoing, it should also be understood that any of the various buttress assemblies described herein may be further constructed and operable in accordance with at least some of the teachings of U.S. patent application Ser. No. 14/667,842, entitled "Method. of Applying a Buttress to a Surgical Stapler," filed Mar. 25, 2015, issued as U.S. Pat. No. 10,349,939 on Jul. 16, 2019, the disclosure of which is incorporated by reference herein, U.S. patent application Ser. No. 14/827,856, entitled "Implantable Layers for a Surgical Instrument," filed Aug. 17, 2015, published as U.S. Pub. No. 2017/0049444 on Feb. 23, 2017, the disclosure of which is incorporated by reference herein; U.S. patent application Ser. No. 14/871,071, entitled "Compressible Adjunct with Crossing Spacer Fibers," filed Sep. 30, 2015, issued as U.S. Pat. No. 10,433,846 on Oct. 8, 2019, the disclosure of which is incorporated by reference herein; and U.S. patent application Ser. No. 14/871,131, entitled "Method for Applying an Implantable Layer to a Fastener Cartridge," filed Sep. 30, 2015, published as U.S. Pub. No. 2017/0086842 on Mar. 30, 2017, the disclosure of which is incorporated by reference herein. Furthermore, in addition to the methods described herein, any of the various buttress assemblies described herein may be applied to end effector (40) in accordance with at least some of the teachings of U.S. Provisional Patent App. No. 62/209,041; entitled "Method and Apparatus for Applying a Buttress to End Effector of a Surgical Stapler," filed Aug. 24, 2015, the disclosure of which is incorporated by reference herein; and/or U.S. patent application Ser. No. 14/871,131, entitled "Method for Applying an Implantable Layer to a Fastener Cartridge," filed Sep. 30, 2015, published as U.S. Pub. No. 2017/0086842 on Mar. 30, 2017, the disclosure of which is incorporated by reference herein. Various suitable ways in which the teachings herein may be combined with various teachings of the above-cited references will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California. Similarly, those of ordinary skill in the art will recognize that various teachings herein may be readily combined with various teachings of any of the following: U.S. Pat. No. 5,792,135, entitled "Articulated Surgical instrument For Performing Minimally invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued. Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator :Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pub. No. 2013/0012957, entitled "Automated End Effector Component Reloading System for Use with a Robotic System, published Jan. 10, 2013, issued as U.S. Pat. No. 8,844,789 on Sep. 30, 2014, the disclosure of which is incorporated by reference herein; U.S. Pub. No. 2012/0199630, entitled "Robotically-Controlled Surgical Instrument with Force-Feedback Capabilities," published Aug. 9, 2012, issued as U.S. Pat. No. 8,820,605 on Sep. 2, 2014, the disclosure of which is incorporated by reference herein; U.S. Pub. No. 2012/0132450, entitled "Shiftable Drive interface for Robotically-Controlled Surgical Tool," published May 31, 2012, issued as U.S. Pat. No. 8,616,431 on Dec. 31, 2013, the disclosure of which is incorporated by reference herein; U.S. Pub. No. 2012/0199633, entitled "Surgical Stapling Instruments with Cam-Driven Staple Deployment Arrangements," published Aug. 9, 2012, issued as U.S. Pat. No. 8,573,461 on Nov. 5, 2013, the disclosure of which is incorporated by reference herein; U.S. Pub. No. 2012/0199631, entitled "Robotically-Controlled Motorized Surgical End Effector System with Rotary Actuated Closure Systems Having Variable Actuation Speeds," published Aug. 9, 2012, issued as U S. Pat. No. 8,602,288 on Dec. 10, 2013, the disclosure of which is incorporated by reference herein; U.S. Pub. No. 2012/0199632, entitled "Robotically-Controlled Surgical Instrument with Selectively Articulatabile End Effector," published Aug. 9, 2012, issued as U.S. Pat. No. 9,301,759 on Apr. 5, 2016, the disclosure of which is incorporated by reference herein; U.S. Pub. No. 2012/0203247, entitled "Robotically-Controlled Surgical End Effector System," published Aug. 9, 2012, issued as U.S. Pat. No. 8,783,541 on Jul. 22, 2014, the disclosure of which is incorporated by reference herein; U.S, Pub. No. 2012/0211546, entitled "Drive Interface for Operably Coupling a Manipulatable Surgical Tool to a Robot," published Aug. 23, 2012, issued as U.S. Pat. No. 8,479,969 on Jul. 9, 2013; U.S. Pub. No. 2012/0138660, entitled "Robotically-Controlled Cable-Based Surgical End Effectors," published Jun. 7, 2012, issued as U.S. Pat. No. 8,800,838 on Aug. 12, 2014, the disclosure of which is incorporated by reference herein; and/or U.S. Pub. No. 2012/0205421, entitled "Robotically-Controlled Surgical End Effector System with Rotary Actuated Closure Systems," published Aug. 16, 2012, issued as U.S. Pat. No. 8,573,465 on Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising a staple cartridge, wherein the staple cartridge comprises:
   (i) a plurality of staples,
   (ii) a deck, wherein the deck defines a plurality of openings, wherein each opening of the plurality of openings is associated with a corresponding staple of the plurality of staples, such that each staple is configured to pass through a corresponding opening of the plurality of openings, wherein the deck further comprises a first mechanical coupling feature, wherein the first mechanical coupling feature comprises a recess formed in an upper surface of the deck, and
   (iii) a buttress assembly, comprising:
      (A) a buttress body,
      (B) a second mechanical coupling feature comprising an upward U-shaped tab that faces upwardly away from the staple cartridge, wherein the upward U-shaped tab is disposed at a proximal terminal end of the buttress body, wherein the upward U-shaped tab is configured to be received within the recess and to engage the recess to releasably couple the buttress body to the deck, and
      (C) first and second lateral tabs disposed at first and second lateral outer sides of the buttress assembly, wherein the first and second lateral tabs extend at an oblique angle relative to a plane defined by an upper face of the buttress body and downwardly toward the staple cartridge.

2. The apparatus of claim 1, wherein the cartridge further comprises a sled member disposed in the cartridge below the deck, wherein the sled member is configured to traverse longitudinally below the deck.

3. The apparatus of claim 2, wherein the upward U-shaped tab is configured to slidably engage with the sled member in response to longitudinal traversal of the sled member below the deck to release the upward U-shaped tab from the recess.

4. The apparatus of claim 1, wherein the buttress body comprises:
(1) a first discrete buttress portion, and
(2) a second discrete buttress portion separated entirely from the first discrete buttress portion by a longitudinally extending channel.

5. The apparatus of claim 1, wherein the second mechanical coupling feature extends from the buttress body, wherein the second mechanical coupling feature comprises a different material than the buttress body.

6. The apparatus of claim 1, further comprising:
(a) an end effector, wherein the end effector comprises:
 (i) an anvil, and
 (ii) a lower jaw, wherein the anvil is pivotable toward the lower jaw to capture tissue between the anvil and the lower jaw, wherein the staple cartridge is secured to the lower jaw; and
(b) a stapling and severing mechanism in communication with a shaft assembly and the end effector, wherein the stapling and severing mechanism is configured to sever and staple tissue clamped between the anvil and the lower jaw.

7. The apparatus of claim 2, wherein the upward U-shaped tab is configured to contact the deck and the sled member to decouple the buttress assembly from the deck.

8. A staple cartridge, wherein the staple cartridge comprises:
(a) a plurality of staples;
(b) a deck, wherein the deck defines a plurality of openings, wherein each opening of the plurality of openings is associated with a corresponding staple of the plurality of staples, such that each staple is configured to pass through a corresponding opening of the plurality of openings;
(c) a first mechanical coupling feature comprising first and second connectors coupled with the deck, wherein the first and second connectors each include a first end having a first width, a middle portion having a second width less than the first width, and a second end having a third width greater than the first width; and
(d) a buttress assembly, comprising:
 (i) a buttress body, and
 (ii) a second mechanical coupling feature comprising first and second slots, wherein the first and second slots are configured to engage the first and second connectors to releasably couple the buttress body to the deck in a first position, wherein the first and second slots are configured to disengage the first and second connectors to release the buttress body from the deck in a second position.

9. The staple cartridge of claim 8, wherein the first connector is a proximal connector, the second connector is a distal connector, the first slot is a proximal slot, and the second slot is a distal slot, wherein the proximal connector is configured to release from the proximal slot as a knife member and a sled travel longitudinally and the distal connector is configured to release from the distal slot as the knife member and the sled travels further longitudinally.

10. The staple cartridge of claim 8, wherein the first end of the first and second connectors are triangular shaped, diamond shaped, or circular shaped.

11. The apparatus of claim 1, wherein the upward U-shaped tab comprises the same material or materials as the buttress body.

12. The apparatus of claim 1, wherein the upward U-shaped tab is integrally formed as unitary piece together with the buttress body.

13. The apparatus of claim 1, wherein the upward U-shaped tab comprises a plurality of laminate, bioabsorbable layers.

14. An apparatus comprising a staple cartridge, wherein the staple cartridge comprises:
(i) a plurality of staples,
(ii) a deck, wherein the deck defines a plurality of openings, wherein each opening of the plurality of openings is associated with a corresponding staple of the plurality of staples, such that each staple is configured to pass through a corresponding opening of the plurality of openings, wherein the deck further comprises a first mechanical coupling feature, wherein the first mechanical coupling feature comprises a recess formed in an upper surface of the deck, and
(iii) a buttress assembly, comprising:
 (A) a buttress body,
 (B) a second mechanical coupling feature comprising a distally tapering retention tab disposed at a distal terminal end of the buttress body, wherein the distally tapering retention tab tapers downwardly in a distal direction away from the buttress body, wherein the distally tapering retention tab is configured to be received within the recess and to engage the recess to releasably couple the buttress body to the deck, and
 (C) first and second lateral tabs disposed at first and second lateral outer sides of the buttress assembly, wherein the first and second lateral tabs extend at an oblique angle relative to a plane defined by an upper face of the buttress body and downwardly toward the staple cartridge.

15. The apparatus of claim 14, wherein the distally tapering retention tab is integrally formed as unitary piece together with the buttress body.

* * * * *